(12) United States Patent
Hoye et al.

(10) Patent No.: US 9,850,261 B2
(45) Date of Patent: *Dec. 26, 2017

(54) SILICON-BASED CROSS COUPLING AGENTS AND METHODS OF THEIR USE

(71) Applicant: The Trustees of The University of Pennsylvania, Philadelphia, PA (US)

(72) Inventors: Adam T. Hoye, Bala Cynwyd, PA (US); Won-Suk Kim, Seoul (KR); Dionicio Martinez-Solorio, Bala Cynwyd, PA (US); Amos B. Smith, III, Merion, PA (US); Rongbiao Tong, Hong Kong (CN); Minh Huu Nguyen, Philadelphia, PA (US); Luis Sanchez, Lewiston, NY (US); Bruno Nicolas Melillo, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/326,069

(22) PCT Filed: Jul. 16, 2015

(86) PCT No.: PCT/US2015/040709
§ 371 (c)(1),
(2) Date: Jan. 13, 2017

(87) PCT Pub. No.: WO2016/011231
PCT Pub. Date: Jan. 21, 2016

(65) Prior Publication Data
US 2017/0210766 A1 Jul. 27, 2017

Related U.S. Application Data

(60) Provisional application No. 62/025,328, filed on Jul. 16, 2014.

(51) Int. Cl.
| | |
|---|---|
| *C07D 213/127* | (2006.01) |
| *C07D 413/04* | (2006.01) |
| *C07F 7/18* | (2006.01) |
| *C07F 7/20* | (2006.01) |
| *C07C 41/30* | (2006.01) |
| *C07B 37/04* | (2006.01) |
| *C07B 43/00* | (2006.01) |
| *C07D 295/023* | (2006.01) |
| *C07C 253/30* | (2006.01) |
| *C07C 1/32* | (2006.01) |

(52) U.S. Cl.
CPC ............ *C07F 7/1844* (2013.01); *C07B 37/04* (2013.01); *C07B 43/00* (2013.01); *C07C 1/328* (2013.01); *C07C 41/30* (2013.01); *C07C 253/30* (2013.01); *C07D 295/023* (2013.01); *C07F 7/20* (2013.01); *C07C 2531/22* (2013.01)

(58) Field of Classification Search
CPC ...... C07D 213/127; C07D 413/04; C07F 7/18
USPC ............................. 546/339, 271.7; 556/464
See application file for complete search history.

(56) References Cited

U.S. PATENT DOCUMENTS

| | | | |
|---|---|---|---|
| 4,447,628 A | 5/1984 | Farnham | |
| 9,499,660 B2 * | 11/2016 | Hoye | C07F 7/1852 |
| 2008/0177112 A1 | 7/2008 | Tanaka et al. | |
| 2009/0069577 A1 | 3/2009 | Nakao et al. | |

FOREIGN PATENT DOCUMENTS

| | | | |
|---|---|---|---|
| WO | WO 2013/159229 A1 | 10/2013 | |
| WO | WO 2013/185021 A2 * | 12/2013 | C07F 7/08 |

OTHER PUBLICATIONS

Nguyen, M. H. et al.: Recyclable polystyrene-supported siloxane-transfer agent for palladium-catalyzed cross-coupling reactions. Organic Letters, vol. 16, pp. 2070-2073, 2014.*
Nguyen, M. H. et al.: Polymer-supported siloxane transfer agents for Pd-catalyzed cross-coupling reactions. Organic Letters, vol. 15, pp. 4258-4261, 2013.*
Martinez-Solorio, D. et al.: The design, synthesis and validation of recoverable and readily reusable siloxane transfer agents for Pd-catalyzed cross-coupling reactions. Organic Letters, vol. 15, pp. 2454-2457, 2013.*
Bastug et al, "Highly Chemoselective Reduction of Carbonyl Groups in the Presence of Aldehydes", Org. Lett., Mar. 2012, 14(5), 1306-1309.
Denmark et al., "Fluoride-Free Cross-Coupling of Organosilanols", J. Am. Chem. Soc., 2001, 123, 6439-6440.
Fleming et al., "The Phenyldimethylsilyl Group as a Masked Form of the Hydroxy Group", J. Chem. Soc. Chem. Commun., Jan. 1, 1984, 29-31.
Handy et al. "Recent Advances in Siloxane-Based Aryl-Aryl Coupling Reactions: Focus on 28-35 Heteroaromatic Systems",Tetrahedron, Sep. 8, 2005, 61(744), 12201-12225.
Harrowven et al, "Intramolecular Radical Additions to Pyridines", Org. Biomol. Chem., Oct. 13, 2003, 1(22), 4047-4057.
Huang et al., "A Convenient and Genuine Equivalent to HZrCp2Cl Generated in Situ from ZrCp2Cl2-DIBAL-H", Org. Lett., Jul. 27, 2006, 8(17), 3675-3678.
International Patent Application No. PCT/US13/44689: International Search Report and The Written Opinion dated Dec. 2, 2013, 17 pages.
Kobayashi et al, "Cp(2)Ni-KOt-Bu-BEt(3) (or PPh(3)) Catalyst System for Direct C—H Arylation of Benzene, Naphthalene, and Pyridine", Org. Lett., May 19, 2009, 11(12), 2679-2682.

(Continued)

*Primary Examiner* — Charanjit Aulakh
(74) *Attorney, Agent, or Firm* — Baker & Hostetler LLP

(57) ABSTRACT

Compositions and methods using silicon-based cross-coupling agents in the formation of carbon-carbon and carbon-nitrogen bonds are described.

16 Claims, No Drawings

(56) References Cited

OTHER PUBLICATIONS

Kunai et al.., "Selective Synthesis of Halosilanes From Hydrosilanes and Utilization for Organic Synthesis", J. Orgnomet. Chem., Nov. 21, 2003, 686(1-2), 3-15.

Kunai et al, "Highly Selective Synthesis of Chlorosilanes From Hydrosilanes", Organometallics, Jul. 1992, 11(7), 2708-2711.

Lin et al., "Cationic Pd(II)/Bipyridine-Catalyzed Addition of Arylboronic Acids to Arylaldehydes. One-Pot Synthesis of Unsymmetrical Triarylmethanes", J. Org. Chem., Nov. 14, 2007, 72(25), 9757-9760.

Manolikakes et al., "Radical Catalysis of Kumada Cross-Coupling Reactions Using Functionalized Grignard Reagents", Angelv. Chem. Int. Ed. , Dec. 3, 2008, 48(1), 205-209.

Nakao et al, "Alkenyl- and Aryl[2-(hydroxymethyl)phenyl]dimethylsilanes: An Entry to Tetraorganosilicon Reagents for the Silicon-Based Cross-Coupling Reaction", J. Am. Chem. Soc. Apr. 21, 2005, 127(19), 6952-6953.

Nakao, et al, "Cross-coupling reactions through the intramolecular activation of alkyl(triorgano)silanes", Angew. Chem. Int. Ed., Jun. 14, 2010, 49(26), 4447-4450.

Nakao, et al, "Synthesis and Cross-Coupling Reaction of Alkenyl[(2-Hydroxymethyl)Phenyl]Dimethylsilanes", Organomet. Chem., Jan. 1, 2007, 692(1-3), 585-603.

Seki et al., "Synthesis of (−)-Cytoxazone, a Novel Cytokine Modulator Isolated from *Streptomyces* sp.", Eur. J. Org. Chem., Nov. 1999, (11), 2965-1967.

Simmons et al, "Iridium-catalyzed Arene ortho-Silylation by Formal Hydroxyl-directed C—H Activation", J. Am. Chem. Soc., Dec. 8, 2010, 132(148), 17092-17095.

Smith et al, "Anion Relay Chemistry: Access to the Type II ARC Reaction Manifold through a Fundamentally Different Reaction Pathway Exploiting 1-Oxa-2-silacyclopentanes and Related Congeners", Chem. Int. Ed., Sep. 12, 2011, 50(38), 8904-8907.

Smith, "Unification of Anion Relay Chemistry (ARC) with the Takeda and Hiyama Cross-Coupling Reactions: Identification of an Effective Silicon-Based Transfer Agent", J. Am. Chem. Soc., 2012, 134(10), 4533-4536.

Son et al., "Functional Group Compatible Palladium-Catalyzed Cross-Coupling Reactions between Aryllithium and Aryl Halide Mediated by a Five-Membered Cyclic Silyl Ether", Bull. Chem. Soc. Jpn., Mar. 8, 2006, 79(3), 492-494.

Spino et al, "A Chiral Cyclohexanone Linked to Polystyrene for Solid-Phase Synthesis of Chiral Alpha-Carbonyls", J. Comb. Chem. Mar.-Apr. 2005, 7(2), 345.

Surry et al. "Biaryl Phosphineligands in Palladium-Catalyzed Amination", Angew Chem. Int. Ed. Engl., 2008, 47(34), 6338-6361.

Tamao, et al. "Hydrogen Peroxide Oxidation of the Silicon-Carbon Bond in Organoalkoxysilanes", Organometallics, Nov. 1983, 2(11), 1694-1696.

Wagner et al., "Deactivation of Triplet Phenyl Alkyl Ketones by Conjugatively Electron-Withdrawing Substituents", J. Am. Chem. Soc, Dec. 1981, 103(24), 7329-7335.

Wang et al., "Palladium Catalyzed Cross-Coupling of (Z)-1-Heptenyldimethylsilanol With 4-Iodoanisole: (Z)-1-Heptenyl-4-Methoxybenzene", Org. Synth., 2005, 81, 42.

* cited by examiner

SILICON-BASED CROSS COUPLING AGENTS AND METHODS OF THEIR USE

CROSS REFERENCE TO RELATED APPLICATIONS

This application is a National Stage Application filed under 35 U.S.C. 371 of International Application No. PCT/US2015/040709, filed Jul. 16, 2015, which claims the benefit of U.S. Provisional Application No. 62/025,328, filed Jul. 16, 2014, the entirety of which is incorporated by reference herein.

This application is related to International Application No. PCT/US2013/044689, filed Jun. 7, 2013, which claims the benefit of U.S. Provisional Application No. 61/657,309, filed Jun. 8, 2012 and U.S. Provisional Application No. 61/807,192, filed Apr. 1, 2013, the entireties of which are incorporated by reference herein.

GOVERNMENT RIGHTS

This invention was made with government support under Contract No. GM 29028 awarded by the National Institutes of Health. The government has certain rights in the invention.

TECHNICAL FIELD

The present invention is directed to silicon-based cross-coupling agents and methods of using them in cross-coupling reactions.

BACKGROUND

Cross-coupling reactions ("CCRs") of organometallic/main group reagents with, for example, organic halides permit the construction of carbon-carbon and carbon-nitrogen bonds. Although CCRs are atom-efficient processes, the known CCRs have drawbacks, including the undesired formation of homo-coupled products and the use of toxic metals. As such, new methods for the cross coupling of organic compounds to form new carbon-carbon bonds and new carbon-nitrogen bonds are needed.

SUMMARY

The present disclosure is directed to method of cross-coupling a compound of formula NuLi with a compound of formula E-X to form a compound of formula Nu-E comprising contacting the compound of formula NuLi with the compound of formula E-X in the presence of a catalyst system, an ethereal solvent, and a compound of Formula I

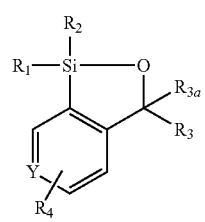

(I)

wherein
Y is CH or N;
$R_1$ and $R_2$ are independently $C_{1-10}$ straight or branched-chain alkyl optionally substituted with one or more halogen, nitro, $C_{1-6}$alkoxy, or aryl;
$R_3$ is H;
  aryl optionally substituted with one or more nitro, $diC_{1-6}$alkylamino, $C_{1-6}$alkoxy, or $C_{1-6}$alkyl;
  heteroaryl optionally substituted with one or more nitro, $diC_{1-6}$alkylamino, $C_{1-6}$alkoxy, or $C_{1-6}$alkyl;
  $C_{1-10}$ straight or branched-chain alkyl optionally substituted with one or more halogen, nitro, $C_{1-6}$alkoxy, or aryl;
  a polymer; or
  a resin support;
$R_{3a}$ is H or $C_{1-6}$alkyl optionally substituted with one or more halogen; and
at least one $R_4$, wherein each $R_4$ is independently hydrogen, halogen, nitro, $C_{1-6}$alkoxy, $C_{1-6}$alkyl, aryl, or a resin support;
for a time and under conditions sufficient to produce the compound of formula Nu-E;
wherein
Nu is an aryl compound, a heteroaryl compound, or an alkenyl compound;
E is an aryl compound, a heteroaryl compound, or an alkenyl compound; and
X is iodo, chloro, or bromo.

Compounds of formula I are also described.

DETAILED DESCRIPTION OF ILLUSTRATIVE EMBODIMENTS

The present invention is directed to compounds of formula I for use as silicon-based cross-coupling agents in the formation of carbon-carbon and carbon-nitrogen bonds:

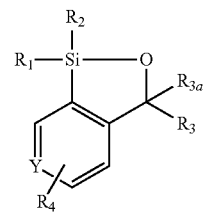

I wherein
Y is CH or N;
$R_1$ and $R_2$ are independently $C_{1-10}$ straight or branched-chain alkyl optionally substituted with one or more halogen, nitro, $C_{1-6}$alkoxy, or aryl;
$R_3$ is H;
  aryl optionally substituted with one or more halogen, nitro, $diC_{1-6}$alkylamino, $C_{1-6}$alkoxy, or $C_{1-6}$alkyl;
  heteroaryl optionally substituted with one or more halogen, nitro, $diC_{1-6}$alkylamino, $C_{1-6}$alkoxy, or $C_{1-6}$alkyl;
  $C_{1-10}$ straight or branched-chain alkyl optionally substituted with one or more halogen, nitro, $C_{1-6}$alkoxy, or aryl;
  a polymer; or
  a resin support;
$R_{3a}$ is H or $C_{1-6}$alkyl optionally substituted with one or more halogen; and at least one $R_4$, wherein each $R_4$ is independently hydrogen, halogen, nitro, $C_{1-6}$alkoxy, $C_{1-6}$alkyl, aryl, or a resin support.

In some embodiments of the invention, the compound of formula I is not

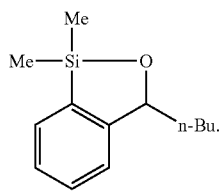

Compounds of formula I may comprise asymmetrically-substituted carbon atoms, i.e., chiral centers. These compounds may exist, without limitation, as single stereoisomers (for example, single enantiomers), mixtures of stereoisomers (for example, mixture of enantiomers), or racemic mixtures. Compounds identified herein as single stereoisomers are meant to describe compounds that are present in a form that is substantially free from other stereoisomers (e.g., substantially free from other enantiomers). By "substantially free," it means that at least 80% of the compound in a composition is the described stereoisomer; preferably, at least 90% of the compound in a composition is the described stereoisomer; and more preferably, at least 95%, 96%, 97%, 98% or 99% of the compound in a composition is the described stereoisomer.

The reactivity of the compound of formula I can be attenuated by manipulation of $R_1$ and $R_2$. For example, in preferred embodiments, $R_1$ and $R_2$ are independently methyl, ethyl, n-propyl, or isopropyl. Preferably, $R_1$ and $R_2$ are independently methyl or isopropyl. In exemplary embodiments, $R_1$ and $R_2$ are each methyl. In other embodiments, $R_1$ and $R_2$ are each isopropyl. In still other embodiments, $R_1$ and $R_2$ are each ethyl. In yet other embodiment, $R_1$ and $R_2$ can be optionally substituted with one or more halogen, nitro, $C_{1-6}$alkoxy, or aryl.

The reactivity of the compound of formula I can be attenuated by manipulation of $R_3$. For example, in some embodiments, $R_3$ is $C_{1-10}$, preferably $C_{1-6}$, straight or branched-chain alkyl optionally substituted with one or more halogen or $C_{1-6}$alkoxy. Preferably, $R_3$ is $C_{1-4}$ straight or branched-chain alkyl optionally substituted with one or more halogen or $C_{1-6}$alkoxy. More preferably, $R_3$ is $C_{1-4}$ straight or branched-chain alkyl. In exemplary embodiments, $R_3$ is n-butyl, isobutyl, sec-butyl, or tert-butyl. In most preferred embodiments, $R_3$ is n-butyl. In those embodiments wherein $R_3$ is $C_{1-6}$alkyl substituted with one or more halogen, $R_3$ is preferably $CF_3$.

In other embodiments, $R_3$ is aryl, preferably phenyl, optionally substituted with one or more halogen, nitro, $diC_{1-6}$alkylamino, $C_{1-6}$alkoxy, or $C_{1-6}$alkyl. Preferably, $R_3$ is phenyl optionally substituted with one or more $diC_{1-6}$alkylamino, $C_{1-6}$alkoxy, or $C_{1-6}$alkyl. In exemplary embodiments, $R_3$ is unsubstituted phenyl.

In still other embodiments, $R_3$ is heteroaryl, preferably pyridyl, optionally substituted with one or more halogen, nitro, $diC_{1-6}$alkylamino, $C_{1-6}$alkoxy, or $C_{1-6}$alkyl. Preferably, $R_3$ is pyridyl optionally substituted with one or more $diC_{1-6}$alkylamino, $C_{1-6}$alkoxy, or $C_{1-6}$alkyl. In exemplary embodiments, $R_3$ is unsubstituted pyridyl.

In other preferred embodiments, $R_3$ is a polymer. Preferably, this polymer acts as a solid support for the siloxane transfer agent. Such polymers are known in the art per se. Preferred polymers are described herein.

In still other embodiments, $R_3$ is a resin support.

In preferred embodiments of the invention, $R_{3a}$ is H or $C_{1-6}$alkyl optionally substituted with one or more halogen. Preferably, $R_{3a}$ is H. In those embodiments wherein $R_{3a}$ is $C_{1-6}$alkyl, exemplary moieties include methyl and ethyl. In other embodiments wherein $R_{3a}$ is $C_{1-6}$alkyl substituted with one or more halogen, $R_{3a}$ is preferably $CF_3$.

The reactivity of the compound of formula I can be attenuated by manipulation of $R_4$. The compounds of formula I can include one, two, three, or four $R_4$ groups, which can each be the same or different. $R_4$ is preferably hydrogen, halogen, nitro, $C_{1-6}$alkoxy, $C_{1-6}$alkyl, or aryl. More preferably, $R_4$ is hydrogen, halogen, for example F, $C_{1-6}$alkoxy, or $C_{1-6}$alkyl. In exemplary embodiments, $R_4$ is hydrogen. In other embodiments, $R_4$ is halogen, for example, F, Cl, or Br, with F being particularly preferred. $R_4$ can also be a resin support.

In those embodiments wherein the compound of formula I include a resin support, the resin support is at either $R_3$ or $R_4$. That is, in certain embodiments wherein $R_3$ is a resin support, each $R_4$ is independently hydrogen, halogen, nitro, $C_{1-6}$alkoxy, $C_{1-6}$alkyl, or aryl. In those embodiments wherein $R_4$ is a resin support, $R_3$ is H; aryl optionally substituted with one or more halogen, nitro, $diC_{1-6}$alkylamino, $C_{1-6}$alkoxy, or $C_{1-6}$alkyl; heteroaryl optionally substituted with one or more halogen, nitro, $diC_{1-6}$alkylamino, $C_{1-6}$alkoxy, or $C_{1-6}$alkyl; $C_{1-10}$ straight or branched-chain alkyl optionally substituted with one or more halogen, nitro, $C_{1-6}$alkoxy, or aryl; or a polymer.

It is preferred that the aromatic moiety of the compounds of formula I is phenyl, that is, wherein Y is CH or $CR_4$. In such embodiments, preferred compounds of formula I include, for example:

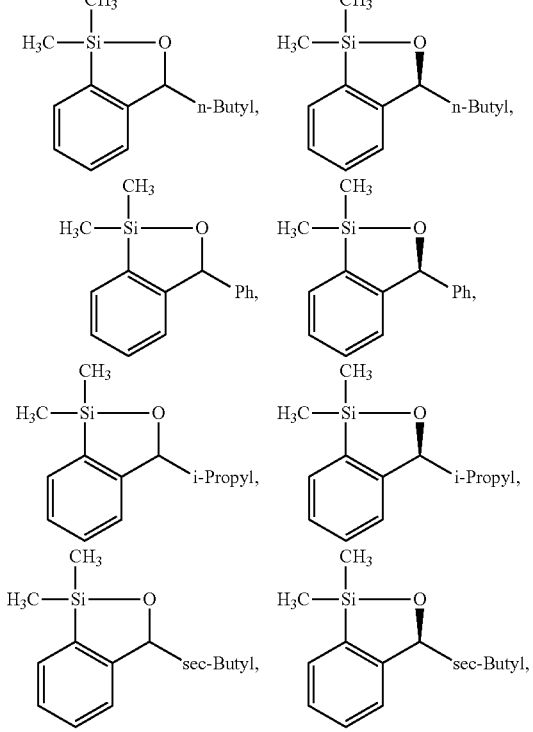

-continued
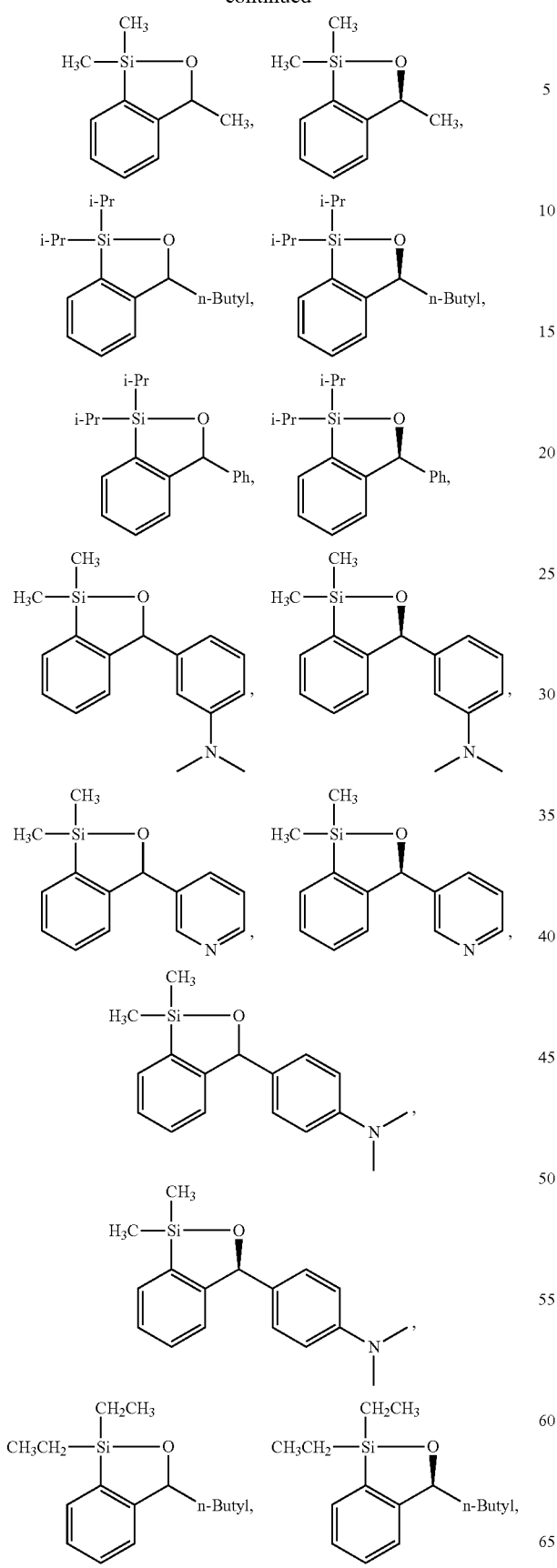
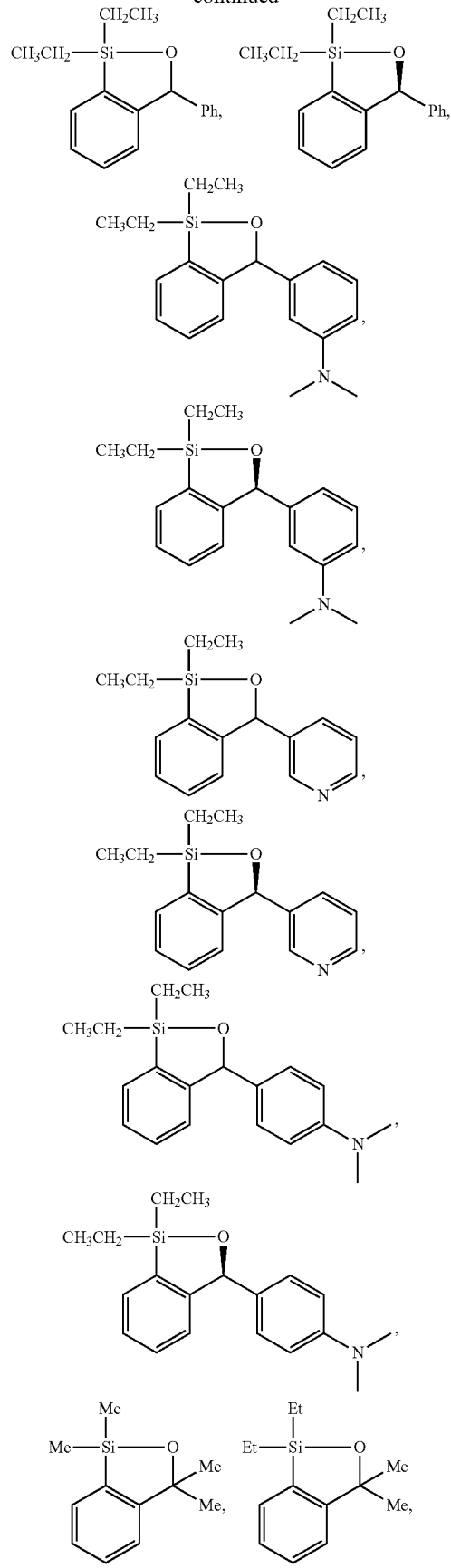

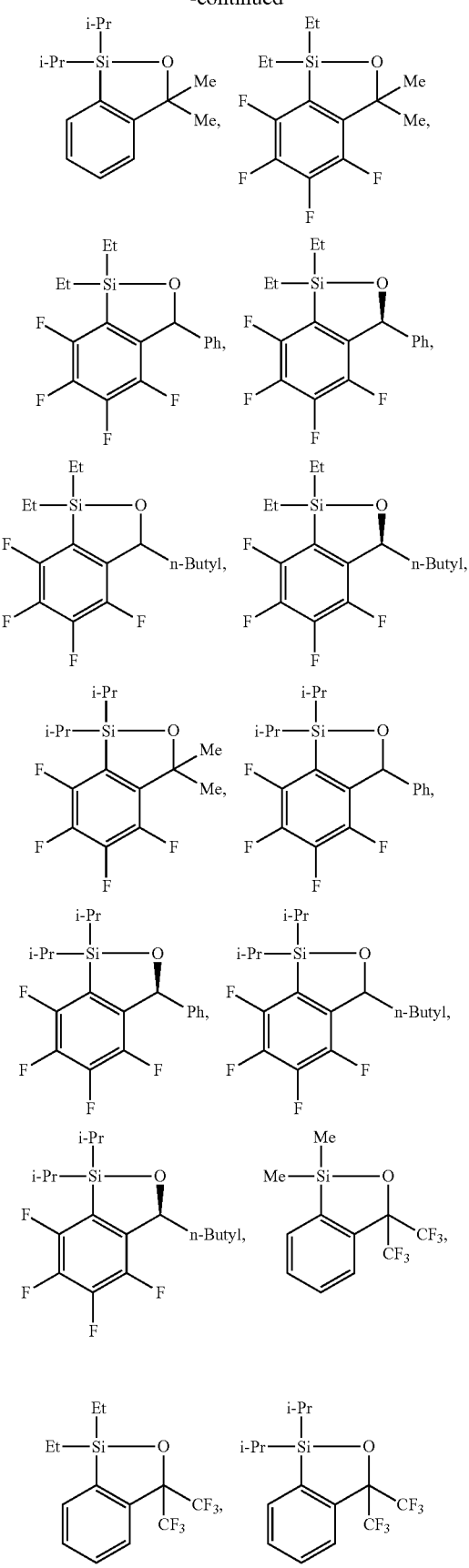
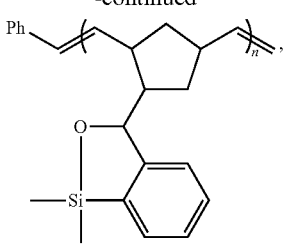
wherein n is about 150 to about 300, preferably about 200 or 250,
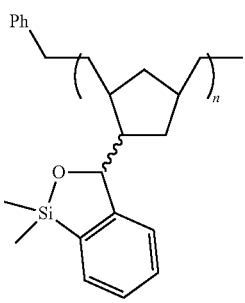
n = 20 to 200
"polymer-supported siloxane transfer agent (saturated),"
for example, having 20 to 200 repeating units,
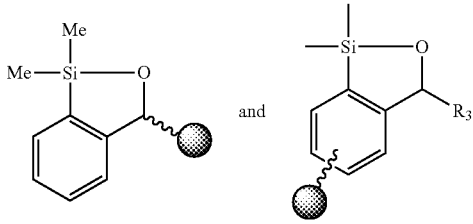
"resin-supported siloxane transfer agent."
Exemplary embodiments of the invention wherein $R_3$ is a polymer include compounds of the formula:
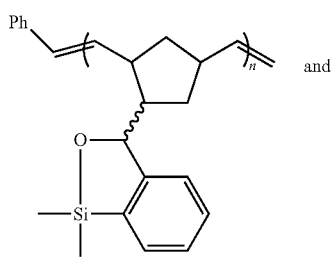
and

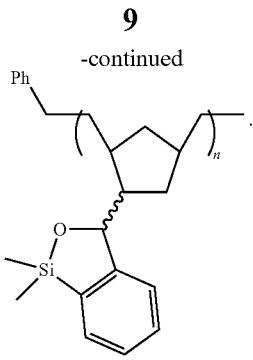

wherein n is independently about 20 to 300, preferably 20 to 200, or 150 to about 300. Most preferably, n is about 200 or 250.

Exemplary embodiments of the invention wherein $R_3$ or $R_4$ is a resin support include:

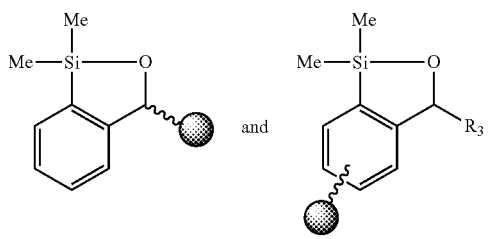

In other embodiments, the aromatic moiety of the compounds of formula I is pyridyl, that is, wherein Y is N.

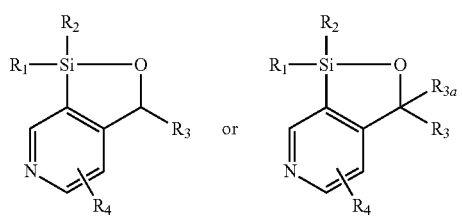

Exemplary embodiments of the invention wherein Y is N are:

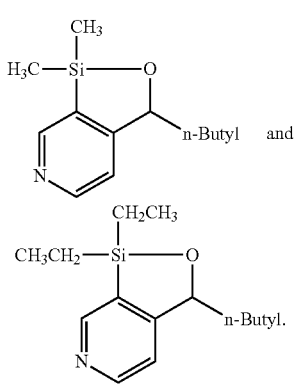

Based on its physico-chemical properties, a compound of formula I including a pyridyl group may facilitate removal of the cross-coupling transfer agent from the products of the cross-coupling reaction mixture by treatment of the crude reaction mixture with Brønsted or Lewis acids upon workup.

In accordance to the present invention, and as described above and below, the siloxane motif maybe incorporated into polymers using monomers derived from the silicon transfer agent. This polymeric material may improve the ease of purification following the cross-coupling reaction, and may make the transfer agent easier to handle by altering its physical properties.

The invention is also directed to methods of cross-coupling compounds of formula NuLi with a compound of formula E-X to form a compound of formula Nu-E. These methods comprise contacting the compound of formula NuLi with the compound of formula E-X in the presence of a siloxane compound of the invention as described herein, a catalyst or a catalyst system, and an ethereal solvent, for a time and under conditions sufficient to produce the compound of formula Nu-E. In these methods, Nu is an aryl compound or an alkenyl compound; E is an aryl compound or an alkenyl compound; and X is iodo or bromo or X is iodo, chloro, or bromo.

The invention is also directed to methods of cross-coupling compounds of formula Nu-Li with a compound of formula E-X to form a compound of formula Nu-E. These methods comprise contacting the compound of formula NuLi with the compound of formula E-x in the presence of a siloxane compound of the invention as described herein, a catalyst or a catalyst system, and an ethereal solvent, for a time and under conditions sufficient to produce the compound of formula Nu-E. In these methods, Nu is an aryl compound or an alkeneyl compound; E is a disubstituted amine, and X is —O-benzoyl.

As used herein, "aryl compound" refers to an organic compound comprising a phenyl or naphthyl group that is optionally substituted with one or more substitutents. Examples of substitutents include alkyl, aryl, halogen, nitro, cyano, keto, ester, alkoxy, siloxy, and the like.

As used herein, "alkenyl compound" refers to an organic compound comprising a carbon-carbon double bond that is optionally substituted with one or more substitutents. Examples of substitutents include alkyl, aryl, halogen, nitro, cyano, ester, alkoxy, siloxy, and the like.

As used herein, "$C_{1-10}$ straight or branched-chain alkyl" refers to an aliphatic hydrocarbon including from 1 to 10 carbon atoms. Examples include methyl, ethyl, n-propyl, iso-propyl, n-butyl, iso-butyl, tert-butyl, n-penyl, iso-pentyl, n-hexyl, and the like.

As used herein, "di$C_{1-6}$alkylamino" refers to an amino moiety substituted with two $C_{1-6}$alkyl group. The $C_{1-6}$alkyl groups can be the same or different. Preferred di$C_{1-6}$alkylamino groups for use in the invention include dimethylamino, diethylamino, methylethylamino, diisopropylamino, and the like.

As used herein, "disubstituted amine" refers to a nitrogen atom having two substituents, which are the same or different. Disubstituted amine also refers to compounds wherein the two substituents are joined to form a ring. Examples of disubstituted amines include $(Bn)_2N$—, $(Et)_2N$—,

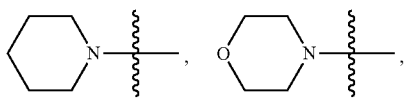

and the like.

As used herein, "aryl" refers to an aromatic 6-13 membered mono- or bi-cyclic ring such as phenyl or naphthyl.

As used herein, "halogen" refers to iodo, bromo, chloro, or fluoro.

As used herein, "heteroaryl" refers to a mono- or bicyclic aromatic ring structure including carbon atoms as well as up to four heteroatoms selected from nitrogen, oxygen, and sulfur. Heteroaryl rings can include a total of 5, 6, 9, or 10 ring atoms. Preferred heteroaryl groups include pyridyl and pyrimidinyl.

As used herein, "heteroaryl compound" refers to a heteroaryl moiety that is optionally substituted with one or more substitutents. Examples of substitutents include alkyl, aryl, halogen, nitro, cyano, keto, ester, alkoxy, siloxy, and the like.

As used herein, "resin support" refers to solid supports used in, for example, combinatorial chemistry. "Wang resins" and "Merrifield resin" are examples of such resins. Resin supports and their use and incorporation are known to those skilled in the art, per se.

The compounds of formula I can be used in organic synthesis, most preferably as silicon-based cross-coupling agents. In exemplary embodiments, the compound of formula I is used in the presence of, for example, an organo-lithium compound and an organo-halogen (or an organo-pseudohalogen) compound to form the resulting cross-coupled organic compound. See, e.g., Scheme 1 for an example using one embodiment of the invention. Preferably, the organo-lithium compound is an aryl-lithium or alkenyl-lithium compound. The organo-halogen compound is preferably an aryl-halogen compound or an alkenyl-halogen compound. In such embodiments, the halogen is preferably iodo, chloro, or bromo. In those embodiments employing an organo-pseudohalogen, the pseudohalogen is, for example, triflate or mesylate). The resulting cross-coupled organic compounds are thus aryl-aryl compounds, aryl-alkenyl, or alkenyl-alkenyl compounds. Alternatively, the compounds of formula I can be used in the presence of, for example, an organomagnesium reagent (i.e., "Grignard reagents").

compared to either the organo-lithium or organo-halogen compound. In such embodiments, up to three molar equivalents of the compound of formula I, as compared to either the organo-lithium or organo-halogen compound, can be used. Within the scope of the invention, it is envisioned that 1.1, 1.2, 1.3, 1.4, 1.5, 1.6, 1.8, 2.0, 2.2, 2.5, or 2.8 molar equivalents of the compound of formula I, as compared to either the organo-lithium or organo-halogen compound, can be used. It is preferred to use 1.6, 1.8, or 2.0 molar equivalents of the compound of formula I. Also preferred is the use of 1.3 or 1.1 molar equivalents of the compound of formula I. In some embodiments, 1.8 molar equivalents of the compound of formula I is used. The amount of the compound of formula I required for cross-coupling a particular organo-lithium compound with a particular organo-halogen compound can be determined without undue experimentation by someone of skill in the art.

Alternatively, the compound of formula I can be used in catalytic amounts, that is, less than one molar equivalent, as compared to either the organo-lithium or organo-halogen compound. In some embodiments, the compound of formula I is present at from 1 mol % to 90 mol %, for example, 10, 20, 30, 40, 50, 60, 70, 80, or 90 mol %.

In some embodiments, cross-coupling of an organo-lithium compound with an organo-halogen compound in the presence of the silicon-based cross-coupling agent compounds of formula I of the invention requires the use of a catalyst or catalyst system. Preferred catalysts or catalyst systems comprise palladium compounds, copper compounds, nickel compounds, or mixtures thereof, optionally in the presence of a phosphate ligand such as cyclohexyl-(2-diphenylphosphanyl-benzylidene)-amine (dpca), XPhos (2-dicyclohexylphosphino-2',4',6'-triisopropylbiphenyl), Johnphos ((2-biphenyl)di-tert-butylphosphine), DavePhos (2-Dicyclohexylphosphino-2'-(N,N-dimethylamino)biphenyl), or SPhos (2-Dicyclohexylphosphino-2',6'-dimethoxybiphenyl). Buchwald precatalysts, for example, Second, Third, and Fourth Generation Buchwald Precatalysts, can also be used with the methods of the disclosure:

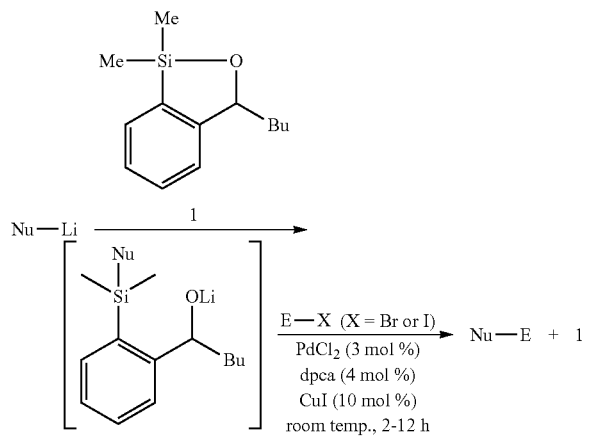

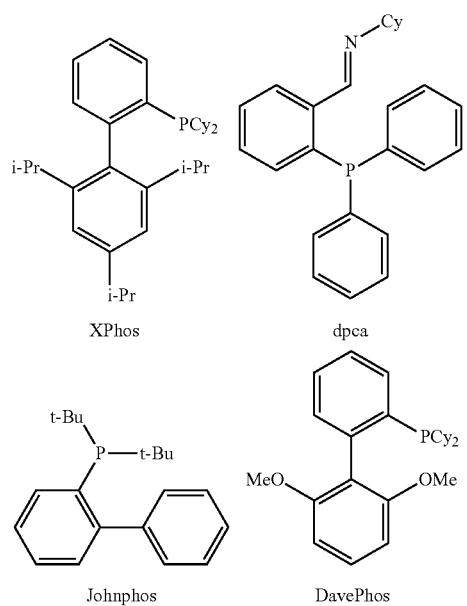

In such cross-coupling reactions, the compounds of formula I can be used in stoichiometric amounts, that is, one molar equivalent, as compared to either the organo-lithium or organo-halogen compound. In some embodiments, the compounds of formula I are used in greater than stoichiometric amounts, that is, greater than one molar equivalent as

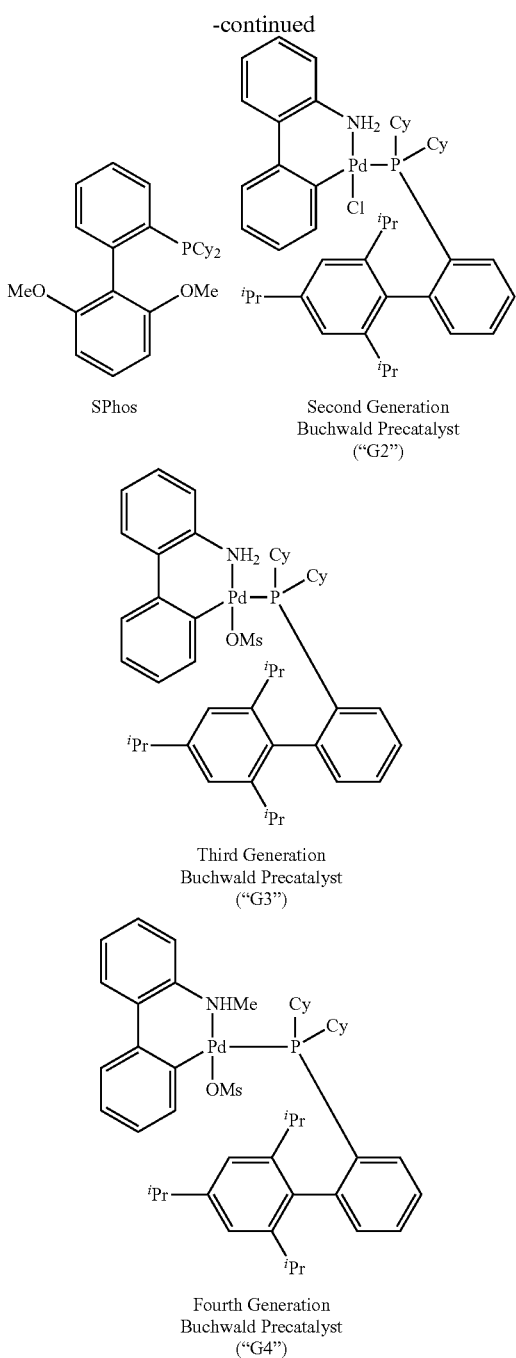

SPhos

Second Generation Buchwald Precatalyst ("G2")

Third Generation Buchwald Precatalyst ("G3")

Fourth Generation Buchwald Precatalyst ("G4")

Preferably, the palladium compound is $PdCl_2$, $Pd(PPh_3)_4$, or $Pd(OAc)_2$. The copper compound is preferably a copper halide, for example, CuI. A preferred catalyst system for use in the methods of the invention comprises $PdCl_2$, CuI, and dpca. Another preferred catalyst system includes $Pd(OAc)_2$ and a phosphate ligand such as XPhos. Yet another catalyst system includes CuI and dpca. Another catalyst system include CuI and Johnphos.

Those of skill in the art can readily determine the mole percentage of the catalyst or each component of the catalyst system for use in the methods of the invention. For example, the catalyst or component of the catalyst system can be present in an amount of from about 0.1 mol % to about 15 mol % or about 1 mol % to about 15 mol %. For example, the catalyst or component of the catalyst system can be present in an amount of about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or about 15 mol %. In some embodiments, the catalyst or component of the catalyst system can be present in an about of from about 0.5 mol % to about 5 mol %. Alternatively, the catalyst or component of the catalyst system can be present in an amount of from about 3 mol % to about 10 mol %.

In embodiments incorporating the use of a palladium compound as the catalyst or component of the catalyst system, the palladium compound is present in an amount of from about 0.5 mol % to about 5 mol % or about 1 mol % to about 5 mol % or to about 10 mol %. Preferably, the palladium compound, for example, $PdCl_2$, is present at about 3 mol %.

In embodiments incorporating the use of a copper compound as the catalyst or component of the catalyst system, the copper compound is present in an amount of from about 0.1 mol % to about 10 mol %. In other embodiments, the copper compound is present in an amount of from about 1 mol % to about 10 mol %. Alternatively, the copper compound is present in an amount of from about 5 mol % to about 12 mol %. More preferably, the copper compound is present in an amount of from about 9 mol % to about 11 mol %. Most preferably, for example when the copper compound is CuI, it is present at about 10 mol %.

In those embodiments incorporating dpca in the catalyst systems of the invention, the dpca is present from about 1 mol % to about 10 mol %. Preferably, the dpca is present in an amount from about 2 mol % to about 8 mol %. Particularly preferred are embodiments wherein the dpca is present at about 4 mol %. In those embodiments employing dpca, the dpca is used in conjunction with $PdCl_2$. Dpca can also be used in conjunction with CuI. Preferably, the dpca is present in an amount greater than the amount of $PdCl_2$ or CuI. For example, the dpca is present at about 4 mol % and the $PdCl_2$ is present at about 3 mol %.

In those embodiments incorporating a phosphate ligand such as XPhos, JohnPhos, DavePhos, or SPhos in the catalyst systems of the invention, the phosphate ligand is present from about 1 mol % to about 50 mol %. Preferably, the phosphate ligand is present in an amount from about 10 mol % to about 30 mol %. Particularly preferred are embodiments wherein the phosphate ligand is present at about 20 mol %.

In embodiments incorporating Johnphos in the catalyst systems of the invention, the Johnphos is present from about 1 mol % to about 20 mol %. Preferably, the XPhos is present in an amount from about 5 mol % to about 15 mol % or about 5 mol % to about 20 mol %. Particularly preferred are embodiments wherein the XPhos is present at about 20 mol % or 10 mol %.

Preferred solvents for use in the cross-coupling reactions of the invention include ethereal solvents, for example tetrahydrofuran (THF), tetrahydropyran (THP), diisopropyl ether and diethyl ether, with THF being particularly preferred.

The cross-coupling reactions of the disclosure can be performed at or below room temperature, i.e., at or below about 23° C. For example, cross-coupling reactions of the disclosure can be performed at about 23° C. or at between about 0° C. and 23° C. In other embodiments, the cross-coupling reactions of the disclosure can be performed at or above room temperature. For example, cross-coupling reactions of the disclosure can be performed at about 23° C. or at between about 23° C. and about 50° C., between about 23° C. and about 60° C., or between about 23° C. and about 70° C.

Siloxanes of the invention can be prepared according to the methods described herein. Two exemplary methods are shown in Schemes 2A and 2B. Other siloxanes within the scope of the invention can be prepared similarly.

Scheme 2

A. Two-Pot Synthesis of Siloxane 1 from Benzaldehyde.

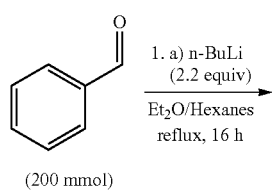
(200 mmol)

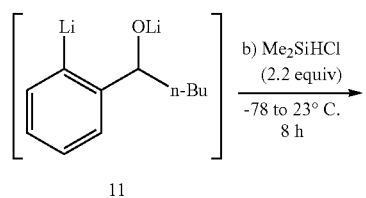
11

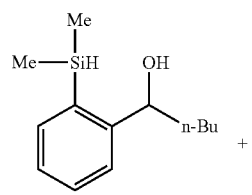
12

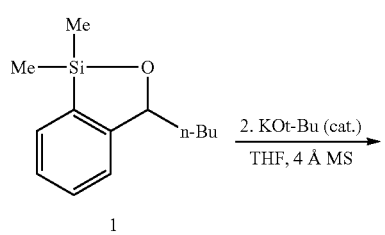
1

B. One-Pot Synthesis of Siloxane 2a from Benzaldehyde.

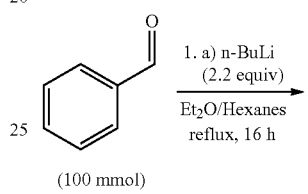
(100 mmol)

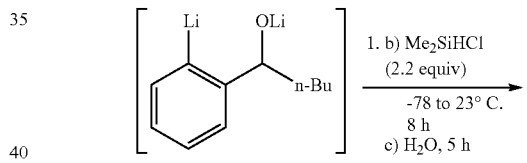
11

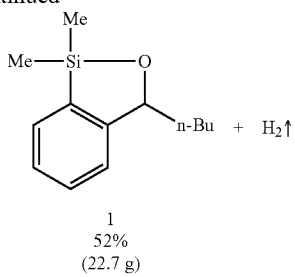
1
52%
(22.7 g)

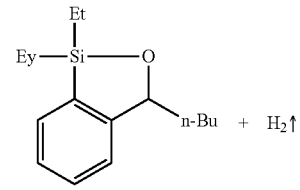
2a
53%
(6.2 g)

Substantially enantiomerically pure compounds are also within the scope of the disclosure. For example, compounds of the disclosure, having an ee of at least 90%, preferably at least 96% or 98% ee, can be prepared according to methods known in the art. A preferred method is set forth in the following Scheme 2A:

Scheme 2A
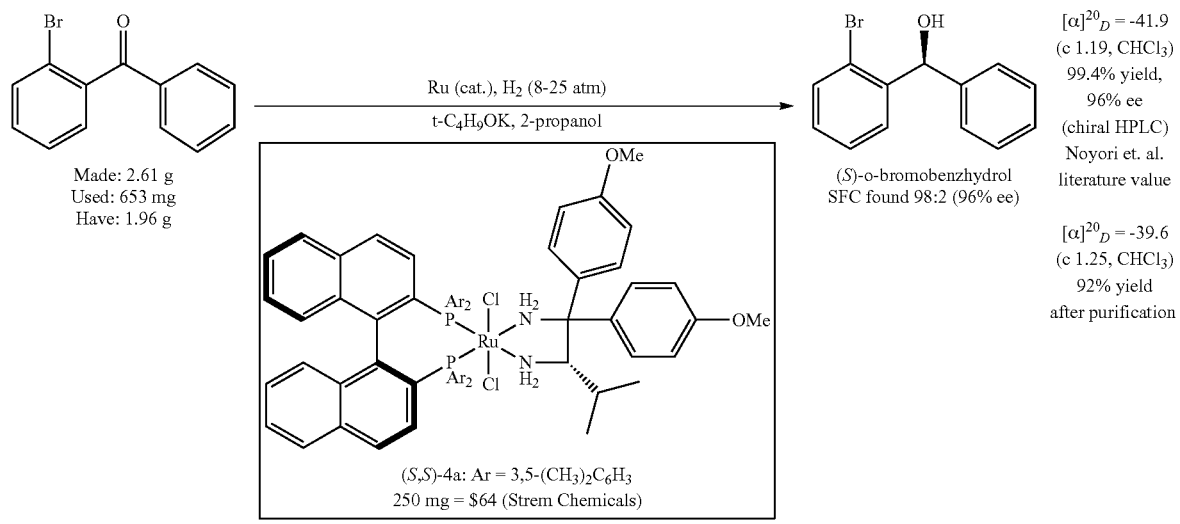
Noyori et. al. *Org. Lett.* 2000, 2, 659.
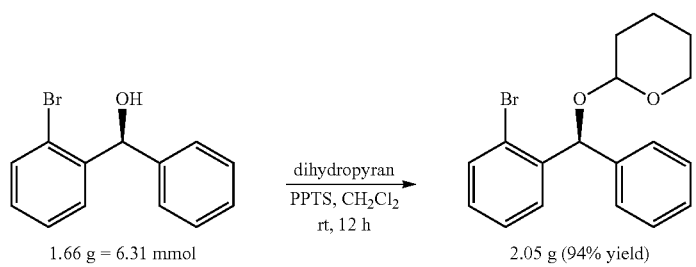
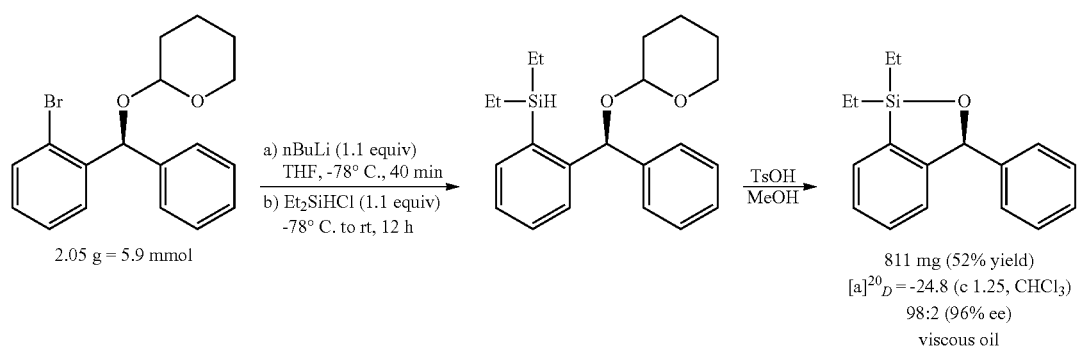

Preferred compounds of formula I have been successfully employed to cross-couple a variety of organo-lithium and organo-halogen compounds, while limiting the amount of homo-coupled product. For example, Scheme 3 depicts the results of several experiments where the organo-halogen compound was 4-iodoanisole and the organo-lithium compound was phenyl lithium.

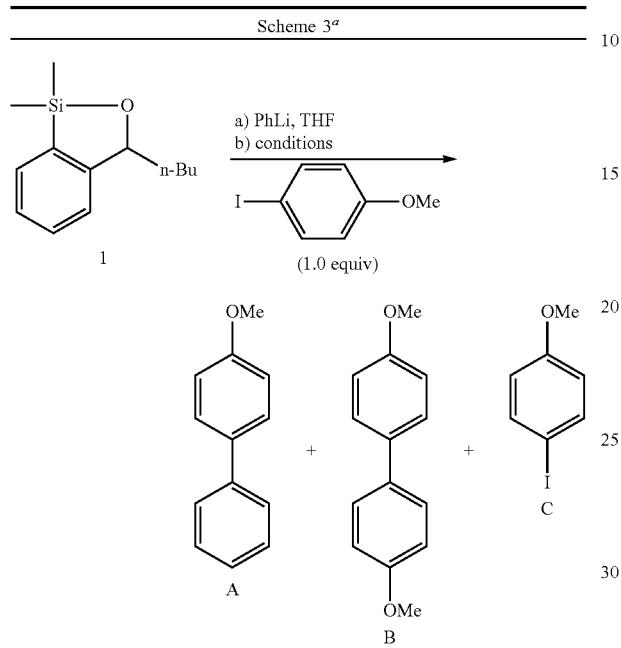

Scheme 3[a]

| Entry | Solvent | Equiv. 1 | Equiv. PhLi | Time (step a) | Time (step b) | ¹H NMR Results (A:B:C)[b] |
|---|---|---|---|---|---|---|
| 1 | THF | 2.0 | 2.1 | 0.5 h | 2 h | 13.4:1:nd |
| 2 | THF | 1.2 | 1.1 | 0.5 h | 0.5 h | 7.2:1.0:4.0 |
| 3 | THF | 1.6 | 1.5 | 1 h | 2 h | 17.8:1.0:2.2 |
| 4[c] | THF | 1.6 | 1.5 | 1 h | 2 h | >20:1.0:2.8 |
| 5[c] | THF | 2.0 | 1.5 | 1 h | 2 h | >20:nd:nd |
| 6[c] | THF | 2.0 | 1.2 | 1 h | 2 h | 3.4:nd:1.0 |
| 7[c] | THF | — | 1.5 | 1 h | 2 h | 2.5:0.6:1.0[d] |
| 8[c] | THF | 1.8 | 1.5 | 1 h | 2 h | >20:nd:nd |

[a]All reactions were performed on 0.45 mmol scale with 4-iodoanisole as the limiting reagent.
[b]determined by ¹H NMR analysis of the crude mixture of reaction products following aqueous workup and extraction with Et₂O. nd = not detected
[c]PdCl₂ (3 mol %), dpca (4 mol %), and CuI (10 mol %) were premixed for 30 minutes in THF prior to the addition of 4-iodoanisole, after which the PhLi and 1 reaction mixture was introduced via cannula.
[d]No 1-oxa-2-silacyclopentene was used in the reaction; a solution of PhLi in THF was used as a substitute.

Referring to Scheme 3, compound 1 is a compound of formula I within the scope of the invention. Good conversion of the aryl iodide occurred when steps a and b were allowed to proceed for longer times (see entry 3). A significant increase in the efficiency of the process was observed when the catalyst system of PdCl₂, dpca, and CuI was premixed for about 30 minutes in THF at room temperature prior to introduction of the aryl halide, which was followed by immediate addition of a mixture of PhLi and 1 in THF (see entry 4). Using this protocol in conjunction with the use of 2.0 molar equivalents of compound 1 led to complete conversion of 4-iodoanisole with no detectable homo-coupled product. Notably, significant homocoupling and catalyst decomposition was observed in the absence of silicon cross coupling agent 1 (see entry 7). The best results for these reagents, as shown in Scheme 3, resulted using 1.8 molar equivalents of compound 1 and 1.5 molar equivalents of PhLi.

As shown in Scheme 4, organo-halides other than 4-iodoanisole can be used in cross-coupling reactions of the invention using the silicon cross-coupling agents of the present invention, i.e., compounds of formula I.

Scheme 4

| Entry | Ar—X | Yield Ph—Ar[a] |
|---|---|---|
| 1 | 9a (I—C₆H₄—OMe) | 96% (10a) |
| 2 | 9b (I—C₆H₄—CN) | 92% (10b) |
| 3[b] | 9c (Br—C₆H₄—CN) | 92% (10b) |
| 4 | 9e (I—C₆H₄—CO₂Me) | 75% (10c) |
| 5 | 9f (2-I—C₆H₄—CO₂Me) | 76% (10d) |

| | | |
|---|---|---|
| 6 | 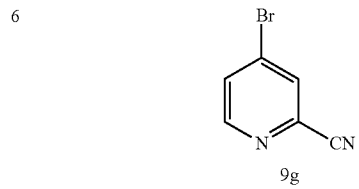

9g | 85% (10e) |
| 7[b] | 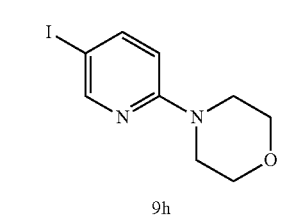 [SMILES: Ic1ccc(N2CCOCC2)nc1]

9h | 95% (10f) |

| | | |
|---|---|---|
| 8 | 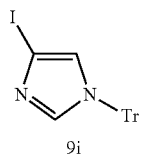

9i | 67% (10g) |

[a]Isolated yields.
[b]The reaction was allowed to proceed for 12 h following addition of the PhLi.

As demonstrated in Scheme 4, electron-rich and electron-deficient substrates were well-tolerated in the reaction, as were a variety of common functional groups, for example, ester, nitriles, and azoheterocycles, to provide the biaryl compounds 10a-g in good yields. In all cases, silicon cross-coupling agent 1, which is a compound of formula I of the invention, emerged from the reaction intact, as observed by $^1$H NMR analysis of the crude reaction mixtures. For products possessing polarities similar to that of compound 1, an oxidative Tamao-Fleming workup (Simmons, E. M. et al., J. Am. Chem. Soc. 2010, 132, 17092; Tamao, K. et al. Organometallics 1983, 2, 1694; Fleming, I. et al., J. Chem. Soc. Chem. Commun. 1984, 29) of the initial reaction mixture was used to convert 1 to the corresponding diol, which could be easily separated by column chromatography.

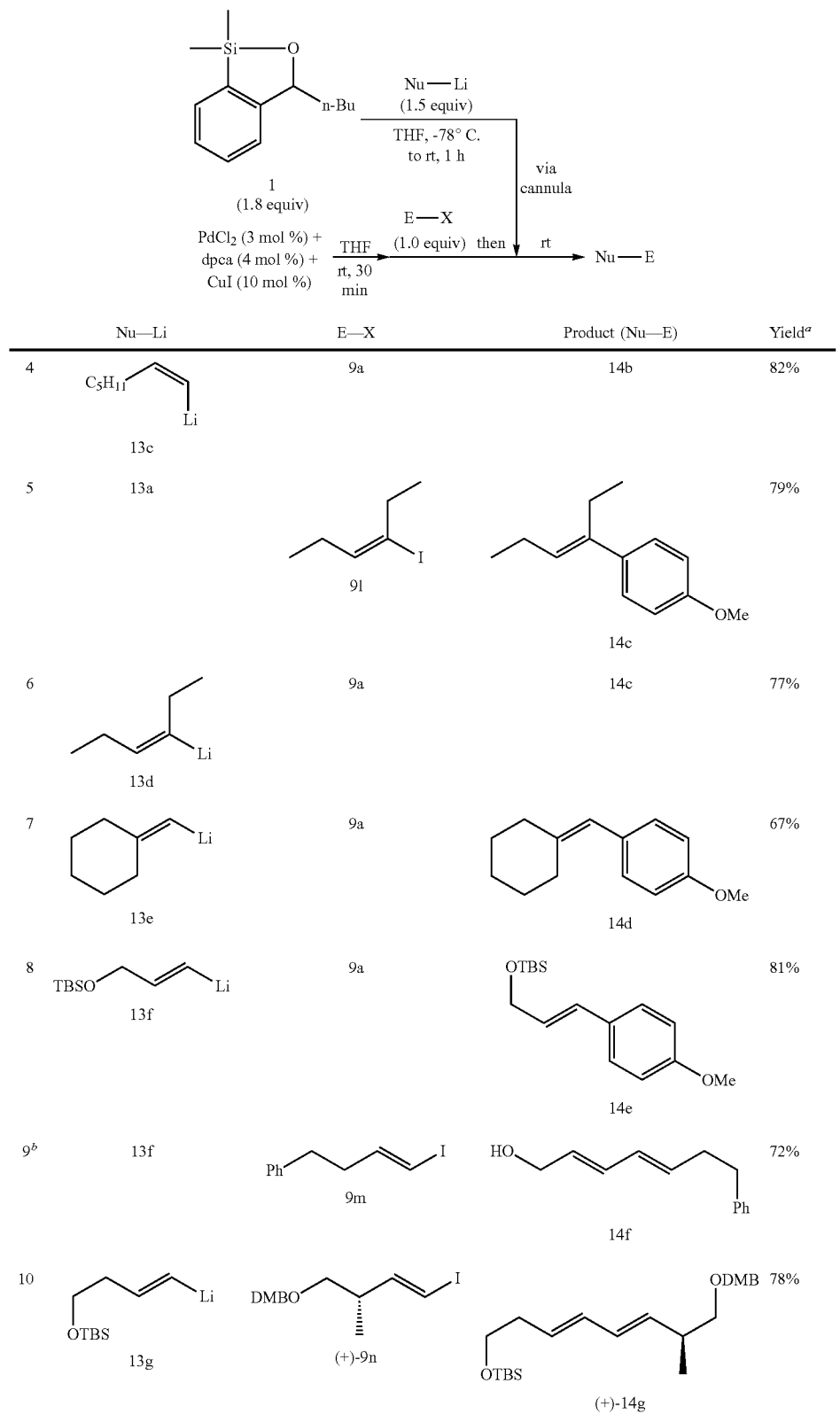

The methods of the claimed invention can also be extended to alkenyl substrates. As shown in Scheme 5 above, vinyl halides 9j-l were good coupling partners with 13a, forming styrenes 14a-c with retention of the alkene geometry (see entries 1, 3, and 5). Notably, the roles of the coupling partners could be reversed by using the corresponding vinyllithium and aryl halide to access identical coupling products in comparable yields (see entries 2, 4, and 6), demonstrating the flexibility of the methods of the invention with respect to the choice of nucleophilic and electrophilic components. Geminal and vicinal substitution patterns were tolerated in the cross coupling process from silicon, providing coupled products 14c and 14d. Also noteworthy was the successful vinyl-vinyl couplings of 13f and 9m and between 13g and (+)-9n to provide dienes 14f and (+)-14g.

Scheme 6 details examples demonstrating the scope and utility of the methods of the invention using preferred embodiments of compounds of formula I as silicon cross coupling agents.

Scheme 6

| Entry | Siloxane | Nu—Li | E—X | Catalyst System | Product | Isolated Yield |
|---|---|---|---|---|---|---|
| 1 | [siloxane with Me, Me-Si-O, n-Bu, phenyl ring] | PhLi | [diene with OMe and I] | PdCl$_2$ (3 mol %) dpca (4 mol %) CuI (10 mol %) | [diene with OMe and Ph] | 96% |
| 2 | [siloxane with Me, Me-Si-O, n-Bu, phenyl ring] | PhLi | [diene with CN and I] | PdCl$_2$ (3 mol %) dpca (4 mol %) CuI (10 mol %) | [diene with CN and Ph] | 92% |
| 3 | [siloxane with Me, Me-Si-O, n-Bu, phenyl ring] | PhLi | [diene with CN and Br] | PdCl$_2$ (3 mol %) dpca (4 mol %) CuI (10 mol %) | [diene with CN and Ph] | 92% |
| 4 | [siloxane with Me, Me-Si-O, n-Bu, phenyl ring] | PhLi | [diene with CO$_2$Me and I] | PdCl$_2$ (3 mol %) dpca (4 mol %) CuI (10 mol %) | [diene with CO$_2$Me and Ph] | 75% |
| 5 | [siloxane with Me, Me-Si-O, n-Bu, phenyl ring] | PhLi | [diene with MeO$_2$C and I] | PdCl$_2$ (3 mol %) dpca (4 mol %) CuI (10 mol %) | [diene with MeO$_2$C and Ph] | 76% |
| 6 | [siloxane with Me, Me-Si-O, n-Bu, phenyl ring] | PhLi | [pyridyl-diene with Br and CN] | PdCl$_2$ (3 mol %) dpca (4 mol %) CuI (10 mol %) | [pyridyl-diene with Ph and CN] | 85% |

-continued

Scheme 6

| Entry | Siloxane | Nu—Li | E—X | Catalyst System | Product | Isolated Yield |
|---|---|---|---|---|---|---|
| 7 | Me-Si(Me)-O-CH(n-Bu)-benzo (benzosiloxane with n-Bu) | PhLi | 1-iodo-2-(morpholinomethyleneamino)ethene | $PdCl_2$ (3 mol %) dpca (4 mol %) CuI (10 mol %) | Ph-substituted diene with morpholinomethyleneamino group | 95% |
| 8 | Me-Si(Me)-O-CH(n-Bu)-benzo | PhLi | 4-iodo-1-trityl-imidazole | $PdCl_2$ (3 mol %) dpca (4 mol %) CuI (10 mol %) | 4-phenyl-1-trityl-imidazole | 67% |
| 9 | Me-Si(Me)-O-CH(n-Bu)-benzo | 4-MeO-C$_6$H$_4$-Li | (E)-$C_5H_{11}$-CH=CH-Br | $PdCl_2$ (3 mol %) dpca (4 mol %) CuI (10 mol %) | (E)-$C_5H_{11}$-CH=CH-C$_6$H$_4$-OMe | 81% |
| 10 | Me-Si(Me)-O-CH(n-Bu)-benzo | 4-MeO-C$_6$H$_4$-Li | (Z)-$C_5H_{11}$-CH=CH-I | $PdCl_2$ (3 mol %) dpca (4 mol %) CuI (10 mol %) | (Z)-$H_{11}C_5$-CH=CH-C$_6$H$_4$-OMe | 82% |
| 11 | Me-Si(Me)-O-CH(n-Bu)-benzo | (E)-$C_5H_{11}$-CH=CH-Li | 4-iodoanisole | $PdCl_2$ (3 mol %) dpca (4 mol %) CuI (10 mol %) | (E)-$C_5H_{11}$-CH=CH-C$_6$H$_4$-OMe | 84% |
| 12 | Me-Si(Me)-O-CH(n-Bu)-benzo | (Z)-$C_5H_{11}$-CH=CH-Li | 4-iodoanisole | $PdCl_2$ (3 mol %) dpca (4 mol %) CuI (10 mol %) | (Z)-$H_{11}C_5$-CH=CH-C$_6$H$_4$-OMe | 82% |
| 13 | Me-Si(Me)-O-CH(n-Bu)-benzo | 4-MeO-C$_6$H$_4$-Li | (E)-3-iodo-3-hexene | $PdCl_2$ (3 mol %) dpca (4 mol %) CuI (10 mol %) | (E)-3-(4-methoxyphenyl)-3-hexene | 79% |

-continued

Scheme 6

| Entry | Siloxane | Nu—Li | E—X | Catalyst System | Product | Isolated Yield |
|---|---|---|---|---|---|---|
| 14 | Me-Si(Me)-O benzo, n-Bu | 2-pentenyl-Li | 4-iodoanisole | PdCl$_2$ (3 mol %) dpca (4 mol %) CuI (10 mol %) | (E)-2-ethyl-1-(4-methoxyphenyl)-1-butene | 77% |
| 15 | Me-Si(Me)-O benzo, n-Bu | cyclohexylidene-Li | 4-iodoanisole | PdCl$_2$ (3 mol %) dpca (4 mol %) CuI (10 mol %) | cyclohexylidene(4-methoxyphenyl)methane | 67% |
| 16 | Me-Si(Me)-O benzo, n-Bu | TBSO-CH=CH-Li | 4-iodoanisole | PdCl$_2$ (3 mol %) dpca (4 mol %) CuI (10 mol %) | TBSO-CH=CH-(4-methoxyphenyl) | 81% |
| 17 | Me-Si(Me)-O benzo, Ph | TBSO-CH=CH-Li | Ph(CH$_2$)$_2$CH=CHI | PdCl$_2$ (3 mol %) dpca (4 mol %) CuI (10 mol %) | Ph(CH$_2$)$_2$CH=CH-CH=CH-OTBS | 96% |
| 18 | Me-Si(Me)-O benzo, n-Bu | TBSO-CH=CH-Li | Ph(CH$_2$)$_2$CH=CHI | PdCl$_2$ (3 mol %) dpca (4 mol %) CuI (10 mol %) | Ph(CH$_2$)$_2$CH=CH-CH=CH-OH | 72% |
| 19 | Me-Si(Me)-O benzo, n-Bu | TBSO-CH=CH-Li | 3,4-DMBO-CH$_2$-CH(Me)-CH=CH-I | PdCl$_2$ (3 mol %) dpca (4 mol %) CuI (10 mol %) | OTBS-CH=CH-CH=CH-CH(Me)-CH$_2$-ODMB | 78% |
| 20 | Me-Si(Me)-O benzo, n-Bu | PhLi | F$_2$CHO-C(=CH$_2$)-C(Br)=CH$_2$ | PdCl$_2$ (3 mol %) dpca (4 mol %) CuI (10 mol %) | | — |

-continued

Scheme 6

| Entry | Siloxane | Nu—Li | E—X | Catalyst System | Product | Isolated Yield |
|---|---|---|---|---|---|---|
| 21 | Me,Me-Si-O, n-Bu (benzosiloxole) | PhLi | MeO, OMe, Br, vinyl diene | PdCl$_2$ (3 mol %) dpca (4 mol %) CuI (10 mol %) | | — |
| 22 | Me,Me-Si-O, Ph (benzosiloxole) | TBSO-CH=CH-Li | 4-iodoanisole (I-C$_6$H$_4$-OMe) | PdCl$_2$ (3 mol %) dpca (4 mol %) CuI (10 mol %) | TBSO-CH=CH-C$_6$H$_4$-OMe | 93% |
| 23 | Me,Me-Si-O, Ph (benzosiloxole) | TBSO-CH=CH-Li | Ph-CH$_2$CH$_2$-CH=CH-I | PdCl$_2$ (3 mol %) dpca (4 mol %) CuI (10 mol %) | Ph-(CH=CH)$_2$-CH$_2$CH$_2$-OTBS | 96% |
| 24 | i-Pr,i-Pr-Si-O, Bu (benzosiloxole) | Pent-CH=CH-Li | 4-iodoanisole | PdCl$_2$ (3 mol %) dpca (4 mol %) CuI (10 mol %) | C$_5$H$_{11}$-CH=CH-C$_6$H$_4$-OMe | 84% |
| 25 | i-Pr,i-Pr-Si-O, Bu (benzosiloxole) | TBSO-CH=CH-Li | 4-iodoanisole | PdCl$_2$ (3 mol %) dpca (4 mol %) CuI (10 mol %) | HO-CH$_2$-CH=CH-C$_6$H$_4$-OMe | 80% |
| 26 | i-Pr,i-Pr-Si-O, Bu (benzosiloxole) | TBSO-CH=CH-Li | Ph-CH$_2$CH$_2$-CH=CH-I | PdCl$_2$ (3 mol %) dpca (4 mol %) CuI (10 mol %) | Ph-(CH=CH)$_2$-CH$_2$CH$_2$-OTBS | 81% |
| 27 | i-Pr,i-Pr-Si-O, Bu (benzosiloxole) | TBSO-CH=CH-Li | 5-iodo-2-morpholinopyridine | PdCl$_2$ (3 mol %) dpca (4 mol %) CuI (10 mol %) | OTBS-CH=CH-(5-pyridyl-2-morpholino) | 74% |

-continued

Scheme 6

| Entry | Siloxane | Nu—Li | E—X | Catalyst System | Product | Isolated Yield |
|---|---|---|---|---|---|---|
| 28 | i-Pr, i-Pr Si-O, Bu (benzosiloxole) | PhLi | 5-iodo-2-morpholinopyridine | PdCl$_2$ (3 mol %) dpca (4 mol %) CuI (10 mol %) | 5-phenyl-2-morpholinopyridine | 84% |
| 29 | i-Pr, i-Pr Si-O, Ph (benzosiloxole) | Pent-CH=CH-Li | 4-iodoanisole | PdCl$_2$ (3 mol %) dpca (4 mol %) CuI (10 mol %) | C$_5$H$_{11}$-CH=CH-C$_6$H$_4$-OMe | 96% |
| 30 | i-Pr, i-Pr Si-O, Ph (benzosiloxole) | TBSO-CH=CH-Li | 4-iodoanisole | PdCl$_2$ (3 mol %) dpca (4 mol %) CuI (10 mol %) | HO-CH=CH-C$_6$H$_4$-OMe | 83% |
| 31 | i-Pr, i-Pr Si-O, Ph (benzosiloxole) | TBSO-CH=CH-Li | Ph-CH$_2$CH$_2$-CH=CH-I | PdCl$_2$ (3 mol %) dpca (4 mol %) CuI (10 mol %) | Ph-CH$_2$CH$_2$-CH=CH-CH=CH-OH | 87% |
| 32 | i-Pr, i-Pr Si-O, Ph (benzosiloxole) | TBSO-CH=CH-Li | 5-iodo-2-morpholinopyridine | PdCl$_2$ (3 mol %) dpca (4 mol %) CuI (10 mol %) | OTBS-CH=CH-(5-pyridyl)-2-morpholine | 80% |
| 33 | i-Pr, i-Pr Si-O, Ph (benzosiloxole) | PhLi | 5-iodo-2-morpholinopyridine | PdCl$_2$ (3 mol %) dpca (4 mol %) CuI (10 mol %) | 5-phenyl-2-morpholinopyridine | 69% |
| 34 | i-Pr, i-Pr Si-O, Ph (benzosiloxole) | PhLi | 4-iodobenzonitrile | PdCl$_2$ (3 mol %) dpca (4 mol %) CuI (10 mol %) | 4-phenylbenzonitrile | 79% |

-continued

| | | | | | | |
|---|---|---|---|---|---|---|
| | | | Scheme 6 | | | |

| Entry | Siloxane | Nu—Li | E—X | Catalyst System | Product | Isolated Yield |
|---|---|---|---|---|---|---|
| 35 | i-Pr/i-Pr siloxane with CF$_3$, CF$_3$ | PhLi | 4-chloro-fluorobenzene | Pd(OAc)$_2$ (10 mol %) XPhos (20 mol %) | 4-fluorobiphenyl | 96% |
| 36 | i-Pr/i-Pr siloxane with CF$_3$, CF$_3$ | PhLi | 4-chloroanisole | Pd(OAc)$_2$ (10 mol %) XPhos (20 mol %) | 4-methoxybiphenyl | 96% |
| 37 | i-Pr/i-Pr siloxane with CF$_3$, CF$_3$ | PhLi | methyl 4-chlorobenzoate | Pd(OAc)$_2$ (10 mol %) XPhos (20 mol %) | methyl biphenyl-4-carboxylate | 81% |
| 38 | i-Pr/i-Pr siloxane with CF$_3$, CF$_3$ | PhLi | 4-chlorobenzonitrile | Pd(OAc)$_2$ (10 mol %) XPhos (20 mol %) | 4-cyanobiphenyl | 73% |
| 39 | i-Pr/i-Pr siloxane with CF$_3$, CF$_3$ | PhLi | 2-chlorobenzoxazole | Pd(OAc)$_2$ (10 mol %) XPhos (20 mol %) | 2-phenylbenzoxazole | 68% |
| 40 | i-Pr/i-Pr siloxane with CF$_3$, CF$_3$ | PhLi | 4-chloroquinoline | Pd(OAc)$_2$ (10 mol %) XPhos (20 mol %) | 4-phenylquinoline | 63% |
| 41 | i-Pr/i-Pr siloxane with CF$_3$, CF$_3$ | PhLi | 4-chloro-3-fluorobenzonitrile | Pd(OAc)$_2$ (10 mol %) XPhos (20 mol %) | 3-fluoro-4-phenylbenzonitrile | 70% |

Scheme 6 -continued

| Entry | Siloxane | Nu—Li | E—X | Catalyst System | Product | Isolated Yield |
|---|---|---|---|---|---|---|
| 42 | i-Pr, i-Pr Si-O, CF₃, CF₃ (benzosiloxole) | PhLi | 4-Br-2-F-1-Cl-benzene | Pd(OAc)₂ (10 mol %) XPhos (20 mol %) | 2-fluoro-4-chlorobiphenyl | 69% |
| 43 | i-Pr, i-Pr Si-O, CF₃, CF₃ | PhLi | 2-chloropyridine | Pd(OAc)₂ (10 mol %) XPhos (20 mol %) | 2-phenylpyridine | 83% |
| 44 | i-Pr, i-Pr Si-O, CF₃, CF₃ | PhLi | 3-chloropyridine | Pd(OAc)₂ (10 mol %) XPhos (20 mol %) | 3-phenylpyridine | 89% |
| 45 | i-Pr, i-Pr Si-O, CF₃, CF₃ | PhLi | 4-chloropyridine | Pd(OAc)₂ (10 mol %) XPhos (20 mol %) | 4-phenylpyridine | 85% 92% |
| 46 | i-Pr, i-Pr Si-O, CF₃, CF₃ | PhLi | 4′-iodoacetophenone | PdCl₂ (5 mol %) dpca (7 mol %) | 4-acetylbiphenyl | 90% |
| 47 | i-Pr, i-Pr Si-O, CF₃, CF₃ | PhLi | methyl 4-iodobenzoate | PdCl₂ (5 mol %) dpca (7 mol %) | methyl biphenyl-4-carboxylate | — |
| 48 | Et, Et Si-O, Bu | PhLi | 4-chloroanisole | Pd(OAc)₂ (10 mol %) XPhos (20 mol %) | 4-methoxybiphenyl | 69% |

As can be seen in Scheme 7, the synthetic utility of the cross-coupling method may be expanded to include the use of sp3-hybridized organolithium species and alkyl halides. By employing Pd- or Ni-catalysis, it may be possible access sp2-sp3 coupled products. Additionally, sp3-sp3 cross-couplings involving secondary alkyl halides may also be possible. It is preferred, in some examples, that iso-propyl group or groups are present on the silicon in order to avoid competitive transfer of primary alkyl groups from the activated silicon species (e.g., methyl).

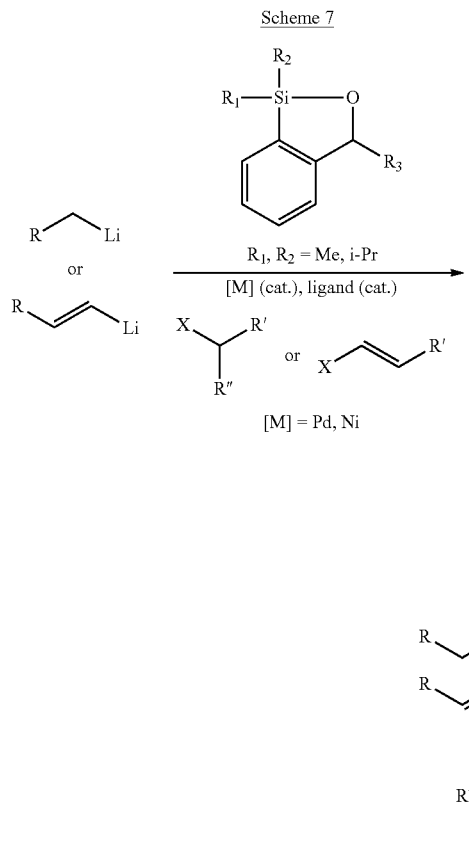

Scheme 7

Additional examples of cross-coupling reactions performed using siloxanes of the invention are set forth in Scheme 8. It is noteworthy that, once the desired cross-coupling reaction has been completed, the siloxanes of the disclosure can be recovered from the reaction mixtures. This is in contrast to previously-described cross-coupling reactions wherein the transfer agent cannot be recovered from the reaction mixture. Recovery of at least 95%, by weight of the starting weight of the siloxane, can be achieved. For example, between about 50% to at least 95%, preferably about 60%, 65%, 70%, 75%, 80%, 85%, 90%, or about 95%, of the siloxane can be recovered from the reaction mixtures.

Scheme 8

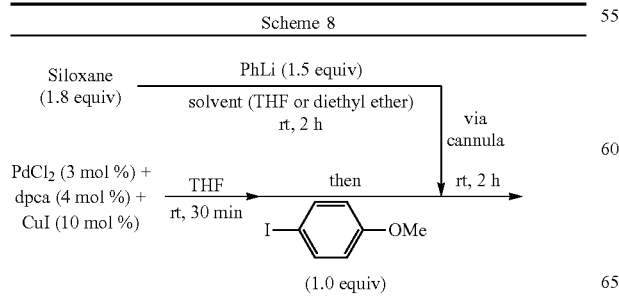

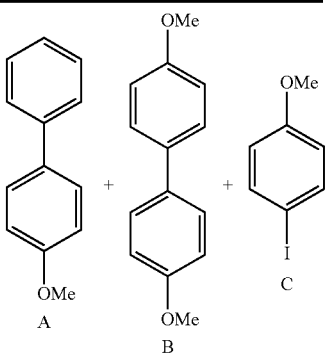

| Entry | Siloxane | $^1$H NMR Ratio$^b$ A:B:C | Siloxane Recovery (%) | Yield (A) (%)$^d$ |
|---|---|---|---|---|
| 1 | (1) | >20:--:-- | e | 96 |
| 2 | (1a) | >20:--:-- | e | 92 |
| 3 | (1e) | 13:1.0:-- | e | 63$^1$ |
| 4 | (1f) | 1.7:1.2:1.0 | e | f |
| 5 | (2c) | 2.0:1.0:-- | 92$^c$ | 42 |

| | | | | |
|---|---|---|---|---|
| 6 | 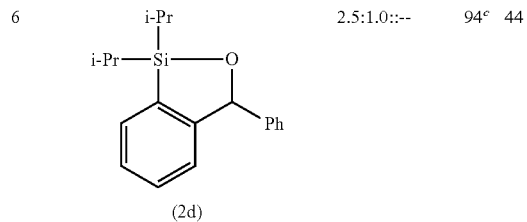 (2d) | 2.5:1.0::-- | 94[e] | 44 |
| 7 | 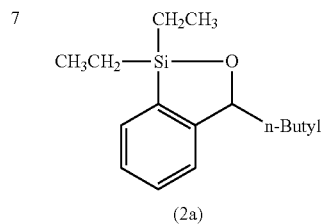 (2a) | >20:--:-- | 81[e] | 96 |
| 8 | 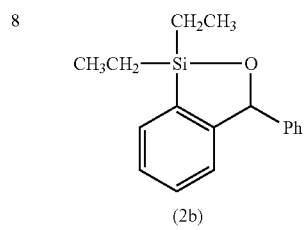 (2b) | >20:--:-- | 85[e] | 98 |
| 9 | 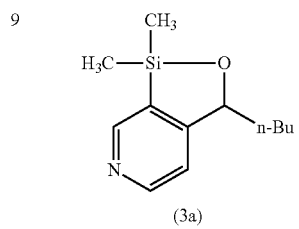 (3a) | >20:--:-- | e | 98 |
| 10 | 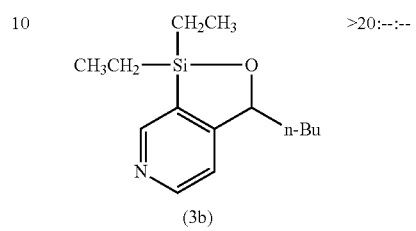 (3b) | >20:--:-- | e | 98 |
| 11 | 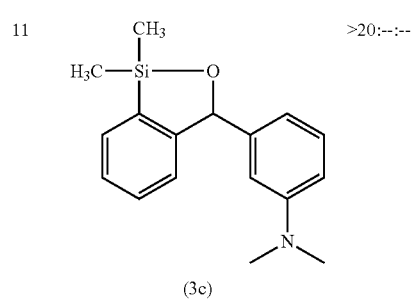 (3c) | >20:--:-- | 67[x] | 92 |
| 12 | 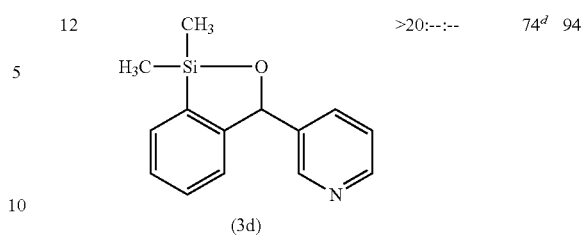 (3d) | >20:--:-- | 74[d] | 94 |
| 13 | 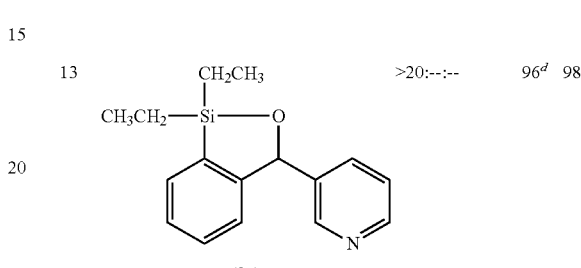 (3e) | >20:--:-- | 96[d] | 98 |
| 14 | 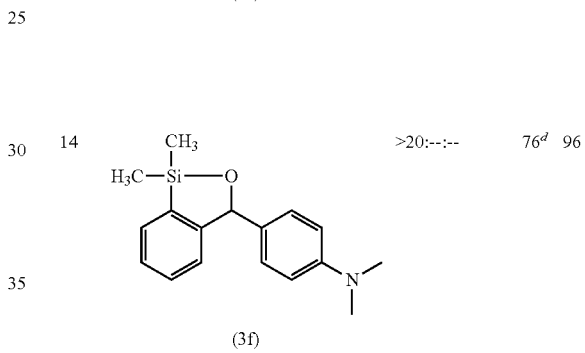 (3f) | >20:--:-- | 76[d] | 96 |
| 15 | 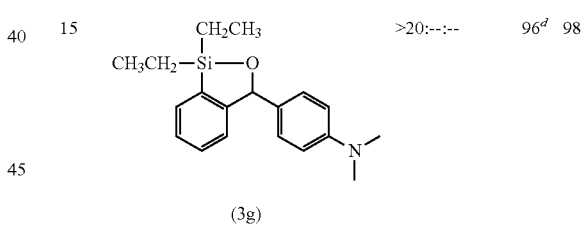 (3g) | >20:--:-- | 96[d] | 98 |

[a]All reactions were performed on 0.45 mmol scale with 4-iodoanisole as the limiting reagent.
[b]Requires heating to 50° C. to participate in the cross-coupling reaction.
[c]Determined by $^1$H NMR analysis of the crude reaction mixture.
[d]Recovered via column chromatography.
[e]Siloxanes were not recovered
[f]Compounds A, B, and C co-eluted Methods of the invention can also be accomplished without copper in the catalyst system. In such embodiments, the catalyst system comprises a palladium-based catalysts, for example, PdCl$_2$ or Pd(OAc)$_2$. These embodiments can also employ the use of a phosphate ligand, for example, XPhos, SPhos, DavePhos, and Johnphos, to form a palladium complex catalyst system. Examples of such methods are set forth in Schemes 9A and 9B. See also, Scheme 6. It is noteworthy that in such embodiments, the siloxane reagent can be recovered.

Scheme 9A
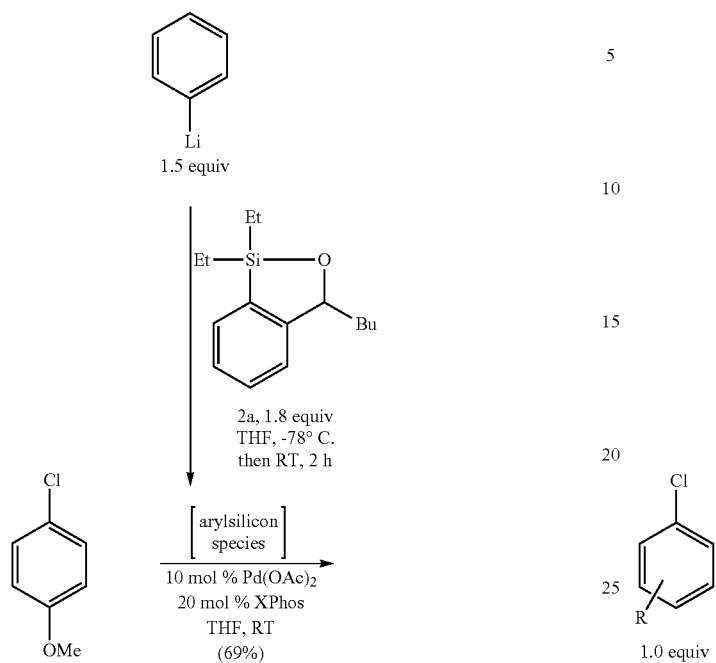
4-methoxy-biphenyl
(75:25)
Scheme 9B
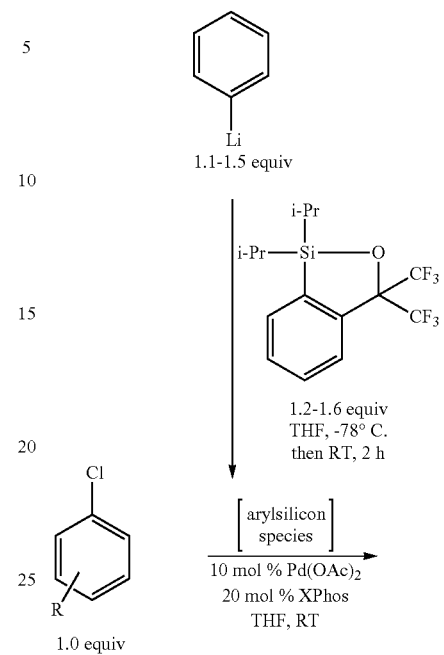
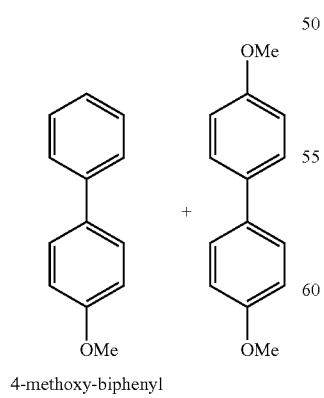
R = one or more halogen, alkoxy, —COOalkyl, —CN, —COalkyl Scheme 9C

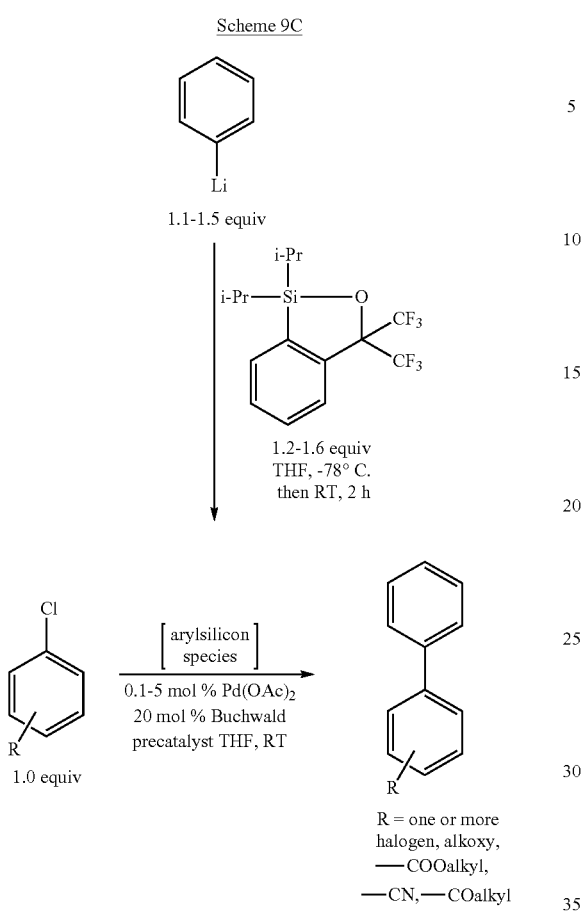

Polymeric siloxane compounds are also within the scope of the invention. As can be seen in Scheme 10 (wherein n is about 150 to about 300, preferably about 200 or 250), the siloxane motif may be incorporated into a polymer via ring-opening metathesis polymerization (ROMP). For example, according to Scheme 10, treatment of commercially available 5-norbornene-2-carboxaldehyde (a mixture of endo- and exo-isomers) with phenylmagnesium bromide generated the benzylic alcohol. Subsequent ortho-lithiation with n-BuLi, followed by trapping with $Me_2SiHCl$ and treatment with $H_2O$ provided a mixture of benzyl alcohol and siloxane (observed by $^1$H-NMR), which was treated with catalytic KOtBu to furnish complete conversion to the desired siloxane monomer. This sequence can be performed on multigram-scale. ROMP (ring opening metathesis polymerization) of this monomer was then achieved smoothly with the first generation Grubbs catalyst.

Scheme 10

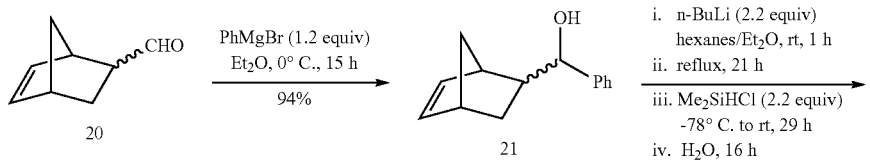

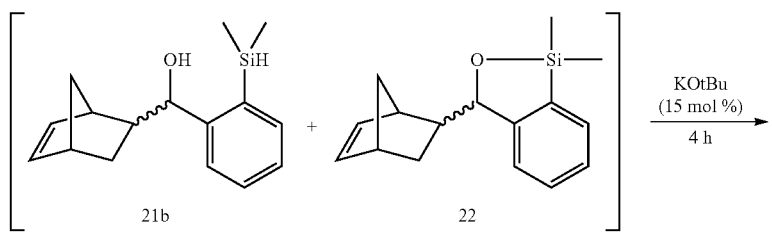

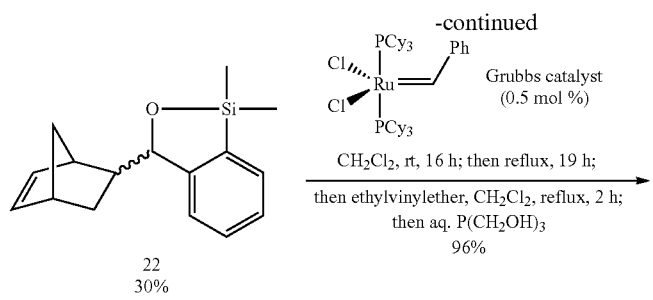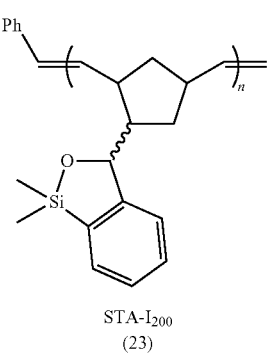

The polymer can be obtained in near quantitative yield without using cross-linking units or co-polymerization agents. As such, the loading of the polymer with siloxane units should be nearly identical to the molarity of the monomer, e.g., 3.9 mmol/g for the example set forth in Scheme 9, with each polymer chain having a relative length of 200-mers. The number of repeating siloxane units on each polymer chain can be adjusted by changing the amount of Grubbs catalyst used during the polymerization process.

These polymers of the invention are generally soluble in common organic solvents such as those used in the cross-coupling reaction.

The silicon transfer reagent may also be incorporated into a solid support, for example a resin, using "click chemistry," which is understood by those in the art to include, for example, the reaction of an alkyne and an azide to produce a 1,2,3-triazole. See Scheme 11. In preferred embodiments of the invention, the reaction is between an alkyne-capped resin, such as those known in the art, and an azido-siloxane, which can be prepared according to known methods. (Scheme 11). In these embodiments, the compounds of formula I can be tethered to a resin via a triazoyl linker. These embodiments of the inventions may facilitate removed of the transfer reagent from the reaction mixture by mechanical means such as filtration. Additionally, the transfer agent may be regenerated and reused.

-continued

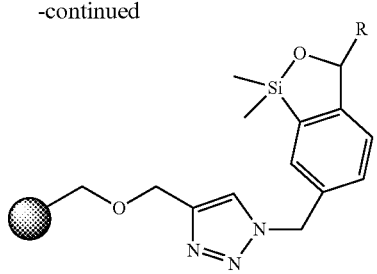

To further exemplify the invention, STA-I$_{200}$, one embodiment of the invention, was used to mediate the cross-coupling of phenyl lithium and 1-iodoanisole. See Scheme 12.

Scheme 12

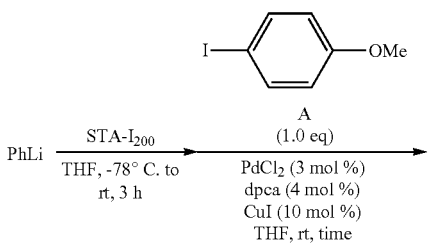

| Entry | Equiv. PhLi | Equiv STA-I$_{200}$ | Conc. STA-I$_{200}$ | Time | $^1$H-NMR Results[b] (B:A:C) |
|---|---|---|---|---|---|
| 1 | 1.5 | 2.0 | 15 mg/mL | 25 h | 57:40:3 |
| 2[d] | 2.5 | 3.0 | 15 mg/mL | 15 h | 90:5:5 |
| 3[e] | 2.5 | 3.0 | 10 mg/mL | 2 h | 100:nd:<1 |
| 4 | 1.5 | 3.0 | 10 mg/mL | 15 h | 84:11:5 |

Scheme 11

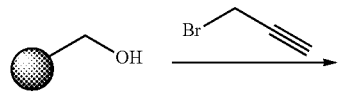

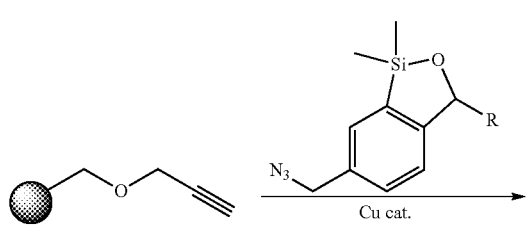

| 5 | 2.0 | 3.0 | 10 mg/mL | 2 h | 72:18:<1 |
| 6 | 2.0 | 2.5 | 10 mg/mL | 2 h | 88:9:3 |
| 7[f] | 2.5 | — | — | 2 h | 14:77:9[g] |

[a]All reactions were performed on 0.3 mmol scale in THF with 4-iodoanisole as the limiting reagent.
[b]Determined by ¹H-NMR analysis of crude mixture of reaction products following aqueous workup, extraction with Et₂O and removal of recovered polymer via precipitation in acetonitrile.
[c]Part of recovered polymer remained insoluble in THF.
[d]Small amount of recovered polymer remained insoluble in THF; 82% isolated yield of B.
[e]Polymer was recovered quantitatively and re-useable; 98% isolated yield of B.
[f]No siloxane polymer was used in the reaction; a solution of PhLi in THF was used as a substitute.
[g]Mixture of other products was also observed.

nd = not detected.

The polymeric siloxanes of the invention have utility in, for example, the cross-coupling between ary organolithiums and aryl or alkenyl iodides. Examples of such cross-coupling reactions are set forth in Scheme 13.

Scheme 13

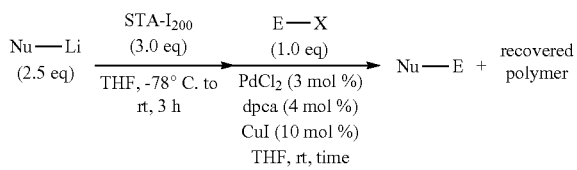

| Entry | Nu—Li | E—X | Time | Product (Nu—E) | Yield |
|---|---|---|---|---|---|
| 1 | PhLi | I—C₆H₄—OMe | 2 h | Ph—C₆H₄—OMe | 98% |
| 2 | PhLi | I—C₆H₄—CN | 2 h | Ph—C₆H₄—CN | 91% |
| 3 | PhLi | I-pyridyl-morpholine | 2 h | Ph-pyridyl-morpholine | 93% |
| 4 | PhLi | Br—C₆H₄—OMe | 24 h | Ph—C₆H₄—OMe | 7% |
| 5 | PhLi | Br—C₆H₄—CN | 12 h | Ph—C₆H₄—CN | 89% |
| 6 | MeO—C₆H₄—Li | I—CH=CH—CH₂CH₂—Ph | 2 h | MeO—C₆H₄—CH=CH—CH₂CH₂—Ph | 98% |
| 7 | C₅H₁₁—CH=CH—Li | I—C₆H₄—OMe | 2 h | C₅H₁₁—CH=CH—C₆H₄—OMe | 71% |
| 8 | Ph—CH₂CH₂—CH=CH—Li | I—C₆H₄—CN | 17 h | Ph—CH₂CH₂—CH=CH—C₆H₄—CN | 70% |
| 9 | TBSO—CH=CH—Li | I—CH=CH—CH₂CH₂—Ph | 15 h | HO—CH=CH—CH=CH—CH₂CH₂—Ph | 72% |

Polymeric siloxanes of the invention are also recyclable and retain activity through multiple cross-coupling reaction cycles, using the same nucleophile for each transformation. See, e.g., Scheme 14.

Scheme 14

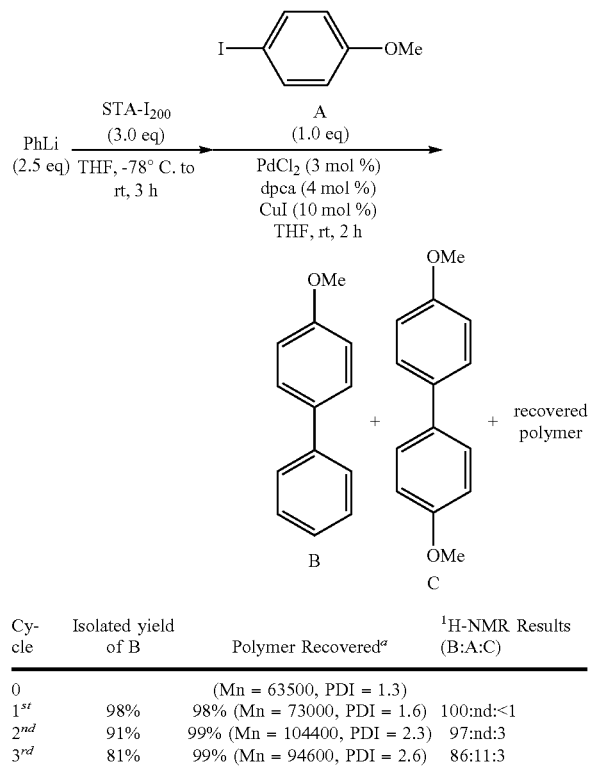

| Cycle | Isolated yield of B | Polymer Recovered[a] | $^1$H-NMR Results (B:A:C) |
|---|---|---|---|
| 0 | | (Mn = 63500, PDI = 1.3) | |
| $1^{st}$ | 98% | 98% (Mn = 73000, PDI = 1.6) | 100:nd:<1 |
| $2^{nd}$ | 91% | 99% (Mn = 104400, PDI = 2.3) | 97:nd:3 |
| $3^{rd}$ | 81% | 99% (Mn = 94600, PDI = 2.6) | 86:11:3 |

[a]Poly(methyl methacrylate) standards were used to determine Mn and PDI values.
Mn = number average molecule weight.
PDI = polydispersity index.

Polymeric siloxanes of the invention can also transfer different nucleophiles in repeated cycles. See, e.g., Scheme 15.

Scheme 15

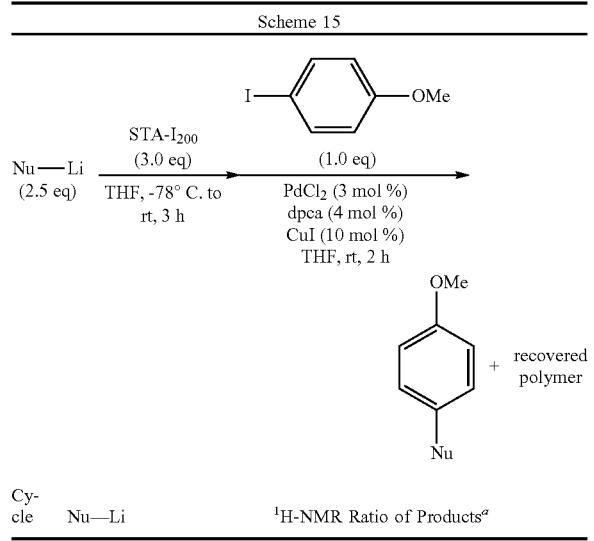

| Cycle | Nu—Li | $^1$H-NMR Ratio of Products[a] |
|---|---|---|

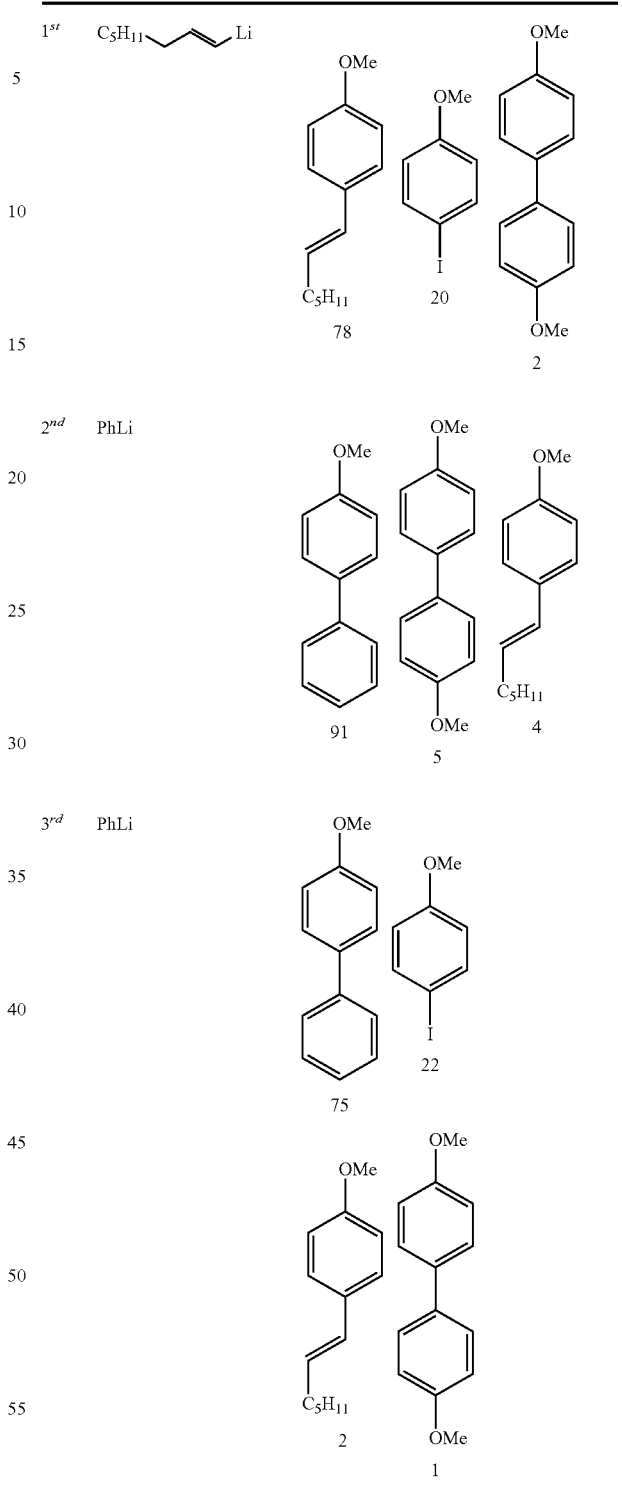

[a]Determined by $^1$H-NMR analysis of crude mixture of reaction products following aqueous workup, extraction with Et$_2$O and removal of recovered polymer via precipitation in acetonitrile.

Also within the scope of the invention are methods of forming carbon-nitrogen bonds using the siloxanes of the invention. Examples of such methods are set forth in Scheme 16.

Scheme 16

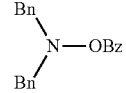

| Entry | R—Li | (R')₂N—OBz | Yield | Recovered siloxane |
|---|---|---|---|---|
| 1 | PhLi | Bn₂N—OBz | 98% | — |
| 2 | PhLi | Et₂N—OBz | 91% | 85% |
| 3 | PhLi | piperidine-N—OBz | 93% | 87% |
| 4 | PhLi | morpholine-N—OBz | 65% (using 10% CuI) | 75% |
| 5 | PhLi | morpholine-N—OBz | 83% (using 20% CuI) | 86% |
| 6 | 4-MeO-C₆H₄-Li | Bn₂N—OBz | 73% | 80% |
| 7 | 4-F-C₆H₄-Li | Bn₂N—OBz | 40% | — |

Additional examples of cross-coupling reactions performed using siloxanes of the invention are set forth in Schemes 17-19:

Scheme 17

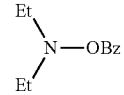

G2 = R¹ = Cl, R² = H
G3 = R¹ = OMs, R² = H
G4 = R¹ = OMs, R² = Me

L1 (XPhos)
L2 (RuPhos)
L3 (dpca)

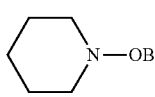

| entry | 1 (equiv) | PhLi (equiv) | [Pd] ligand | ¹H NMR results (6a:5:8)ᵃ | yield 6a (%)ᵇ | recovery 1 (%)ᶜ |
|---|---|---|---|---|---|---|
| 1ᵈ | 1.6 | 1.5 | PdCl2, CuI dpca | 0:100:0 | — | 85 |
| 2 | 1.6 | 1.5 | Pd2(dba)3 5 mol % L2 10 mol % | 66.5:33.5:0 | — | 84 |
| 3 | 1.6 | 1.5 | Pd2(dba)3 5 mol % L1 10 mol % | 80.4:19.6:0 | — | 85 |

-continued

| 4 | 1.6 | 1.5 | Pd(OAc)2 5 mol % L1 10 mol % | 86.5:13.5:0 | — | 86 |
| 5 | 1.4 | 1.3 | Pd(OAc)2 10 mol % L1 20 mol % | 100:0:0 | 95 | 88 |
| 6[e] | 1.2 | 1.1 | G2 5 mol % L1 | 6.2:93.8:0 | — | 85 |
| 7[e] | 1.2 | 1.1 | G3 5 mol % L1 | 43.5:56.5:0 | — | 86 |

-continued

| 8[e] | 1.4 | 1.3 | G4 3 mol % L1 | 100:0:0 | 98 | 84 |
| 9[e,f] | 1.2 | 1.1 | G4 0.5 mol % L1 | 100:0:0 | 96 | 87 |
| 10 | — | 1.1 | G4 5 mol % L1 | 28.4:58.1:13.5 | — | — |
| 11 | 1.4 | 1.3 | — | 0:100:0 | — | — |

[a] 1H NMR analysis of the crude reaction mixture.
[b] Isolated yields.
[c] Recovered via flash chromatography.
[d] PdCl2 5 mol %, CuI 10 mol %, and dpca 6 mol %.
[e] 1:1 ratio of pre-catalyst to XPhos utilized.
[f] Reaction performed at 60° C.

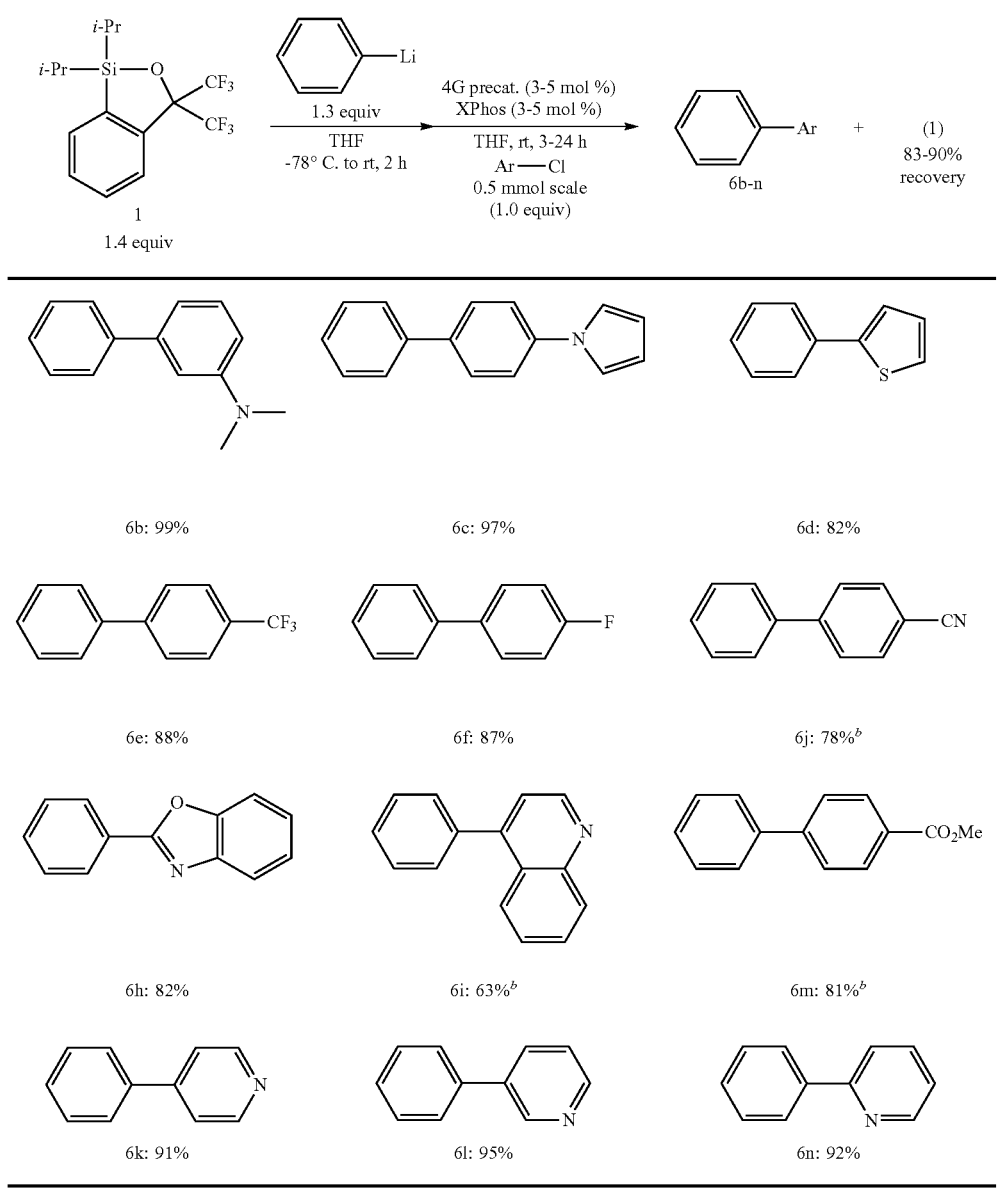

Scheme 18

6b: 99%
6c: 97%
6d: 82%
6e: 88%
6f: 87%
6j: 78%[b]
6h: 82%
6i: 63%[b]
6m: 81%[b]
6k: 91%
6l: 95%
6n: 92%

[a] Isolated yields.
[b] Pd(OAc)2 10 mol %, XPhos 20 mol %.

Scheme 19

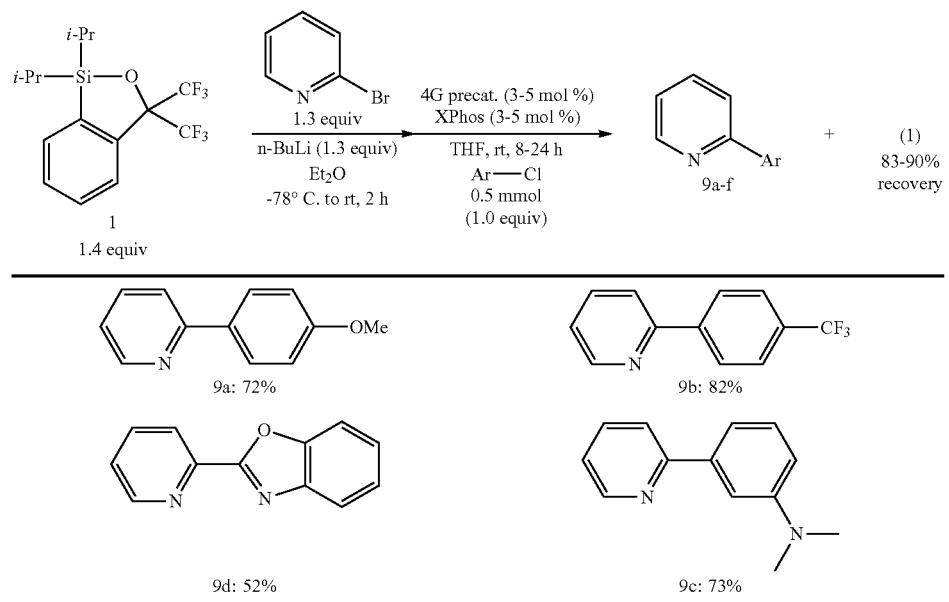

The following examples are only illustrative and are not meant to limit the invention. Those skilled in the art will be able to practice the full breadth of the invention in view of the following examples, this specification, and the knowledge of the art.

EXAMPLES

General.

All moisture-sensitive reactions were performed using syringe-septum cap techniques under an inert atmosphere of $N_2$. All glassware was flame dried or dried in an oven (140° C.) for at least 4 h prior to use. Reactions were magnetically stirred unless otherwise stated. Tetrahydrofuran (THF), dichloromethane ($CH_2Cl_2$) and diethyl ether ($Et_2O$) were dried by passage through alumina in a Pure Solve™ PS-400 solvent purification system. Unless otherwise stated, solvents and reagents were used as received. Analytical thin layer chromatography was performed on pre-coated silica gel 60 F-254 plates (particle size 40-55 micron, 230-400 mesh) and visualized by a uv lamp or by staining with PMA (2 g phosphomolybdic acid dissolved in 20 mL absolute ethanol), $KMnO_4$ (1.5 g of $KMnO_4$, 10 g of $K_2CO_3$ and 2.5 mL of 5% aq. NaOH in 150 mL $H_2O$), or CAM (4.8 g of $(NH_4)_6Mo_7O_{24} \cdot 4H_2O$ and 0.2 g of $Ce(SO_4)_2$ in 100 mL of a 3.5 N $H_2SO_4$ solution) stain. Column chromatography was performed using silica gel (Silacycle Silaflash® P60, 40-63 micron particle size, 230-300 mesh) and compressed air pressure with commercial grade solvents. Yields refer to chromatographically and spectroscopically pure compounds, unless otherwise stated. NMR spectra were recorded at 500 MHz/125 MHz ($^1$H NMR/$^{13}$C NMR) on a Bruker Avance III 500 MHz spectrometer at 300 K. Chemical shifts are reported in parts per million with the residual solvent peak as an internal standard. $^1$H NMR spectra are tabulated as follows: chemical shift, multiplicity (s=singlet, d=doublet, t=triplet, q=quartet, qn=quintet, dd=doublet of doublets, ddd=doublet of doublet of doublets, dddd=doublet of doublet of doublet of doublets, dt=doublet of triplets, m=multiplet, b=broad), coupling constant and integration. $^{13}$C NMR spectra are tabulated by observed peak. Melting points were determined using a Thomas-Hoover capillary melting point apparatus and are uncorrected. Infrared spectra were measured on a Jasco FT/IR 480 plus spectrometer. High-resolution mass spectra (HRMS) were obtained at the University of Pennsylvania on a Waters GCT Premier spectrometer. Single crystal X-ray structures were determined at the University of Pennsylvania. X-ray intensity data were collected on a Rigaku Mercury CCD or Bruker APEXII CCD area detector employing graphite-monochromated Mo-Ka radiation (1=0.71073 Å) at a temperature of 143(1) K.

Example 1. Preparation of Water-Washed Silica Gel for Column Chromatography (where Specified)

Silica gel was suspended in $H_2O$ and the slurry mixture was then packed into a prepared column. The obtained $H_2O$-washed silica gel packed column was then rinsed with 2 column volumes of acetone, 1 column volume of EtOAc and 2 column volumes of hexanes, successively. The obtained column was then ready for use.

Example 2. Preparation of 3-butyl-1,1-dimethyl-1, 3-dihydro-benzo[c][1,2]oxasilole

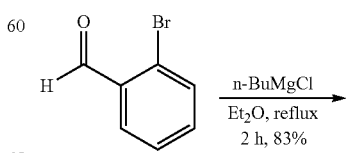

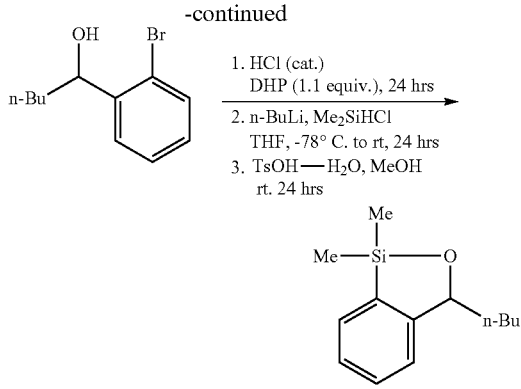

Synthesis of 1-(2-bromophenyl)pentan-1-ol

Following the procedure described by Wagner (P. J. Wagner and E. J. Siebert, J. Am. Chem. Soc, 1981, 103, 7329), n-BuMgCl (2.0 M in Et$_2$O, 14.3 mL, 38.1 mmol) was added slowly to a vigorously stirred solution of 2-bromobenzaldehyde (6.4 g, 34.6 mmol) in Et$_2$O (50 mL) at rt. The resulting suspension was heated to reflux for 2 h and cooled to rt. The reaction mixture was quenched, using extreme caution, by slow addition of aqueous 1 N HCl solution. The organic layer was collected and the aqueous layer was extracted using Et$_2$O (2×60 mL). The combined organic layers were washed with brine, dried over MgSO$_4$ and concentrated in vacuo. The crude product was purified by flash chromatography on silica gel (1:10, EtOAc/Hexane) to afford the desired alcohol (6.9 g, 83%) as light yellow oil: $^1$H NMR (500 MHz, CDCl$_3$) δ 7.55 (dd, J=7.5, 1.0 Hz, 1H), 7.52 (dd, J=8.0, 1.0 Hz, 1H), 7.34 (td, J=7.5, 1.0 Hz, 1H), 7.12 (td, J=8.0, 1.5 Hz, 1H), 5.07 (dd, J=8.0, 4.5 Hz, 1H), 2.08 (OH, 1H), 1.80 (m, 1H), 1.69 (m, 1H), 1.51 (m, 1H), 1.38 (m, 3H), 0.94 (t, J=7.5 Hz, 3H); $^{13}$C NMR (125 MHz, CDCl$_3$) δ 144.1, 132.8, 128.9, 127.5, 122.2, 73.1, 37.6, 28.2, 22.7, 14.2.

Following Hiyama's procedure (Y. Nakao, H. Imanaka, A. K. Sahoo, A. Yada, T. Hiyama, J. Am. Chem. Soc. 2005, 127, 6952), the alcohol (6.9 g, 28.5 mmol) obtained above was dissolved in 3,4-dihydro-2H-pyran (3.0 g, 31.4 mmol) at rt. A drop of concentrated HCl (37.5%, about 10 μL) was added and the resulting mixture was stirred for 24 h at rt. The reaction mixture was diluted with diethyl ether (20 mL) and quenched by addition of aqueous NaHCO$_3$ (10 mL). The organic layer was collected and the aqueous layer was extracted using Et$_2$O (2×20 mL). The combined organic layers were washed with brine, dried over MgSO$_4$ and concentrated in vacuo. The crude product was purified by short flash chromatography on silica gel (1:10, EtOAc/Hexane) to afford a colorless oil (7.9 g, 24.2 mmol, 85%), which was dissolved in dry THF (60 mL) and cooled to −78° C. n-Butyllithium (2.0 M in hexane, 13.3 mL, 26.6 mmol) was added dropwise and the resulting solution was allowed to warm to −30° C. over 1 hr and stirred for an additional 30 min at −30° C. The solution was then cooled to −78° C. and chlorodimethylsilane (Me$_2$SiHCl, 4.6 g, 48.4 mmol) was added dropwise over 10 minutes. The resulting reaction mixture was allowed to warm to rt and was stirred overnight. The reaction mixture was quenched by addition of saturated aqueous NaHCO$_3$ (30 mL) and extracted with Et$_2$O (3×50 mL). The combined organic layers were washed with brine, dried with MgSO$_4$ and concentrated in vacuo. The crude product was purified by short flash chromatography on silica gel (1:10, EtOAc/Hexane) to afford the desired silylated product (6.22 g, 20.3 mmol, 84%) as a colorless oil. The silylated product was then dissolved in MeOH (40 mL) and p-TsOH.H$_2$O (0.08 g, 0.4 mmol) was added. The resulting solution was stirred for 24 hrs at rt and concentrated in vacuo. Distillation of the crude product under vacuum afforded 1-oxa-2-silacyclopentane (±)-2 (3.89 g, 17.7 mmol, 87%) as a colorless oil: IR (neat, cm$^{-1}$) 3059, 2958, 2927, 2858, 1594, 1443, 1250, 1080, 919, 865, 830, 789, 744; $^1$H NMR (500 MHz, CDCl$_3$) δ 7.56 (d, J=7.0 Hz, 1H), 7.41 (td, J=7.5, 1.0 Hz, 1H), 7.29 (t, J=7.0 Hz, 1H), 7.22 (d, J=7.5 Hz, 1H), 5.26 (dd, J=7.5, 3.5 Hz, 1H), 1.93 (m, 1H), 1.62 (m, 1H), 1.50-1.20 (m, 4H), 0.90 (t, J=7.5 Hz, 3H), 0.41 (s, 3H), 0.38 (s, 3H); $^{13}$C NMR (125 MHz, CDCl$_3$) δ 153.5, 135.8, 131.0, 129.7, 127.0, 122.4, 81.9, 38.9, 27.5, 23.0. 14.2, 1.5, 0.8; HRMS (ES$^+$) m/z (M+H)$^+$: Calcd for C$_{13}$H$_{21}$OSi: 221.1362, found: 221.1367.

Example 3. Preparation of Silicon-Based Cross Coupling Agents

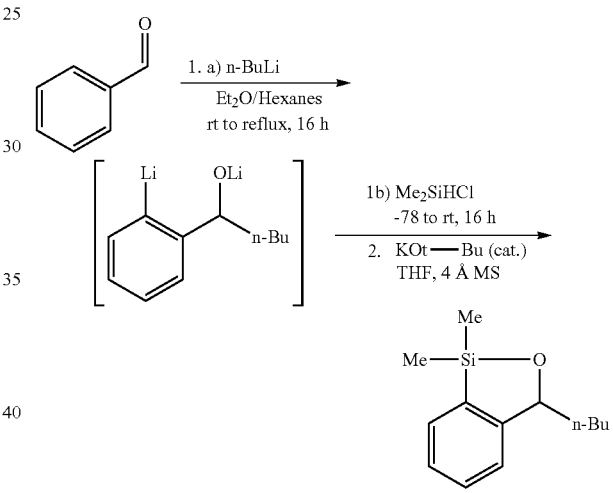

To a solution of benzaldehyde (5.1 mL, 50 mmol) in a mixture of hexanes (250 mL) and Et$_2$O (200 mL) under an atmosphere of N$_2$ at room temperature was added a solution of n-butyllithium in hexanes (110 mmol) dropwise, maintaining the reaction mixture at room temperature using a water bath. The resulting solution was heated to reflux for 16 h, and the brown mixture was cooled to room temperature, then to −78° C. using an acetone/CO$_2$(s) bath. To this solution was added R$_1$(R$_2$)SiHCl (110 mmol), and the resulting pale yellow slurry was allowed to warm to room temperature and stirred for 16 h. The reaction mixture was diluted with 0.5 M aq. KHCO$_3$ (100 mL) and extracted with Et$_2$O (3×50 mL). The combined organic layers were washed with brine, dried (MgSO$_4$), filtered and concentrated under reduced pressure to afford an oil.

The crude oil was taken up in THF (500 mL) in a 2 L flask, and 4 Å molecular sieves were added. To the stirred mixture was added KOt-Bu (280 mg, 2.5 mmol), and vigorous gas evolution resulted. Once gas production had ceased, the turbid mixture was diluted with H$_2$O (100 mL), and the aqueous phase was extracted with Et$_2$O (3×50 mL). The organic extracts were dried (MgSO$_4$), filtered and concentrated. The resulting yellow oil was purified by chromatography on SiO$_2$ (100% Hex then 5% Et$_2$O/Hex). In some cases, the title compound was purified a second time by bulb-to-bulb distillation under vacuum to remove co-eluting impurities.

Example 4. 3-Butyl-1,1-dimethyl-1,3-dihydrobenzo[c][1,2]oxasilole (1)

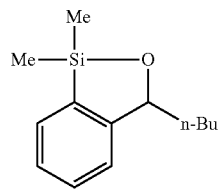

To a cooled solution of benzaldehyde (21.0 g, 198 mmol, 1.00 equiv) in hexanes (733 mL, pre-dried over MgSO$_4$) and Et$_2$O (587 mL) at 0° C. was added n-BuLi (224 mL, 1.94 M in hexanes, 435 mmol, 2.20 equiv) dropwise. The reaction mixture was allowed to warm to room temperature and was stirred for 30 minutes. The flask was then fitted with a reflux condenser and the reaction mixture was heated to reflux (75° C.) for 16 h. A dark solution resulted and the reaction mixture was allowed to cool to room temperature. The reflux condenser was removed and the reaction mixture was cooled to −78° C. and Me$_2$SiHCl (48.4 mL, 435 mmol, 2.20 equiv) was then added dropwise. The reaction mixture was allowed to slowly warm to room temperature and stirred for 8 h. The resulting pale yellow slurry was then quenched with H$_2$O (300 mL) and the aqueous phase extracted with Et$_2$O (3×100 mL). The combined organic layers were washed with brine, dried (MgSO$_4$), filtered and concentrated under reduced pressure.

The resulting crude orange oil was taken up in THF (200 mL) at room temperature and 4 Å molecular sieves (3.00 g) and KOt-Bu (1.10 g, 9.90 mmol, 0.05 equiv) were added as a single portion and vigorous evolution of H$_2$ was observed. The reaction mixture was allowed to stir at room temperature for 5 h, quenched with H$_2$O (50 mL) and the aqueous phase extracted with Et$_2$O (3×100 mL). The combined organic layers were washed with brine, dried (MgSO$_4$), filtered and concentrated under reduced pressure. Flash chromatography on water-washed silica (100% hexanes then 1% EtOAc in hexanes) followed by Kugelrohr distillation (85-95° C., 0.05 mmHg) provided 1 (22.7 g, 103 mmol, 52% yield) as a colorless oil. Analytical data matches that which has been previously reported:[7] R$_f$ 0.35 (1% EtOAc in hexanes); $^1$H NMR (500 MHz, CDCl$_3$) δ 7.56 (d, J=7.0 Hz, 1H), 7.41 (td, J=7.5, 1.0 Hz, 1H), 7.29 (t, J=7.0 Hz, 1H), 7.22 (d, =7.5 Hz, 1H), 5.26 (dd, =7.5, 3.5 Hz, 1H), 1.93 (m, 1H), 1.62 (m, 1H), 1.50-1.20 (m, 4H), 0.90 (t, J=7.5 Hz, 3H), 0.41 (s, 3H), 0.38 (s, 3H); $^{13}$C NMR (125 MHz, CDCl$_3$) δ 153.5, 135.8, 131.0, 129.7, 127.0, 122.4, 81.9, 38.9, 27.5, 23.0. 14.2, 1.5, 0.8; IR (neat) 3059 (s), 2958 (m), 2927 (m), 2858 (m), 1594 (s), 1443 (s), 1250 (s), 1080 (s), 919 (m), 865 (s), 830 (s), 789 (s), 744 (s) cm$^{−1}$; HRMS (ES+) m/z calcd for C$_{13}$H$_{21}$OSi [M+H]$^+$ 221.1362, found 221.1367.

Example 5. 1,1-Dimethyl-3-phenyl-1,3-dihydrobenzo[c][1,2]oxasilole (1a)

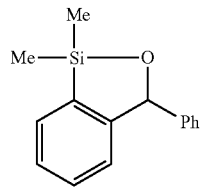

1,1-Dimethyl-3-phenyl-1,3-dihydrobenzo[c][1,2]oxasilole (1a)

Phenylmagnesium bromide (10.4 mL, 3.00 M in Et$_2$O, 31.3 mmol, 1.20 equiv) was added dropwise to a vigorously stirred solution of 2-bromobenzaldehyde (4.82 g, 26.1 mmol, 1.00 equiv) in Et$_2$O (75 mL) at 0° C. The reaction mixture was stirred at room temperature for 12 h, quenched with sat. aq. NH$_4$Cl (25 mL) and the aqueous phase extracted with Et$_2$O (2×25 mL). The combined organic layers were washed with brine, dried (MgSO$_4$), and concentrated under reduced pressure. Flash chromatography on silica (1% Et$_2$O in hexanes then 10% Et$_2$O in hexanes) provided the desired (2-bromophenyl)(phenyl)methanol (S1) (6.44 g, 24.5 mmol, 94% yield) as a white solid. Analytical data matches that which has been previously reported:[8] R$_f$ 0.3 (10% EtOAc in hexanes); $^1$H NMR (500 MHz, CDCl$_3$) δ 7.61-7.52 (m, 2H), 7.41 (d, J=6.9 Hz, 2H), 7.37-7.31 (m, 3H), 7.28 (t, J=7.1 Hz, 1H), 7.15 (dt, J=1.6, 7.6 Hz, 1H), 6.21 (d, J=3.8 Hz, 1H), 2.34 (d, J=4.0 Hz, 1H); $^{13}$C NMR (125 MHz, CDCl$_3$) δ 142.6, 142.3, 133.0, 129.3 128.6, 127.9, 127.8, 127.2, 126.7, 122.9, 74.9.

The resulting (2-bromophenyl)(phenyl)methanol (51) (4.29 g, 16.3 mmol, 1.00 equiv) was dissolved in THF (50 mL) and n-BuLi (14.7 mL, 2.45 M in hexanes, 35.9 mmol, 2.20 equiv) was added dropwise at −78° C. The reaction mixture was stirred for 1 h, followed by the addition of Me$_2$SiHCl (3.90 mL, 35.9 mmol, 2.20 equiv) at −78° C. The resulting reaction mixture was allowed to warm to room temperature and stirred for 12 h. The reaction mixture was quenched by addition of t-BuOH (20 mL) and stirred for 5 h, followed by the addition of H$_2$O (20 ml) and stirred for another 2 h. The aqueous phase was then extracted with Et$_2$O (2×25 mL) and the combined organic layers were washed with brine, dried (MgSO$_4$), and concentrated under reduced pressure. Flash chromatography on water-washed silica gel (100% hexanes then 1% Et$_2$O/Hexanes) provided the desired siloxane 1a (1.82 g, 26.8 mmol, 46% yield) as a white crystalline solid: m.p. 45.5-46.5° C.; R$_f$ 0.3 (5% Et$_2$O in hexanes); $^1$H NMR (500 MHz, CDCl$_3$) δ 7.63-7.59 (m, 1H), 7.36-7.26 (m, 7H), 7.05-7.01 (m, 1H), 6.17 (s, 1H), 0.53 (s, 3H), 0.45 (s, 3H); $^{13}$C NMR (125 MHz, CDCl$_3$) δ 152.6, 143.9, 135.3, 130.8, 129.9, 128.7, 127.9, 127.3, 127.3, 123.9, 84.2, 1.4, 0.7; IR (CH$_2$Cl$_2$) 3057 (m), 2964 (m), 2874 (m), 1447 (m), 1265 (s), 1181 (m), 1136 (m), 1042 (s), 1016 (s), 862 (s), 822 (s), 793 (s), 740 (s), 702 (s), 656 (m) cm$^{−1}$; HRMS (CI$^+$) m/z calculated for C$_{15}$H$_{17}$SiO [M+H]$^+$ 241.1049, found 241.1034.

Example 6. 3-Isopropyl-1,1-dimethyl-1,3-dihydrobenzo[c][1,2]oxasilole (1b)

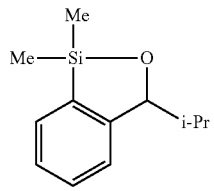 [SMILES: CC(C)C1O[Si](C)(C)c2ccccc21]

Phenylmagnesium bromide (11.7 mL, 3.00 M in Et$_2$O, 35.1 mmol, 1.20 equiv) was added dropwise to a vigorously stirred solution of isobutyraldehyde (2.11 g, 29.3 mmol, 1.00 equiv) in Et$_2$O (50 mL) at 0° C. The reaction mixture was warmed to room temperature and stirred for 12 h, then quenched with sat. aq. NH$_4$Cl (25 mL). The aqueous phase was extracted with Et$_2$O (2×25 mL) and the combined organic layers were washed with brine, dried (MgSO$_4$) and concentrated under reduced pressure. Flash chromatography on silica, (10% Et$_2$O in hexanes) provided the desired 2-methyl-1-phenylpropan-1-ol (S2) (4.09 g, 27.2 mmol, 93% yield) as a colorless oil. Analytical data matches that which has been previously reported:[9] R$_f$ 0.15 (10% Et$_2$O in hexanes); $^1$H NMR (500 MHz, CDCl$_3$) δ 7.36-7.26 (m, 5H), 4.37 (dd, J=3.3, 6.8 Hz, 1H), 2.02-1.91 (m, 1H), 1.82 (d, J=3.4 Hz, 1H), 1.01 (d, J=6.7 Hz, 3H), 0.81 (d, J=6.7 Hz, 3H); $^{13}$C NMR (125 MHz, CDCl$_3$) δ 143.8, 128.3, 127.6, 126.7, 80.2, 35.4, 19.2, 18.4.

The resulting 2-methyl-1-phenylpropan-1-ol (S2) (2.76 g, 18.4 mmol, 1.00 equiv) was dissolved in hexanes (125 mL, pre-dried over MgSO$_4$) and Et$_2$O (100 ml) at 0° C. and n-BuLi (22.9 ml, 1.77 M in hexanes, 40.5 mmol, 2.20 equiv) was added dropwise. The reaction mixture was allowed to warm to room temperature and was stirred for 30 minutes. The flask was then fitted with a reflux condenser and the system was heated to reflux (75° C.) for 16 h. A dark solution resulted and the reaction mixture was allowed to cool to room temperature. The reflux condenser was removed and the reaction mixture was cooled to −78° C. Me$_2$SiHCl (4.40 ml, 40.5 mmol, 2.20 equiv) was added dropwise. The reaction mixture was allowed to slowly warm to room temperature and stirred for 12 h. The slurry was quenched by addition of t-BuOH (20 mL) and stirred for 5 h, followed by the addition of H$_2$O (20 ml) and stirred for another 2 h. The aqueous phase was extracted with Et$_2$O (2×25 mL) and the combined organic layers were washed with brine, dried (MgSO$_4$), filtered and concentrated under reduced pressure. Flash chromatography on water-washed silica gel (100% hexanes then 1% Et$_2$O/Hexanes) followed by Kugelrohr distillation (75-80° C., 0.025 mmHg) provided 1b (1.48 g, 7.17 mmol, 39% yield) as a colorless oil: R$_f$ 0.5 (5% Et$_2$O in hexanes); $^1$H NMR (500 MHz, CDCl$_3$) δ 7.54 (d, J=7.1 Hz, 1H), 7.39 (dt, J=1.0, 7.5 Hz, 1H), 7.29 (t, J=7.2 Hz, 1H), 7.20 (d, J=7.7 Hz, 1H), 5.17 (d, J=2.2 Hz, 1H), 2.12 (dspt, J=2.5, 6.8 Hz, 1H), 1.17 (d, J=6.9 Hz, 3H), 0.60 (d, J=6.7 Hz, 3H), 0.41 (s, 3H), 0.36 (s, 3H); $^{13}$C NMR (125 MHz, CDCl$_3$) δ 152.5, 136.4, 130.8, 129.7, 127.0, 122.4, 86.5, 34.6, 20.4, 15.0, 1.0, 0.8; IR (neat) 3060 (m), 2963 (s), 2873 (m), 1594 (m), 1469 (m), 1442 (m), 1383 (m), 1365 (m), 1251 (s), 1198 (m), 1137 (m), 1120 (m), 1102 (s), 1067 (s), 1014 (s), 953 (s), 874 (s), 830 (s), 788 (s), 744 (m), 704 (m), 651 (m) cm$^{-1}$; HRMS (CI$^+$) m/z calculated for C$_{11}$H$_{15}$SiO [M-Me]$^+$ 191.0892, found 191.0893.

Example 7. 3-(sec-Butyl)-1,1-dimethyl-1,3-dihydrobenzo[c][1,2]oxasilole (1c)

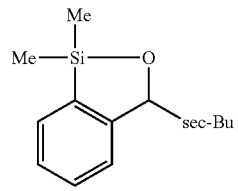

To a cooled solution of benzaldehyde (3.25 g, 30.6 mmol, 1.00 equiv) in hexanes (125 ml, pre-dried over MgSO$_4$) and Et$_2$O (100 mL) at 0° C. was added sec-BuLi (26.2 mL, 1.4 M in cyclohexane, 36.7 mmol, 1.20 equiv) dropwise. The reaction mixture was allowed to warm to room temperature and was stirred for 5 h, at which time n-BuLi (20.7 mL, 1.77 M in hexanes, 36.7 mmol, 1.20 equiv) was added dropwise. The flask was then fitted with a reflux condenser and the system was heated to reflux (75° C.) for 16 h. A dark solution resulted and the reaction mixture was allowed to cool to room temperature. The reflux condenser was removed and the reaction mixture was cooled to −78° C. and Me$_2$SiHCl (7.97 ml, 67.3 mmol, 2.20 equiv) was added dropwise. The reaction mixture was allowed to slowly warm to room temperature and stirred for 12 h. The slurry was quenched by addition of t-BuOH (20 mL) and stirred for 5 h, followed by the addition of H$_2$O (20 ml) and stirred for another 2 h. The aqueous phase was extracted with Et$_2$O (2×25 mL) and the combined organic layers were washed with brine, dried (MgSO$_4$), filtered and concentrated under reduced pressure. Flash chromatography on water-washed silica gel (100% hexanes then 1% Et$_2$O/Hexanes) followed by Kugelrohr distillation (140-160° C., 0.01 mmHg) provided 1c, isolated as a 5:3 ratio of diastereomers by $^1$H NMR spectroscopy (2.02 g, 9.17 mmol, 30% yield) as a colorless oil: R$_f$ 0.55 (5% Et$_2$O in hexanes); Major diastereoisomer: $^1$H NMR (500 MHz, CDCl$_3$) δ 7.54 (d, J=7.1 Hz, 1H), 7.39 (t, J=7.5 Hz, 1H), 7.29 (t, J=7.1 Hz, 1H), 7.21 (d, J=7.7 Hz, 1H), 5.20 (d, J=2.2 Hz, 1H), 1.88-1.79 (m, 1H), 1.13 (d, J=6.9 Hz, 3H), 1.08-1.01 (m, 2H), 0.79 (t, J=7.4 Hz, 3H), 0.40 (s, 3H), 0.36 (s, 3H); $^{13}$C NMR (125 MHz, CDCl$_3$) δ 152.3, 136.6, 130.9, 129.6, 126.9, 122.4, 86.7, 41.8, 22.5, 16.9, 12.5, 1.0, 0.8. Minor diastereoisomer: $^1$H NMR (500 MHz, CDCl$_3$) δ 7.54 (d, J=7.1 Hz, 1H), 7.39 (t, J=7.5 Hz, 1H), 7.29 (t, J=7.1 Hz, 1H), 7.19 (d, J=7.7 Hz, 1H), 5.20 (d, J=1.2 Hz, 1H), 1.88-1.79 (m, 1H), 1.74-1.65 (m, 1H), 1.53-1.43 (m, 1H), 1.04 (t, J=7.7 Hz, 3H), 0.55 (d, J=6.7 Hz, 3H), 0.40 (s, 3H), 0.36 (s, 3H); $^{13}$C NMR (125 MHz, CDCl$_3$) δ 152.7, 136.4, 130.8, 129.7, 126.9, 122.2, 84.62, 41.5, 31.9, 27.5, 12.5, 1.0, 0.7; IR (neat) 3060 (m), 2962 (s), 2875 (s), 1594 (m), 1443 (s), 1375 (m), 1323 (m), 1250 (s), 1197 (m), 1137 (m), 1107 (s), 1068 (s), 1040 (s), 1014 (s), 960 (s), 875 (s), 826 (s), 789 (s), 746 (s), 705 (s), 653 (m) cm$^{-1}$; HRMS (CI$^+$) m/z calculated for C$_{13}$H$_{19}$SiO [M-H]$^+$ 221.1362, found 221.1368.

Example 8. 1,1,3-Trimethyl-1,3-dihydrobenzo[c][1,2]oxasilole (1d)

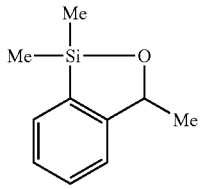

To a cooled solution of benzaldehyde (2.63 g, 24.8 mmol, 1.00 equiv) in hexanes (125 ml, pre-dried over $MgSO_4$) and $Et_2O$ (100 ml) at 0° C. was added MeLi (1.36 M in $Et_2O$, 29.7 mmol, 1.20 equiv) dropwise. The resulting solution was allowed to warm to room temperature and stirred for 5 h, at which time n-BuLi (12.1 mL, 2.45 M in hexanes, 29.7 mmol, 1.20 equiv) was added dropwise. The flask was then fitted with a reflux condenser and the system was heated to reflux (75° C.) for 16 h. A dark solution resulted and the reaction mixture was allowed to cool to room temperature. The reflux condenser was removed and the reaction mixture was cooled to −78° C. and $Me_2SiHCl$ (5.20 ml, 54.6 mmol, 2.20 equiv) was added dropwise. The reaction mixture was allowed to slowly warm to room temperature and stirred for 12 h. The reaction mixture was quenched by addition of t-BuOH (20 mL) and stirred for 5 h, followed by the addition of $H_2O$ (20 ml) and stirred for another 2 h. The aqueous phase was extracted with $Et_2O$ (2×25 mL) and the combined organic layers were washed with brine, dried ($MgSO_4$), filtered and concentrated under reduced pressure. Flash chromatography on water-washed silica gel (100% hexanes then 1% $Et_2O$/Hexanes) followed by Kugelrohr distillation (55° C., 0.01 mmHg) provided 1d (1.55 g, 8.69 mmol, 35% yield) as a colorless oil: $R_f$ 0.45 (5% $Et_2O$ in hexanes); $^1H$ NMR (500 MHz, $CDCl_3$) δ 7.56 (d, J=7.1 Hz, 1H), 7.40 (dt, J=0.8, 7.5 Hz, 1H), 7.30 (t, J=7.3 Hz, 1H), 7.22 (d, J=7.7 Hz, 1H), 5.34 (q, J=6.5 Hz, 1H), 1.51 (d, J=6.5 Hz, 3H), 0.41 (s, 3H), 0.37 (s, 3H); $^{13}C$ NMR (125 MHz, $CDCl_3$) δ 154.5, 135.2, 131.0, 129.8, 127.0, 122.3, 78.0, 25.4, 1.7, 0.6; IR (neat) 3060 (m), 2968 (s), 2924 (m), 2867 (m), 1595 (m), 1444 (s), 1368 (m), 1318 (s), 1251 (s), 1199 (m), 1137 (m), 1086 (s), 1028 (s), 929 (s), 855 (s), 828 (s), 793 (s), 759 (s), 742 (s), 696 (m), 653 (m) $cm^{-1}$; HRMS (CI$^+$) m/z calculated for $C_9H_{11}SiO$ [M−Me]$^+$ 163.0579, found 163.0578.

Example 9. 1,1,3,3-Tetramethyl-1,3-dihydrobenzo[c][1,2]oxasilole (1f):[1]

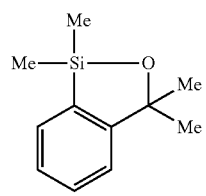

Following a previously reported procedure,[1] methyl 2-bromobenzoate (9.70 g, 45.0 mmol, 1.00 equiv) was dissolved in $Et_2O$ (100 ml) and cooled to 0° C. Methylmagnesium bromide (99 mL, 1.0 M in $Bu_2O$, 99.0 mmol, 2.20 equiv) was then added via cannula into the reaction mixture. The resulting solution was heated to reflux (40° C.) for 2 h then cooled to room temperature before being quenched with sat. aq. $NH_4Cl$ (75 mL). The aqueous phase extracted with $Et_2O$ (2×50 mL). The combined organic layers were washed with brine, dried ($MgSO_4$), filtered and concentrated under reduced pressure to afford 2-(2-bromophenyl)propan-2-ol (S3) (8.30 g, ca. 38.8 mmol, 1.00 equiv), which was used without further purification.

To the crude alcohol was added conc. HCl (3 drops) and 3,4-dihydro-2H-pyran (S3) (4.07 g, 48.5 mmol, 1.20 equiv) and stirred neat at room temperature for 24 h. The mixture was diluted with $Et_2O$ (50 mL), and washed with a sat. aq. $NaHCO_3$ (25 mL). The aqueous layer was extracted with $Et_2O$ (2×50 mL) and the combined organic layers were washed with brine, dried ($MgSO_4$), filtered and concentrated under reduced pressure to afford 2-((2-(2-bromophenyl)propan-2-yl)oxy)tetrahydro-2H-pyran (S4) (8.30 g, ca. 38.8 mmol, 1.00 equiv) which was used without further purification.

The crude THP-protected product (S4) was dissolved in THF (50 mL) and n-BuLi (23.3 mL, 2.00 Min hexanes, 46.6 mmol, 1.20 equiv) was added dropwise at −78° C. The reaction mixture was stirred for 1 h, followed by the addition of $Me_2SiHCl$ (6.30 mL, 58.2 mmol, 1.50 equiv) at −78° C. The resulting reaction mixture was allowed to warm to room temperature and stirred for 12 h. The reaction mixture was quenched by addition of $H_2O$ (50 ml). The aqueous phase was then extracted with $Et_2O$ (2×30 mL) and the combined organic layers were washed with brine, dried ($MgSO_4$), filtered and concentrated under reduced pressure to afford dimethyl(2-(2-((tetrahydro-2H-pyran-2-yl)oxy)propan-2-yl)phenyl)silane (S5) (8.30 g, ca. 38.8 mmol, 1.00 equiv) which was used without further purification.

To this crude material (S5) was added MeOH (50 mL) and p-toluenesulfonic acid monohydrate (370 mg, 1.94 mmol, 0.05 equiv), and the mixture was stirred at room temperature for 12 h before concentration under reduced pressure. The residue was diluted with $Et_2O$ (25 mL), and washed with a sat. aq. $NaHCO_3$ (25 mL). The aqueous layer was extracted with $Et_2O$ (2×25 mL), and the combined organic layers were washed with brine, dried ($MgSO_4$), filtered and concentrated under reduced pressure. Kugelrohr distillation (60° C., 0.01 mmHg) provided 1f (3.27 g, 17.0 mmol, 38% yield from methyl 2-bromobenzoate) as a colorless oil. Analytical data matches that which has been previously reported:[2] $R_f$ 0.3 (1% $Et_2O$ in hexanes); $^1H$ NMR (500 MHz, $CDCl_3$) δ 7.52 (dt, J=7.1, 0.9 Hz, 1H), 7.41 (td, J=7.5, 1.3 Hz, 1H), 7.30 (dt, J=7.2, 0.9 Hz, 1H), 7.22 (d, J=7.7 Hz, 1H), 1.55 (s, 6H), 0.39 (s, 6H); $^{13}C$ NMR (125 MHz, $CDCl_3$) δ 157.6, 134.4, 130.6, 129.7, 126.6, 122.1, 83.5, 32.1, 1.37.

Example 10. 3-Butyl-1,1-diisopropyl-1,3-dihydrobenzo[c][1,2]oxasilole (2c)

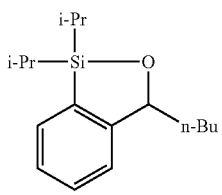

To a cooled solution of benzaldehyde (3.08 g, 29.0 mmol, 1.00 equiv) in hexanes (125 ml, pre-dried over MgSO$_4$) and Et$_2$O (100 ml) at 0° C. was added n-BuLi (27.8 mL, 2.3 M in hexanes, 63.9 mmol, 2.20 equiv) dropwise. The reaction mixture was allowed to warm to room temperature and was stirred for 30 minutes. The flask was then fitted with a reflux condenser and the system was heated to reflux (75° C.) for 16 h. A dark solution resulted and was allowed to cool to room temperature, the reflux condenser was removed and the reaction mixture was cooled to −78° C. and i-Pr$_2$SiHCl (10.9 ml, 63.8 mmol, 2.20 equiv) was added dropwise. The reaction mixture was allowed to slowly warm to room temperature and stirred for 12 h. The reaction mixture was quenched by addition of 3M HCl in MeOH (40 mL) at 0° C. and stirred for 12 h at room temperature. Water (100 mL) was added and stirred for another 2 h and the aqueous phase extracted with Et$_2$O (2×50 mL). The combined organic layers were washed with brine, dried (MgSO$_4$), filtered and concentrated under reduced pressure. Flash chromatography on silica (1% Et$_2$O/Hexanes) provided 2c (5.94 g, 21.5 mmol, 74% yield) as a colorless oil: R$_f$ 0.70 (5% Et$_2$O in hexanes); $^1$H NMR (500 MHz, CDCl$_3$) δ 7.53 (d, J=7.1 Hz, 1H), 7.38 (t, J=7.5 Hz, 1H), 7.27 (t, J=7.1 Hz, 1H), 7.20 (d, J=7.7 Hz, 1H), 5.18-5.14 (m, 1H), 1.94-1.86 (m, 1H), 1.60-1.48 (m, 3H), 1.45-1.30 (m, 2H), 1.25-1.16 (m, 2H), 1.06 (d, J=6.7 Hz, 3H), 1.05 (d, J=7.1 Hz, 3H), 1.00 (d, J=7.5 Hz, 3H), 0.93 (d, J=7.3 Hz, 3H), 0.92 (t, J=7.3 Hz, 3H); $^{13}$C NMR (125 MHz, CDCl$_3$) δ 154.7, 132.4, 132.2, 129.5, 126.7, 122.2, 82.3, 39.1, 28.1, 23.0, 17.6, 17.5, 17.2, 17.1, 14.2, 13.4, 12.9; IR (neat) 3059 (m), 3000 (m), 2941 (s), 2864 (s), 1595 (m), 1464 (s), 1443 (m), 1381 (m), 1261 (m), 1111 (m), 1080 (s), 1054 (m), 1012 (m), 988 (m), 973 (m), 917 (s), 880 (s), 846 (m), 831 (m), 816 (m), 749 (s), 716 (s), 668 (s), 648 (m), 612 (m) cm$^{-1}$; HRMS (CI$^+$) m/z calculated for C$_{14}$H$_{21}$SiO [M-C$_3$H$_7$]$^+$ 233.1726, found 233.1726.

Example 11. 1,1-Diisopropyl-3-phenyl-1,3-dihydrobenzo[c][1,2]oxasilole (2d)

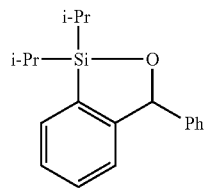 [SMILES: CC(C)[Si]1(C(C)C)OC(c2ccccc2)c2ccccc21]

To the previously prepared (2-bromophenyl)(phenyl)methanol (S1) (5.18 g, 19.7 mmol, 1.00 equiv) dissolved in THF (50 mL) was added n-BuLi (19.0 mL, 2.28 M in hexanes, 43.3 mmol 2.20 equiv) dropwise at −78° C. The reaction mixture was stirred for 1 h, followed by the addition of i-Pr$_2$SiHCl (7.39 mL, 43.3 mmol, 2.20 equiv) at −78° C. The resulting reaction mixture was allowed to warm to room temperature and stirred for 12 h. The slurry was quenched by addition of 3M HCl in MeOH (40 mL) at 0° C. and stirred for 4 h at room temperature. Water (100 mL) was added and stirred for another 2 h and the aqueous phase extracted with Et$_2$O (2×50 mL). The combined organic layers were washed with brine, dried (MgSO$_4$), filtered and concentrated under reduced pressure. Flash chromatography on silica (1% Et$_2$O/Hexanes) provided 2d (4.12 g, 13.9 mmol, 71% yield) as a colorless oil: R$_f$ 0.45 (5% Et$_2$O in hexanes); $^1$H NMR (500 MHz, CDCl$_3$) δ 7.63-7.59 (m, 1H), 7.37-7.27 (m, 7H), 6.99 (d, J=6.9 Hz, 1H), 6.12 (s, 1H), 1.39-1.24 (m, 2H), 1.16 (d, J=7.5 Hz, 3H), 1.13 (d, J=7.5 Hz, 3H), 1.06 (d, J=5.7 Hz, 3H), 1.04 (d, J=5.7 Hz, 3H); $^{13}$C NMR (125 MHz, CDCl$_3$) δ 153.4, 143.8, 132.7, 131.9, 129.8, 128.6, 128.0, 127.8, 127.0, 123.9, 84.6, 17.7, 17.2, 13.6, 13.3; IR (neat) 3061 (m), 3031 (m), 3000 (m), 2942 (s), 2891 (m), 2864 (s), 1592 (m), 1494 (m), 1463 (s), 1442 (s), 1383 (m), 1263 (m), 1182 (m), 1133 (m), 1077 (m), 1065 (s), 1038 (s), 1014 (s), 988 (s), 919 (m), 881 (m), 815 (s), 747 (s), 732 (s), 713 (s), 698 (s), 669 (s), 633 (m) cm$^{-1}$; HRMS (CI$^+$) m/z calculated for C$_{16}$H$_{17}$SiO [M-C$_3$H$_7$]$^+$ 253.1049, found 253.1056.

Example 12. Preparation of Et$_2$SiHCl from Commercially Available Et$_2$SiH$_2$:[4]

Anhydrous CuCl$_2$ (96.5 g, 714 mmol, 2.10 equiv) was dried under vacuum at 200° C. (utilizing a sand bath) in a 2000 mL two-necked round-bottomed flask (RBF) for 12 hours. Upon cooling to room temperature, CuI (3.24 g, 17.0 mmol, 0.05 equiv), Et$_2$O (680 mL~0.5 M) and Et$_2$SiH$_2$ (30.0 g, 340 mmol, 1.00 equiv) were successively added and the resulting slurry stirred at room temperature for 43 hours. After 8 hours, it was noted that the reaction went from brown to light grey in color with black precipitate forming. After 43 hours, the reaction mixture was filtered under N$_2$ atmosphere and the flask rinsed with Et$_2$O (2×50 mL). The Et$_2$O was distilled (35° C.) and the reaction mixture transferred to a 100 mL flame-dried RBF via syringe, carefully leaving behind any remaining Cu salts. Kugelrohr distillation (95-100° C.) of this crude reaction mixture under N$_2$ provided clean Et$_2$SiHCl (32.2 g, 263 mmol, 77% yield) whose analytical data matches that which has been previously reported.[4]

Example 13. 3-Butyl-1,1-diethyl-1,3-dihydrobenzo[c][1,2]oxasilole (2a)

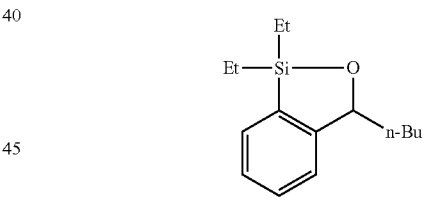

To a cooled solution of benzaldehyde (10.0 g, 94.2 mmol, 1.00 equiv) in hexanes (500 mL, pre-dried over MgSO$_4$) and Et$_2$O (400 mL) at 0° C. was added n-BuLi (86.4 mL, 2.40 M in hexanes, 2.20 equiv) dropwise. The reaction mixture was allowed to warm to room temperature and was stirred for 30 minutes. The flask was then fitted with a reflux condenser and the system was heated to reflux (75° C.) for 16 h. A dark solution resulted and the reaction mixture was allowed to cool to room temperature. The reflux condenser was removed and the reaction mixture was cooled to −78° C. and Et$_2$SiHCl (28.9 mL, 207 mmol, 2.20 equiv) was added dropwise. The reaction mixture was allowed to slowly warm to room temperature and stirred for 8 h. The resulting pale yellow slurry was then quenched with H$_2$O (300 mL) with vigorous evolution of H$_2$ gas observed. The reaction mixture was allowed to stir for 5 h and the aqueous layer extracted with Et$_2$O (3×100 mL). The combined organic layers were washed with brine, dried (MgSO$_4$), filtered and concentrated under reduced pressure. Flash chromatography on silica (100% hexanes to 1% EtOAc in hexanes) provided 2a (6.2 g, 25.0 mmol, 53% yield) as a colorless oil: $R_f$ 0.45 (1% EtOAc in hexanes); $^1$H NMR (500 MHz, CDCl$_3$) δ 7.54 (d, J=7.1 Hz, 1H), 7.39 (td, J=7.5, 1.0 Hz, 1H), 7.28 (t, J=7.2 Hz, 1H), 7.22 (d, J=7.5 Hz, 1H), 5.22 (dd, J=8.0, 3.3 Hz, 1H), 1.92 (m, 1H), 1.59 (m, 1H), 1.52-1.30 (m, 4H), 0.99 (t, J=7.7 Hz, 3H), 0.94-0.88 (m, 6H), 0.88-0.78 (m, 4H); $^{13}$C NMR (125 MHz, CDCl$_3$) δ 154.2, 133.7, 131.6, 129.6, 126.8, 122.3, 82.12, 39.1, 27.8, 22.9, 14.2, 7.38, 7.16, 6.88, 6.60; IR (neat) 3058 (m), 2956 (s), 2932 (m), 2874 (m), 1459 (s), 1080 (s), 1013 (m), 916 (s), 741 (s) cm$^{-1}$; HRMS (CI$^+$) m/z calculated for C$_{15}$H$_{24}$OSi [M]$^+$ 248.1596, found 248.1593.

Example 14. 1,1-Diethyl-3-phenyl-1,3-dihydrobenzo[c][1,2]oxasilole (2b)

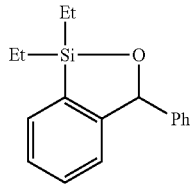 [SMILES: CC[Si]1(CC)OC(c2ccccc2)c2ccccc21]

To the previously prepared (2-bromophenyl)(phenyl)methanol (S1) (4.16 g, 15.8 mmol, 1.00 equiv) dissolved in THF (120 mL) was added n-BuLi (14.6 mL, 2.39 M in hexanes, 34.8 mmol, 2.20 equiv) dropwise at −78° C. The reaction mixture was stirred for 1 h, followed by the addition of Et$_2$SiHCl (4.84 mL, 34.8 mmol, 2.20 equiv) at −78° C. The resulting pale yellow slurry was then quenched with H$_2$O (300 mL) with vigorous evolution of H$_2$ gas observed. The reaction mixture was allowed to stir for 5 h and the aqueous phase was extracted with Et$_2$O (2×50 mL), the combined organic layers were washed with brine, dried (MgSO$_4$), filtered and concentrated under reduced pressure. Flash chromatography on silica (100% hexanes to 5% Et$_2$O in hexanes) provided 2b (1.74 g, 6.48 mmol, 41% yield) as a colorless oil: $R_f$ 0.45 (5% Et$_2$O in hexanes); $^1$H NMR (500 MHz, CDCl$_3$) δ 7.63-7.60 (m, 1H), 7.36-7.27 (m, 7H), 7.02 (d, J=7.1 Hz, 1H), 6.16 (s, 1H), 1.08 (t, J=7.9 Hz, 3H), 1.02-0.95 (m, 5H), 0.95-0.82 (m, 2H); $^{13}$C NMR (125 MHz, CDCl$_3$) δ 153.2, 143.9, 133.6, 131.4, 129.9, 128.6, 128.0, 127.5, 127.1, 123.9, 84.4, 7.4, 7.1, 7.0, 6.7; IR (neat) 3059 (m), 2999 (m), 2956 (s), 2878 (s), 1595 (m), 1486 (m), 1451 (s), 1412 (m), 1343 (w), 1265 (m), 1236 (m), 1182 (m), 1133 (m), 1012 (bs), 964 (m), 926 (m), 871 (m), 817 (s), 739 (bs), 661 (m), 629 (m) cm$^{-1}$; HRMS (CI$^+$) m/z calculated for C$_{17}$H$_{21}$SiO [M+H]$^+$ 269.1362, found 269.1366.

Example 15. 3-(1,1-Dimethyl-1,3-dihydrobenzo[c][1,2]oxasilol-3-yl)pyridine (3d)

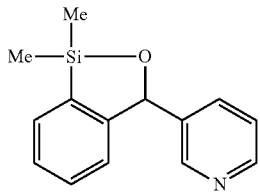 [SMILES: C[Si]1(C)OC(c2cccnc2)c2ccccc21]

To a cooled solution of Et$_2$O (420 mL) containing n-BuLi (48.7 mL, 2.00 M in hexanes, 1.30 equiv) at −78° C. was added 3-bromopyridine (20.0 g, 127 mmol, 1.20 equiv) dropwise. The resulting yellow slurry was allowed to stir at −78° C. for 30 min. 2-Bromobenzaldehyde (19.5 g, 106 mmol, 1.00 equiv) was added dropwise and the reaction mixture was allowed to stir for 5 h at −78° C. The reaction was then warmed to 0° C. and quenched with 3M aq. HCl (100 mL). The organic layer was washed with another portion of 3M aq. HCl (50 mL). The acidic aqueous layers were collected and neutralized to pH 8-9 with 1M aq. NaOH (350 mL), producing a white turbid mixture that was extracted with Et$_2$O (3×150 mL). The combined organic layers were dried (MgSO$_4$), filtered and concentrated under reduced pressure. Flash chromatography on silica (0.5% to 1% to 5% MeOH in CH$_2$Cl$_2$) provided (2-bromophenyl)(pyridin-3-yl)methanol (S6) (23.6 g, 89.4 mmol, 85% yield) as an off-white crystalline solid: Analytical data matches that which has been previously reported:[10] $R_f$ 0.35 (5% MeOH in CH$_2$Cl$_2$); $^1$H NMR (500 MHz, CDCl$_3$) δ 8.57 (d, J=1.8 Hz, 1H), 8.41 (dd, J=4.7, 1.1 Hz, 1H), 7.69 (td, J=7.6, 1.6 Hz, 1H), 7.62 (dd, J=7.8, 1.2 Hz, 1H), 7.53 (dd, J=7.9, 1.0 Hz, 1H), 7.36 (t, J=7.5 Hz, 1H), 7.23 (dd, J=7.8, 4.8 Hz, 1H), 7.16 (td, J=7.5, 1.5 Hz, 1H), 6.21 (s, 1H), 3.93 (s, 1H); $^{13}$C NMR (125 MHz, CDCl$_3$) δ 148.9, 148.7, 142.1, 138.2, 134.9, 133.1, 129.6, 128.5, 128.1, 123.6, 122.7, 72.7.

To a cooled solution of (2-bromophenyl)(pyridin-3-yl)methanol (S6) (7.00 g, 26.5 mmol, 1.00 equiv) in a mixture (1:1) of THF (100 mL) and Et$_2$O (100 mL) at −78° C. was added n-BuLi (29.2 mL, 2.00 M in hexanes, 2.20 equiv) dropwise. The resulting dark yellow slurry was allowed to stir at −78° C. for 30 min and Me$_2$SiHCl (6.50 mL, 58.3 mmol, 2.20 equiv) was added dropwise. The reaction mixture was allowed to slowly warm to room temperature and stirred for 12 h. The resulting orange slurry was then quenched with H$_2$O (100 mL) with vigorous evolution of H$_2$ gas observed. The reaction mixture was allowed to stir for 5 h and extracted with Et$_2$O (3×50 mL). The combined organic layers were collected and washed with 1M aq. HCl (3×50 mL). The acidic aqueous layers were collected and neutralized to pH 8-9 with 1M aq. NaOH (150 mL) producing a white turbid mixture that was extracted with Et$_2$O (3×100 mL). The combined organic layers were dried (MgSO$_4$), filtered and concentrated under reduced pressure. Flash chromatography on silica (0.5% to 1% to 5% MeOH in CH$_2$Cl$_2$) followed by Kugelrohr distillation (135-150° C., 0.01 mmHg) provided 3d (3.14 g, 13.0 mmol, 49% yield) as an off-white amorphous solid: $R_f$ 0.2 (5% MeOH in CH$_2$Cl$_2$); $^1$H NMR (500 MHz, CDCl$_3$) δ 8.61 (d, J=1.7 Hz, 1H), 8.53 (dd, J=4.7, 1.5 Hz, 1H), 7.63 (m, 1H), 7.53 (dt, J=7.8, 1.8 Hz, 1H), 7.33 (m, 2H), 7.25 (m, 1H), 7.00 (m, 1H), 6.20 (s, 1H), 0.53 (s, 3H), 0.46 (s, 3H); $^{13}$C NMR (125 MHz, CDCl$_3$) δ 151.4, 149.3, 148.8, 139.3, 135.2, 134.7, 131.0, 130.1, 127.6, 81.7, 1.23, 0.56; IR (neat) 3057 (m), 2959 (s), 1662 (m), 1579 (m), 1475 (s), 1427 (s), 1252 (s), 1181 (s), 1136 (s), 1051 (m), 860 (m), 822 (s), 791 (s), 750 (s), 713 (s) cm$^{-1}$; HRMS (ES$^+$) m/z calculated for C$_{14}$H$_{16}$NOSi [M+H]$^+$ 242.1001, found 242.0993.

Example 16. 3-(1,1-Diethyl-1,3-dihydrobenzo[c][1,2]oxasilol-3-yl)pyridine (3e)

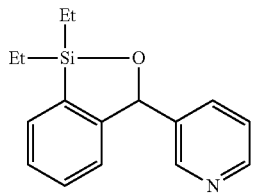 [SMILES: CC[Si]1(CC)OC(c2cccnc2)c2ccccc21]

To a cooled solution of (2-bromophenyl)(pyridin-3-yl)methanol (S6) (7.00 g, 26.5 mmol, 1.00 equiv) in a mixture (1:1) of dry THF (100 mL) and dry Et$_2$O (100 mL) at −78° C. was added n-BuLi (26.5 mL, 2.20 M in hexanes, 2.20 equiv) dropwise. The resulting dark yellow slurry was allowed to stir at −78° C. for 30 min and Et$_2$SiHCl (8.15 mL, 58.3 mmol, 2.20 equiv) was added dropwise. The reaction mixture was allowed to slowly warm to room temperature and stirred for 12 h. The resulting red-brown solution was then quenched with H$_2$O (100 mL) with vigorous evolution of H$_2$ gas observed. The reaction mixture was allowed to stir for 5 h and extracted with Et$_2$O (3×50 mL). The combined organic layers were collected and washed with 1M aq. HCl (3×50 mL). The acidic aqueous layers were collected and neutralized to pH 8-9 with 1M aq. NaOH (150 mL) producing a white turbid mixture that was extracted with Et$_2$O (3×100 mL). The combined organic layers were dried (MgSO$_4$), filtered and concentrated under reduced pressure. Flash chromatography on silica (0.5% to 1% to 3% MeOH in CH$_2$Cl$_2$) provided 3e (3.6 g, 13.4 mmol, 51% yield) as pale yellow oil: R$_f$ 0.45 (5% MeOH in CH$_2$Cl$_2$); $^1$H NMR (500 MHz, CDCl$_3$) δ 8.62 (d, J=1.0 Hz, 1H), 8.53 (dd, J=4.6, 1.2 Hz, 1H), 7.62 (m, 1H), 7.53 (dt, J=7.7, 1.6 Hz, 1H), 7.33 (m, 2H), 7.23 (m, 1H), 6.99 (d, J=6.6 Hz, 1H), 6.19 (s, 1H), 1.05 (m, 3H), 1.0-0.88 (m, 7H); $^{13}$C NMR (125 MHz, CDCl$_3$) δ 152.0, 149.4, 149.2, 139.3, 134.8, 133.6, 131.5, 130.1, 127.5, 123.7, 123.6, 81.9, 7.25, 7.00, 6.87, 6.51; IR (neat) 3057 (m), 2957 (m), 2876 (s), 2942 (s), 1580 (s), 1425 (m), 1235 (s), 1183 (s), 1134 (s), 1050 (m), 1017 (m), 817 (m), 744 (s) cm$^{-1}$; HRMS (ES$^+$) m/z calculated for C$_{16}$H$_{20}$NOSi [M+H]$^+$ 270.1314, found 270.1314.

Example 17. 1-(3-Bromopyridin-4-yl)pentan-1-ol (S7)

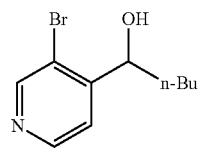

To a cooled THF solution (315 mL) of LDA, prepared from diisopopylamine (15.6 mL, 110 mmol, 1.10 equiv) and n-BuLi (42.4 mL, 2.50 M in hexanes, 106 mmol, 1.05 equiv), 3-bromopyridine (15.8 g, 100 mmol, 1.00 equiv) was added dropwise as a solution in THF (16.6 mL) at −78° C. The resulting solution temperature was further lowered to −100° C. and stirred for 10 min at this temperature before a THF solution (47.6 mL) of pentanal (21.4 mL, 200 mmol, 2.00 equiv) was added dropwise over 10 min. The reaction mixture was stirred at −100° C. for 1 h then warmed to −20° C. over 20 min before it was quenched with sat. aq. NH$_4$Cl (150 mL). The aqueous phase was extracted with EtOAc (3×75 mL). The combined organic layers were washed with brine, dried (MgSO$_4$) and concentrated under reduced pressure. Flash chromatography on silica (10% to 20% EtOAc in hexanes) provided 1-(3-bromopyridin-4-yl)pentan-1-ol (S7) (17.5 g, 71.7 mmol, 72% yield) as a yellow oil: R$_f$ 0.1 (30% EtOAc in hexanes); $^1$H NMR (500 MHz, CDCl$_3$) δ 8.56 (s, 1H), 8.43 (d, J=5.0 Hz, 1H), 7.50 (d, J=5.0 Hz, 1H), 4.98 (dd, J=8.0 Hz, 3.3 Hz, 1H), 3.03 (bs, 1H), 1.76 (m, 1H), 1.60 (m, 1H), 1.51-1.31 (m, 4H), 0.90 (t, J=7.2 Hz, 3H); $^{13}$C NMR (125 MHz, CDCl$_3$) δ 153.4, 151.6, 148.5, 122.3, 120.1, 72.0, 37.0, 27.9, 22.6, 14.1; IR (neat) 3272 (bs), 2956 (m), 2929 (m), 2859 (s), 1585 (m), 1463 (s), 1401 (m), 1082 (m), 1021 (s), 845 (s) cm$^{-1}$; HRMS (CI$^+$) m/z calculated for C$_{10}$H$_{15}$BrNO [M+H]$^+$ 244.0259, found 244.0259.

Example 18. 3-Butyl-1,1-dimethyl-1,3-dihydro-[1,2]oxasilolo[3,4-c]pyridine (3a)

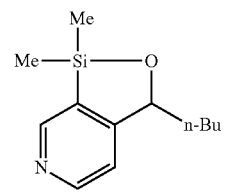

1-(3-bromopyridin-4-yl)pentan-1-ol (S7) (1.00 g, 4.10 mmol, 1.00 equiv) was dissolved in THF (27.4 mL) and n-BuLi (4.4 mL, 2.05 M in hexanes, 9.02 mmol, 2.20 equiv) was added dropwise at −78° C. The reaction mixture was stirred for 30 min, followed by the addition of Me$_2$SiHCl (0.98 mL, 9.02 mmol, 2.20 equiv) at −78° C. The resulting reaction mixture was allowed to warm to room temperature and was stirred for 12 h. The reaction mixture was then quenched with H$_2$O (20 mL) with evolution of H$_2$ gas observed. The reaction mixture was allowed to stir for 5 h and extracted with EtOAc (3×20 mL). The combined organic layers were collected and washed with 1M aq. HCl (3×40 mL). The acidic aqueous layers were collected and neutralized to pH 8-9 with 1M aq. NaOH (120 mL) producing a white turbid mixture that was extracted with Et$_2$O (3×75 mL). The combined organic layers were dried (MgSO$_4$), filtered and concentrated under reduced pressure. Flash chromatography on silica (50% EtOAc in hexanes) followed by Kugelrohr distillation (120° C., 0.01 mmHg) provided 3a (281 mg, 1.27 mmol, 31% yield) as an off-white amorphous solid: R$_f$ 0.3 (70% EtOAc in hexanes); $^1$H NMR (500 MHz, CDCl$_3$) δ 8.76 (bs, 1H), 8.56 (d, J=5.0 Hz, 1H), 7.13 (d, J=5.2 Hz, 1H), 5.20 (dd, J=7.5 Hz, J=3.5 Hz, 1H), 1.90 (m, 1H), 1.59 (m, 1H), 1.45-1.29 (m, 4H), 0.89 (t, J=7.0 Hz, 3H), 0.44 (s, 3H), 0.41 (s, 3H); $^{13}$C NMR (125 MHz, CDCl$_3$) δ 152.6, 143.9, 135.3, 130.8, 129.9, 128.7, 127.9, 127.3, 127.3, 123.9, 84.2, 1.4, 0.7; IR (CH$_2$Cl$_2$) 3057 (m), 2964 (m), 2874 (m), 1447 (m), 1265 (s), 1181 (m), 1136 (m), 1042 (s), 1016 (s), 862 (s), 822 (s), 793 (s), 740 (s), 702 (s), 656 (m) cm$^{-1}$; HRMS (CI$^+$) m/z calculated for C$_{12}$H$_{20}$NOSi [M+H]$^+$ 222.1236, found 222.1233.

Example 19. 3-Butyl-1,1-diethyl-1,3-dihydro-[1,2] oxasilolo[3,4-c]pyridine (3b)

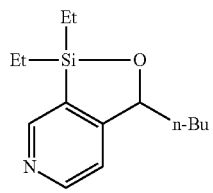

1-(3-Bromopyridin-4-yl)pentan-1-ol (S7) (1.00 g, 4.10 mmol, 1.00 equiv) was dissolved in THF (27.4 mL) and n-BuLi (4.4 mL, 2.05 M in hexanes, 9.02 mmol, 2.20 equiv) was added dropwise at −78° C. The reaction mixture was stirred for 30 min, followed by the addition of Et$_2$SiHCl (1.12 mL, 9.02 mmol, 2.20 equiv) at −78° C. The resulting reaction mixture was allowed to warm to room temperature and stirred for 12 h. The slurry was quenched with H$_2$O (20 mL) with vigorous evolution of H$_2$ gas observed. The solution was allowed to stir for 5 h and extracted with EtOAc (3×20 mL). The combined organic layers were collected and washed with 1M aq. HCl (3×40 mL). The acidic aqueous layers were collected and neutralized to pH 8-9 with 1M aq. NaOH (120 mL) producing a white turbid mixture that was extracted with Et$_2$O (3×75 mL). The combined organic layers were dried (MgSO$_4$), filtered and concentrated under reduced pressure. Flash chromatography on silica (30% EtOAc in hexanes) followed by Kugelrohr distillation (130° C., 0.01 mmHg) provided 3b (540 mg, 2.17 mmol, 43% yield) as a yellow oil: R$_f$ 0.2 (40% EtOAc in hexanes); $^1$H NMR (500 MHz, CDCl$_3$) δ 8.69 (bs, 1H), 8.50 (d, J=5.0 Hz, 1H), 7.09 (d, J=5.0 Hz, 1H), 5.12 (dd, J=7.8 Hz, J=3.4 Hz, 1H), 1.84 (m, 1H), 1.51 (m, 1H), 1.44-1.24 (m, 4H), 0.93 (t, J=7.5 Hz, 3H), 0.88-0.77 (m, 10H); $^{13}$C NMR (125 MHz, CDCl$_3$) δ 162.9, 152.6, 149.7, 129.0, 117.7, 81.3, 38.0, 27.4, 22.6, 13.9, 7.09, 6.93, 6.55, 6.26; IR (CH$_2$Cl$_2$) 3057 (m), 2964 (m), 2874 (m), 1447 (m), 1265 (s), 1181 (m), 1136 (m), 1042 (s), 1016 (s), 862 (s), 822 (s), 793 (s), 740 (s), 702 (s), 656 (m) cm$^{-1}$; HRMS (CI$^+$) m/z calculated for C$_{14}$H$_{24}$NOSi [M+H]$^+$ 250.1549, found 250.1547.

Example 20. (2-Bromophenyl)(3-(dimethylamino)phenyl)methanol (S8)

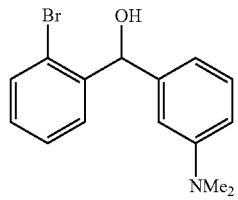 [SMILES: CN(C)c1cccc(C(O)c2ccccc2Br)c1]

In a two-necked 200 mL round-bottom flask, Mg turnings (5.30 g, 216 mmol, 10.0 equiv) were flame-dried under vacuum. Upon cooling to room temperature, THF (55 mL), 3-bromo-N,N-dimethylaniline (6.50 g, 32.4 mmol, 1.50 equiv) as a solution in THF (55 mL) and a crystal of I$_2$ were added. The flask was fitted with a reflux condenser and the solution vigorously stirred. Once the resulting exotherm had subsided, the reaction mixture was heated to reflux (70° C.) for 1 h. This Grignard reagent was then allowed to cool to room temperature and added to a cooled solution of 2-bromobenzaldehyde (4.00 g, 21.6 mmol, 1.00 equiv) in THF (32 mL) at 0° C. via cannula over 10 min. The reaction mixture was then allowed to reach room temperature and stirred for 12 h and quenched with sat. aq. NH$_4$Cl (75 mL). The aqueous phase was then extracted with EtOAc (3×50 mL). The combined organic layers were washed with brine, dried (Na$_2$SO$_4$) and concentrated under reduced pressure. Flash chromatography on silica (1% to 5% EtOAc in hexanes) provided the desired (2-bromophenyl)(3-(dimethylamino)phenyl)methanol (S8) (6.36 g, 20.8 mmol, 96% yield) a yellow viscous oil: R$_f$ 0.4 (20% EtOAc in hexanes); $^1$H NMR (500 MHz, CDCl$_3$) δ 7.59 (dd, J=7.7, 1.6 Hz, 1H), 7.53 (dd, J=7.9, 1.1 Hz, 1H), 7.33 (td, J=7.5, 1.0 Hz, 1H), 7.20 (t, J=7.9, 1H), 7.13 (td, J=7.7, 1.6 Hz, 1H), 6.84 (bs, 1H), 6.72 (d, J=7.5, 1H), 6.66 (dd, J=8.2, 2.2 Hz, 1H), 6.16 (s, 1H), 2.93 (s, 6H), 2.38 (bs, 1H); $^{13}$C NMR (125 MHz, CDCl$_3$) δ 150.8, 143.3, 142.9, 132.9, 129.3, 129.1, 128.7, 127.8, 123.1, 115.3, 112.2, 111.4, 75.3, 40.8; IR (neat) 3392 (bs), 2917 (s), 2848 (s), 1604 (s), 1498 (s), 1437 (s), 1353 (s), 1018 (m), 996 (s), 744 (s) cm$^{-1}$; HRMS (ES$^+$) m/z calculated for C$_{15}$H$_{17}$NOBr [M+H]$^+$ 306.0494, found 306.0492.

Example 21. 3-(1,1-Dimethyl-1,3-dihydrobenzo[c][1,2]oxasilol-3-yl)-N,N dimethylaniline (3c)

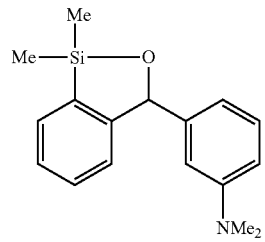 [SMILES: CN(C)c1cccc(C2O[Si](C)(C)c3ccccc32)c1]

(2-Bromophenyl)(3-(dimethylamino)phenyl)methanol (S8) (6.90 g, 22.5 mmol, 1.00 equiv) was dissolved in THF (90 mL) and n-BuLi (20.8 mL, 2.40 M in hexanes, 50.0 mmol, 2.20 equiv) was added dropwise at −78° C. The reaction mixture was stirred for 45 min, followed by the addition of Me$_2$SiHCl (5.60 mL, 50.0 mmol, 2.20 equiv) at −78° C. The resulting reaction mixture was allowed to warm to room temperature and stirred for 12 h. The slurry was quenched with H$_2$O (75 mL) with vigorous evolution of H$_2$ gas observed. The reaction mixture was allowed to stir for 5 h and extracted with EtOAc (3×50 mL). The combined organic layers were collected and washed with 3M aq. HCl (3×50 mL). The acidic aqueous layers were collected and neutralized to pH 8-9 with 1M aq. NaOH producing a white turbid mixture that was extracted with Et$_2$O (3×75 mL). The combined organic layers were dried (MgSO$_4$), filtered and concentrated under reduced pressure. Flash chromatography on silica (5% to 10% EtOAc in hexanes) followed by Kugelrohr distillation (150° C., 0.01 mmHg) provided 3c (2.8 g, 9.88 mmol, 44% yield) as an orange viscous oil: R$_f$ 0.1 (40% EtOAc in hexanes); $^1$H NMR (500 MHz, CDCl$_3$) δ 7.63 (dd, J=6.2, 1.6 Hz, 1H), 7.33 (m, 2H), 7.22 (t, J=7.6 Hz, 1H), 7.13 (d, J=7.4 Hz, 1H), 6.71-6.62 (m, 3H), 6.15 (s, 1H), 2.94 (s, 6H), 0.56 (s, 3H), 0.48 (s, 3H); $^{13}$C NMR (125 MHz, CDCl$_3$) δ 152.8, 150.88, 144.71, 135.04, 130.6, 129.9, 129.3, 127.3, 127.1, 123.8, 115.6, 112.2, 111.6, 84.7, 40.7, 1.51, 0.65; IR (neat) 2953 (bs), 2874 (bs), 2802 (s), 1605 (s), 1499 (s), 1440 (s), 1353 (s), 1251 (s), 1135 (s), 1066 (s), 1043 (s), 995 (s), 870 (s), 789 (s), 743 (s) cm$^{-1}$; HRMS (ES$^+$) m/z calculated for C$_{17}$H$_{22}$NOSi [M+H]$^+$ 284.1471, found 284.1476.

Example 22.
(2-Bromophenyl)(4-(dimethylamino)phenyl)methanol (S9)

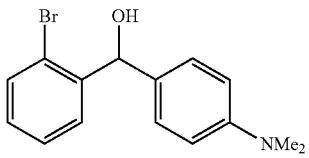 [SMILES: CN(C)c1ccc(C(O)c2ccccc2Br)cc1]

In a two-necked 500 mL round-bottom flask, Mg turnings (10.5 g, 432 mmol, 10.0 equiv) were flame-dried under vacuum. Upon cooling to room temperature, THF (72 mL), 4-bromo-N,N-dimethylaniline (12.9 g, 64.9 mmol, 1.50 equiv) as a solution in THF (72 mL) and a crystal of I$_2$ were added. The flask was fitted with a reflux condenser and the solution was vigorously stirred. Once the resulting exotherm had subsided, the reaction mixture was heated to reflux (70° C.) for 1 h. This Grignard reagent was then allowed to cool to room temperature and added to a cooled solution of 2-bromobenzaldehyde (8.00 g, 43.2 mmol, 1.00 equiv) in THF (87 mL) at 0° C. via cannula over 10 min. The reaction was then allowed to reach room temperature and stirred for 12 h and quenched with sat. aq. NH$_4$Cl (100 mL). The aqueous phase was then extracted with EtOAc (3×50 mL). The combined organic layers were washed with brine, dried (Na$_2$SO$_4$) and concentrated under reduced pressure. Flash chromatography on silica (3% to 10% EtOAc in hexanes) provided of the desired (2-bromophenyl)(4-(dimethylamino)phenyl)methanol (S9) (12.6 g, 41.2 mmol, 95% yield) as a blue crystalline solid: R$_f$0.2 (10% EtOAc in hexanes); $^1$H NMR (500 MHz, CDCl$_3$) δ 7.71 (dd, J=7.7, 1.5 Hz, 1H), 7.53 (dd, J=7.9, 1.0 Hz, 1H), 7.37 (td, J=7.6, 1.0 Hz, 1H), 7.24 (m, 2H), 7.14 (td, J=7.7, 1.5 Hz, 1H), 6.69 (m, 2H), 6.07 (s, 1H), 2.94 (s, 6H), 2.58 (bs, 1H); $^{13}$C NMR (125 MHz, CDCl$_3$) δ 150.3, 143.2, 132.9, 130.3, 128.8, 128.6, 128.4, 128.3, 127.7, 122.8, 112.8, 112.6, 112.3, 74.8, 40.7; IR (neat) 3387 (bs), 2887 (m), 2802 (s), 1613 (s), 1521 (s), 1352 (s), 1162 (s), 1017 (m), 810 (s), 758 (s), 741 (s) cm$^{-1}$; HRMS (ES$^+$) m/z calculated for C$_{15}$H$_{17}$NOBr [M+H]$^+$ 306.0494, found 306.0497.

Example 23. 4-(1,1-Dimethyl-1,3-dihydrobenzo[c][1,2]oxasilol-3-yl)-N,N-dimethylaniline (3f)

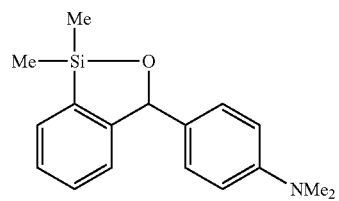 [SMILES: CN(C)c1ccc(C2O[Si](C)(C)c3ccccc32)cc1]

(2-Bromophenyl)(4-(dimethylamino)phenyl)methanol (S9) (2.33 g, 7.61 mmol, 1.00 equiv) was dissolved in THF (25 mL) and n-BuLi (7.6 mL, 2.20 M in hexanes, 16.7 mmol, 2.20 equiv) was added dropwise at −78° C. The reaction mixture was stirred for 45 min, followed by the addition of Me$_2$SiHCl (2.00 mL, 16.7 mmol, 2.20 equiv) at −78° C. The resulting reaction mixture was allowed to warm to room temperature and stirred for 12 h. The slurry was quenched with H$_2$O (50 mL) with vigorous evolution of H$_2$ gas observed. The reaction mixture was allowed to stir for 5 h and extracted with EtOAc (3×25 mL). The combined organic layers were collected and washed with 3M aq. HCl (3×25 mL). The acidic aqueous layers were collected and neutralized to pH 8-9 with 1M aq. NaOH producing a white turbid mixture that was extracted with Et$_2$O (3×75 mL). The combined organic layers were dried (MgSO$_4$), filtered and concentrated under reduced pressure. Flash chromatography on silica (5% Et$_2$O in hexanes) provided 3f (795 mg, 2.81 mmol, 37% yield) as an yellow crystalline solid: R$_f$0.1 (25% EtOAc in hexanes); $^1$H NMR (500 MHz, CDCl$_3$) δ 7.63 (dd, J=6.0, 1.8 Hz, 1H), 7.33 (m, 2H), 7.14 (m, 2H), 7.06 (m, 1H), 6.72 (m, 2H), 6.14 (s, 1H), 2.95 (s, 6H), 0.52 (s, 3H), 0.46 (s, 3H); $^{13}$C NMR (125 MHz, CDCl$_3$) δ 153.3, 150.5, 135.5, 132.1, 130.6, 129.8, 128.5, 128.3, 127.1, 124.1, 112.7, 84.2, 40.8, 1.57, 0.66; IR (neat) 3419 (bs), 2921 (m), 1615 (s), 1523 (s), 1443 (s), 1348 (s), 1251 (s), 1163 (s), 1134 (s), 861 (s), 822 (s), 789 (s), 743 (s) cm$^{-1}$; HRMS (CI$^+$) m/z calculated for C$_{17}$H$_{22}$NOSi [M+H]$^+$ 284.1471, found 284.1459.

Example 24. 4-(1,1-Diethyl-1,3-dihydrobenzo[c][1,2]oxasilol-3-yl)-N,N-dimethylaniline (3g)

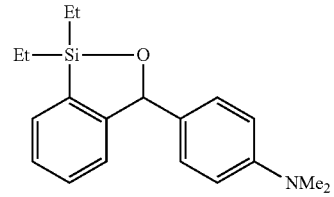 [SMILES: CC[Si]1(CC)OC(c2ccc(N(C)C)cc2)c2ccccc21]

(2-Bromophenyl)(4-(dimethylamino)phenyl)methanol (S9) (7.00 g, 22.9 mmol, 1.00 equiv) was dissolved in THF (230 mL), n-BuLi (22.9 mL, 2.20 M in hexanes, 50.4 mmol, 2.20 equiv) was added dropwise at −78° C. The reaction mixture was stirred for 45 min, followed by the addition of Et$_2$SiHCl (7.00 mL, 50.4 mmol, 2.20 equiv) at −78° C. The resulting reaction mixture was allowed to warm to room temperature and stirred for 12 h. The slurry was quenched with H$_2$O (100 mL) with vigorous evolution of H$_2$ gas observed. The reaction mixture was allowed to stir for 5 h and extracted with EtOAc (3×50 mL). The combined organic layers were collected and washed with 3M aq. HCl (3×50 mL). The acidic aqueous layers were collected and neutralized to pH 8-9 with 1M aq. NaOH (300 mL) producing a white turbid mixture that was extracted with Et$_2$O (3×100 mL). The combined organic layers were dried (MgSO$_4$), filtered and concentrated under reduced pressure. Flash chromatography on silica (5% EtOAc in hexanes) provided 3g (3.6 g, 11.6 mmol, 51% yield) as an yellow oil: R$_f$0.3 (15% EtOAc in hexanes); $^1$H NMR (500 MHz, CDCl$_3$) δ 7.64 (dd, J=6.0, 1.5 Hz, 1H), 7.37-7.30 (m, 2H), 7.17-7.15 (m, 2H), 7.06 (m, 1H), 6.74-6.70 (m, 2H), 6.15 (s, 1H), 2.95 (s, 6H), 1.08 (m, 3H), 1.04-0.88 (m, 7H); $^{13}$C NMR (125 MHz, CDCl$_3$) δ 153.8, 150.4, 133.8, 132.0, 131.2, 129.7, 128.7, 126.8, 124.1, 112.5, 84.3, 40.7, 7.43, 7.11, 6.99, 6.65; IR (neat) 2955 (m), 2875 (m), 2800 (s), 1614 (s), 1523 (s), 1444 (m), 1348 (s), 1230 (s), 1162 (s), 1132 (s), 997 (m), 949 (s), 823 (m), 723 (m) cm$^{-1}$; HRMS (ES$^+$) m/z calculated for C$_{19}$H$_{26}$NOSi [M+H]$^+$ 312.1784, found 312.1783.

Example 25. General Procedure A

To a cooled solution of siloxane (0.81 mmol, 1.8 equiv) in dry Et$_2$O (1.2 mL) at room temperature was added a solution of PhLi in Bu$_2$O (0.68 mmol, 1.5 equiv) and allowed to stir for 2 h. After 1.5 h had elapsed following PhLi addition, in a separate flask were combined PdCl$_2$ (2.50 mg, 0.014 mmol, 0.03 equiv), CuI (8.60 mg, 0.045 mmol, 0.1 equiv) and dpca (6.7 mg, 0.018 mmol, 0.04 equiv) in dry THF (1 mL) at room temperature and stirred for 30 min. The aryl halide (0.45 mmol, 1.0 equiv) was added to the orange slurry, followed by addition of the siloxane/PhLi reaction mixture by cannula (flask rinsed with 0.5 mL of THF). After 2 h at room temperature, the reaction mixture was diluted with Et$_2$O (2 mL) and quenched according to the siloxane used in the reaction; 1, 1a-f, 2a-d quenched with sat. aq. NH$_4$Cl (5 mL); 3a-b and 3d-e quenched with 1M aq. HCl (5 mL); 3c and 3f-g quenched with 3M aq. HCl (5 mL).

For siloxanes 1, 1a-f, 2a-d the aqueous layer was extracted with Et$_2$O (3×5 mL) and the combined organic layers were dried (MgSO$_4$), filtered, and concentrated under reduced pressure. Flash chromatography provided the cross-coupled product and the recovered siloxane (where possible as with siloxanes 2a-d).

For siloxanes 3a-g, the organic layer was washed with either 1M or 3M aq. HCl (3×5 mL) (according to siloxane, see above), and the acidic aqueous layers were collected. The organic layer was then washed with sat. aq. NaHCO$_3$ (5 mL), dried (MgSO$_4$), filtered, and concentrated under reduced pressure. Flash chromatography provided the cross-coupled product. The acidic aqueous layer was then basified to pH 8-9 with 1M aq. NaOH, producing a white turbid mixture that was then extracted with Et$_2$O 3×50 mL). The combined organic layers were dried (MgSO$_4$), filtered, and concentrated under reduced pressure to provide the recovered siloxane.

Example 26. Preparation of Fluorinated Siloxanes

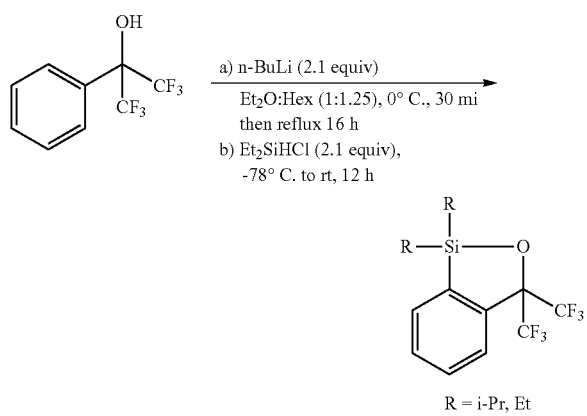

Procedure:

To a cooled solution of (Hexafluoro-2-hydroxyisopropyl)benzene (3.00 g, 12.3 mmol, 1.00 equiv) in hexanes (75 mL, pre-dried over MgSO$_4$) and Et$_2$O (60 mL) at 0° C. was added n-BuLi (12.6 mL, 2.15 M in hexanes, 27.1 mmol, 2.20 equiv) dropwise under N$_2$. The reaction mixture was warmed to room temperature and stirred for 30 minutes. The flask was then fitted with a reflux condenser and the reaction mixture was heated to reflux (70° C.) for 16 h. A dark brown solution resulted and the reaction mixture was allowed to cool to room temperature. The reflux condenser was removed and the reaction mixture was cooled to −78° C. before either i-Pr$_2$SiHCl (4.60 mL, 27.06 mmol, 2.20 equiv) or Et$_2$SiHCl was added dropwise under N$_2$. The reaction mixture was allowed to slowly warm to room temperature and stirred for 12 h. The resulting pale yellow slurry was then quenched with H$_2$O (75 mL) and the aqueous phase extracted with Et$_2$O (3×40 mL). The combined organic layers were washed with brine, dried (MgSO$_4$), filtered and concentrated under reduced pressure. Flash chromatography (100% hexanes) provided 2.76 g (63% yield) of the desired diisopropyl siloxane as a white crystalline solid (m.p. 39-41° C.).

Example 27

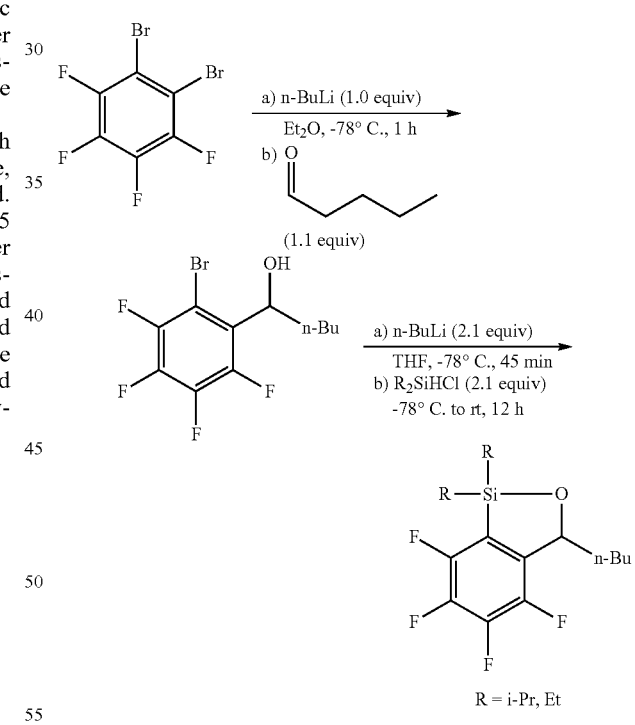

Procedure:

To a cooled solution of 1,2-Dibromotetrafluorobenzene (5.00 g, 16.2 mmol, 1.00 equiv) in Et$_2$O (162 mL) at −78° C. was added n-BuLi (7.75 mL, 2.10 M in hexanes, 16.2 mmol, 1.00 equiv) dropwise over 30 min under N$_2$. The reaction mixture was stirred for another 30 minutes before pentanal (1.90 mL, 17.9 mmol, 1.10 equiv) was added dropwise. The reaction mixture was stirred for 5 h at −78° C. before it was warmed to 0° C. and quenched with H$_2$O (75 mL). The aqueous phase extracted with Et$_2$O (3×30 mL). The combined organic layers were washed with brine, dried (MgSO$_4$), filtered and concentrated under reduced pressure. Flash chromatography (2% to 5% ethyl acetate in hexanes) provided 4.34 g (85% yield) of the perfluorinated bromo benzylic alcohol.

The resulting perfluorinated bromo benzylic alcohol (332 mg, 1.05 mmol, 1.00 equiv) was dissolved in THF (5.5 mL) and n-BuLi (1.1 mL, 2.10 M in hexanes, 2.21 mmol, 2.10 equiv) was added dropwise at −78° C. The reaction mixture was stirred for 45 min followed by the addition of either iPr$_2$SiHCl (0.40 mL, 2.32 mmol, 2.20 equiv) or Et$_2$SiHCl at −78° C. The resulting reaction mixture was allowed to warm to room temperature and stirred for 12 h. The reaction mixture was quenched by addition of H$_2$O (20 ml) and stirred for 1 h. The aqueous phase was then extracted with Et$_2$O (2×15 mL) and the combined organic layers were washed with brine, dried (MgSO$_4$), and concentrated under reduced pressure. Flash chromatography (100% hexanes) provided the desired siloxane (223 mg, 61% yield) as a light yellow oil.

Example 28. 4-Methoxy-1,1'-bipheny (S10)

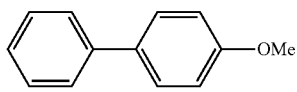 [SMILES: COc1ccc(-c2ccccc2)cc1]

Following General Procedure A, the product was purified by chromatography on SiO$_2$ (1% EtOAc in hexanes) to afford S7 (80.0 mg, 0.43 mmol, 96% with siloxane 2a; 81.0 mg, 0.44 mmol, 98% with siloxane 2b; 81.0 mg, 0.44 mmol, 98% with siloxane 3e; 81.0 mg, 0.44 mmol, 98% with siloxane 3g) as a colorless solid. Analytical data matches that which has been previously reported for S10:[11] R$_f$ 0.5 (1% EtOAc in hexanes); $^1$H NMR (500 MHz, CDCl$_3$) δ 7.57-7.53 (m, 4H), 7.42 (t, J=7.6 Hz, 2H), 7.31 (t, J=7.4 Hz, 1H), 6.99 (d, J=8.7 Hz, 2H), 3.86 (s, 3H); $^{13}$C NMR (125 MHz, CDCl$_3$) δ 159.3, 141.0, 133.9, 128.9, 128.3, 126.9, 126.8, 114.3, 55.5.

Example 29. [1,1'-Biphenyl]-4-carbonitrile (S11)

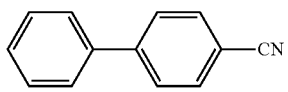 [SMILES: N#Cc1ccc(-c2ccccc2)cc1]

Following General Procedure A, the product was purified by chromatography on SiO$_2$ (1% EtOAc in hexanes) to afford S8 (74.0 mg, 0.41 mmol, 92% with siloxane 2a; 73.0 mg, 0.40 mmol, 91% with siloxane 2b; 77.0 mg, 0.43 mmol, 96% with siloxane 3e; 75.0 mg, 0.42 mmol, 94% with siloxane 3g as a colorless solid. Analytical data matches that which has been previously reported for S11:[12] R$_f$ 0.3 (1% EtOAc in hexanes); $^1$H NMR (500 MHz, CDCl$_3$) 7.73 (d, J=8.3 Hz, 2H), 7.69 (d, J=8.4 Hz, 2H), 7.59 (d, J=7.4 Hz, 2H), 7.49 (t, J=7.2 Hz, 2H), 7.43 (t, J=7.3 Hz, 1H); $^{13}$C NMR (125 MHz, CDCl$_3$) δ 145.8, 139.3, 132.8, 129.3, 128.8, 127.9, 127.4, 119.1, 111.1.

Example 30. General Procedure B

To a solution of alkenyl iodide or aryl iodide (0.68 mmol, 1.50 equiv) in Et$_2$O (1 mL) at −78° C. was added t-BuLi in pentane (1.35 mmol, 3.00 equiv), and a white or yellow (depending on alkenyl iodide or aryl idodide) slurry developed. The reaction mixture was allowed to stir for 40 min at −78° C. and 20 min at room temperature, at which time a solution of siloxane (0.81 mmol, 1.80 equiv) in THF (0.5 mL+0.2 mL rinse) was added and allowed to stir at room temperature for 2 h. After 1.5 h had elapsed following siloxane addition, in a separate flask were combined PdCl$_2$ (2.50 mg, 0.014 mmol, 0.03 equiv), CuI (8.60 mg, 0.045 mmol, 0.1 equiv) and dpca (6.7 mg, 0.018 mmol, 0.04 equiv) in dry THF (1 mL) at room temperature and stirred for 30 min. The alkenyl halide or aryl iodide (0.45 mmol, 1.00 equiv) was added as a solution in THF (0.3 mL) to the orange slurry, immediately followed by addition of the siloxane reaction mixture by cannula (flask rinsed with 0.5 mL of THF). After 2-12 h at room temperature, the reaction mixture was diluted with Et$_2$O (2 mL) and quenched according to the siloxane used in the reaction; 1, 1a-f, 2a-d quenched with sat. aq. NH$_4$Cl (5 mL); 3a-b and 3d-e quenched with 1M aq. HCl (5 mL); 3c and 3f-g quenched with 3M aq. HCl (5 mL).

For siloxanes 1, 1a-f, 2a-d, the aqueous layer was extracted with Et$_2$O (3×5 mL) and the combined organic layers were dried (MgSO$_4$), filtered, and concentrated under reduced pressure. Flash chromatography provided the cross-coupled product and the recovered siloxane (where possible as with siloxanes 2a-d).

For siloxanes 3a-g, the organic layer was washed with either 1M or 3M aq. HCl (3×5 mL) (according to siloxane, see above), and the acidic aqueous layers were collected. The organic layer was then washed with sat. aq. NaHCO$_3$ (5 mL), dried (MgSO$_4$), filtered, and concentrated under reduced pressure. Flash chromatography provided the cross-coupled product. The acidic aqueous layer was then basified to pH 8-9 with 1M aq. NaOH, producing a white turbid mixture which was then extracted with Et$_2$O 3×50 mL). The combined organic layers were dried (MgSO$_4$), filtered, and concentrated under reduced pressure to provide the recovered siloxane.

Example 31. (E)-tert-Butyl((3-(4-methoxyphenyl) allyl)oxy)dimethylsilane (S12)

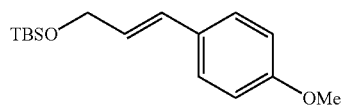 [SMILES: COc1ccc(/C=C/CO[Si](C)(C)C(C)(C)C)cc1]

Following General Procedure B, the product was purified by chromatography on SiO$_2$ (1% EtOAc in hexanes) to afford S9 in >20:1 E/Z ratio as a colorless oil (110 mg, 0.40 mmol, 88% with siloxane 2a; 115 mg, 0.41 mmol, 92% with siloxane 2b; 124 mg, 0.44 mmol, 99% with siloxane 3e; 121 mg, 0.44 mmol, 97% with siloxane 3g). Analytical data matches that which has been previously reported for S12:[13] R$_f$ 0.3 (1% EtOAc in hexanes); $^1$H NMR (500 MHz, CDCl$_3$) δ 7.31 (d, J=8.8 Hz, 2H), 6.85 (d, J=8.8 Hz, 2H), 6.53 (d, J=16.0 Hz, 1H), 6.15 (dt, J=5.2, 16.0 Hz, 1H), 4.33 (d, J=5.3 Hz, 2H), 3.81 (s, 3H), 0.94 (s, 9H), 0.11 (s, 6H); $^{13}$C NMR (125 MHz, CDCl$_3$) δ 159.2, 130.1, 129.3, 127.7, 127.1, 114.07, 64.2, 55.4, 26.1, 18.6, −4.97.

Example 32. tert-Butyldimethyl(((2E,4E)-7-phenyl-hepta-2,4-dien-1-yl)oxy)silane (S13)

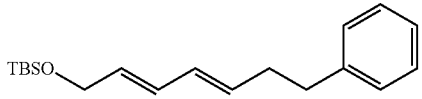 [SMILES: CC(C)(C)[Si](C)(C)OC/C=C/C=C/CCc1ccccc1]

Following General Procedure B, the product was purified by chromatography on SiO$_2$ (1% EtOAc in hexanes) to afford S13 in >20:1 E/Z ratio as a colorless oil (125 mg, 0.41 mmol, 92% with siloxane 2a; 124 mg, 0.41 mmol, 91% with siloxane 2b; 131 mg, 0.43 mmol, 96% with siloxane 3e; 135 mg, 0.44 mmol, 99% with siloxane 3g): R$_f$ 0.3 (1% EtOAc in hexanes); $^1$H NMR (500 MHz, CDCl$_3$) δ 7.31-7.25 (m, 2H), 7.21-7.17 (m, 3H), 6.19 (dd, J=10.6, 15.0 Hz, 1H), 6.08 (dd, J=10.6, 15.0 Hz, 1H), 5.75-5.62 (m, 2H), 4.21 (d, J=5.5 Hz, 2H), 2.72 (t, J=7.5 Hz, 2H), 2.41 (q, J=7.5 Hz, 2H), 0.93 (s, 9H), 0.83 (s, 6H); $^{13}$C NMR (125 MHz, CDCl$_3$) δ 141.9, 133.4, 132.4, 130.8, 130.4, 130.3, 129.5, 128.6, 128.5, 126.0, 63.8, 63.7, 35.9, 34.6, 29.9, 26.1, 18.6, −5.01. IR (neat) 3026 (m), 2954 (m), 2930 (s), 2856 (s) 1468 (m), 1254 (s), 1109 (m), 1066 (bs), 988 (s), 837 (s), 776 (s) cm$^{-1}$; HRMS (CI$^+$) m/z calculated for C$_{15}$H$_{21}$OSi [M-C$_4$H$_9$]$^+$ 245.1362, found 245.1368.

Example 33. (E)-1-(Hept-1-en-1-yl)-4-methoxybenzene (S14)

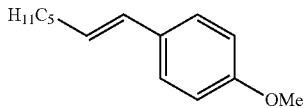

Following General Procedure B, the product was purified by chromatography on SiO$_2$ (1% EtOAc in hexanes) to afford S14 in >20:1 E/Z ratio as a colorless oil (89.0 mg, 0.44 mmol, 97% with siloxane 2a; 88.0 mg, 0.43 mmol, 96% with siloxane 2b; 87.0 mg, 0.43 mmol, 95% with siloxane 3e; 87.0 mg, 0.42 mmol, 94% with siloxane 3g) as a colorless solid. Analytical data matches that which has been previously reported for S14:[14] R$_f$ 0.3 (1% EtOAc in hexanes); $^1$H NMR (500 MHz, CDCl$_3$) δ 7.28 (dd, J=2.0, 6.5 Hz, 2H), 6.84 (dd, J=2.1, 6.6 Hz, 2H), 6.32 (d, J=15.7 Hz, 1H), 6.09 (dt, J=7.2, 15.8 Hz, 1H), 3.80 (s, 3H), 2.18 (qd, J=1.3, 7.3 Hz, 2H), 1.46 (qn, J=7.2 Hz, 2H), 1.40-1.37 (m, 4H), 0.90 (t, J=7.1 Hz, 3H); $^{13}$C NMR (125 MHz, CDCl$_3$) δ 158.6, 131.2, 129.6, 129.5, 127.1, 114.2, 55.7, 33.5, 31.4, 29.5, 22.7, 14.1.

Example 34. (Z)-1-(Hept-1-en-1-yl)-4-methoxybenzene (S15)

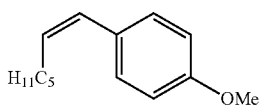

Following General Procedure A, the product was purified by chromatography on SiO$_2$ (1% EtOAc in hexanes) to afford S15 in >20:1 Z/E ratio as a colorless oil (80.0 mg, 0.39 mmol, 87% with siloxane 2a; 82.0 mg, 0.40 mmol, 89% with siloxane 2b; 88.0 mg, 0.43 mmol, 96% with siloxane 3e, 87.0 mg, 0.42 mmol, 94% with siloxane 3g). Analytical data matches that which has been previously reported for S15 (Denmark, S. E.; Sweis, R. F. J. Am. Chem. Soc. 2001, 123, 6439). R$_f$ 0.3 (1% EtOAc in hexanes); $^1$H NMR (500 MHz, CDCl$_3$) δ 7.23 (d, J=8.6 Hz, 2H), 6.87 (d, J=8.8 Hz, 2H), 6.33 (d, J=11.7 Hz, 1H), 5.55 (dt, J=7.3, 11.6 Hz, 1H), 3.82 (s, 3H), 2.29 (qd, J=1.3, 7.3 Hz, 2H), 1.45 (qn, J=7.6 Hz, 2H), 1.36-1.28 (m, 4H), 0.90 (t, J=7.2 Hz, 3H); $^{13}$C NMR (125 MHz, CDCl$_3$) δ 158.6, 131.7, 130.5, 130.1, 128.4, 113.5, 55.1, 31.4, 29.7, 28.9, 22.6, 14.2.

Example 35. Preparation of Siloxane Polymers

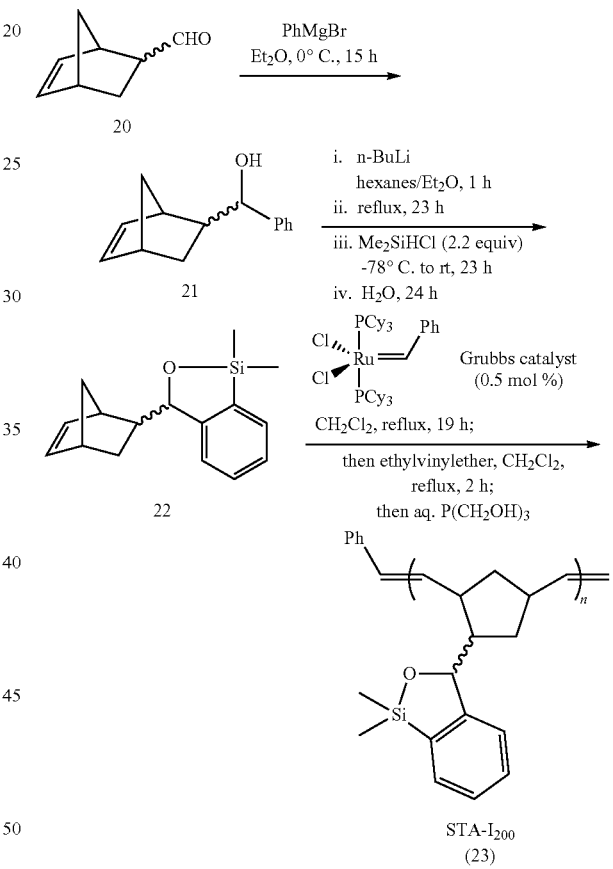

To a stirred solution of aldehyde 20 (5.42 g, 44.4 mmol, mixture of endo and exo isomers) in THF (200 mL) at 0° C. was added solution of PhMgBr in Et$_2$O (17.8 mL, 3.00 M, 53.3 mmol) dropwise. The solution was stirred for 15 h at room temperature and then diluted with sat. aq. NH$_4$Cl (50 mL). The aqueous phase was extracted with Et$_2$O and the combined organic layers were washed with brine, dried with MgSO$_4$, filtered and concentrated under reduced pressure. The crude product was purified by column chromatography on SiO$_2$ (5% Et$_2$O/hexanes) to afford 21 (7.72 g, 87%, mixture of 4 diastereomers) as a pale yellow oil.

To a stirred solution of alcohol 21 (6.83 g, 34.1 mmol) in hexanes (125 mL, dried over MgSO$_4$) and Et$_2$O (100 mL) at 0° C. was added n-BuLi in hexanes 35.8 mL, 2.10 M, 75.1 mmol) dropwise. The solution was stirred at room temperature for 1 h, at which time the solution was heated to reflux for 23 h. The solution was then cooled to −78° C. and Me₂SiHCl (8.16 mL, 75.1 mmol) was added dropwise. The solution was warmed to room temperature, and after 23 h, H₂O (100 mL) was added and the biphasic mixture was stirred for another 24 h. The aqueous phase was extracted with hexanes and the combined organic layers were washed with brine, dried with MgSO₄, filtered and concentrated under reduced pressure. The crude product was purified by column chromatography on SiO₂ (0-1% Et₂O/hexanes; the column was slurry-packed using SiO₂ in H₂O, which was then washed with acetone, EtOAc, and hexanes, successively, prior to chromatographic separation), followed by Kugelrohr distillation at 120-130° C. (0.025 mmHg) to afford 22 as a colorless oil.

Grubbs' 1$^{st}$ generation catalyst (6.1 mg, 7.4 μmol) was dissolved in CH₂Cl₂ (0.5 mL) and the solution was stirred for 30 min. The catalyst solution was then introduced via cannula to another flask containing 22 (378 mg, 1.48 mmol) in CH₂Cl₂ (1 mL), and the resulting solution was then stirred at room temperature. After 17 h, the reaction mixture was heated to reflux. After 19 h, the reaction was quenched with ethylvinylether (0.5 mL) in CH₂Cl₂ (1.5 mL), and heating of the mixture at 50° C. was continued for another 2 h. The solution was then cooled to room temperature and diluted with CH₂Cl₂ (5 mL). Tris(hydroxymethyl)phosphine (53.9 mg, 0.3 eq.) in H₂O (10 mL) was added to the solution and the biphasic mixture was stirred vigorously for 15 min. The aqueous phase was extracted with CH₂Cl₂ and the combined organic layers were washed with brine, dried with MgSO₄, filtered and concentrated under reduced pressure. The obtained white solid was washed extensively with MeCN and dried under vacuum to afford 23 (363 mg, 96%, $M_n$=73689, PDI=1.272) as a white solid. n is about 250.

Example 36. Polymer-Mediated Cross-Coupling

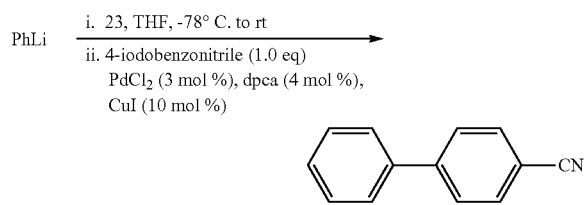

To a stirred solution of polymer 23 (196 mg, see above) in THF (4 mL) at −78° C. was added PhLi in dibutylether (479 μL, 1.23 M, 0.575 mmol) dropwise, followed by THF (6 mL). The reaction mixture was stirred for 3 h at room temperature and a colorless slurry resulted. A mixture of 4-iodobenzonitrile (87.7 mg, 0.383 mmol), PdCl₂ (2.0 mg, 0.011 mmol, 3 mol %), CuI (7.3 mg, 0.038 mmol,), and dpca (N-[2-(Diphenylphosphino)benzylidene]cyclohexylamine, 5.7 mg, 0.015 mmol) was added to the flask in a single portion and the slurry was stirred for 2 d at room temperature. The reaction mixture was diluted with sat. aq. NH₄Cl (5 ml), and the aqueous phase was extracted with Et₂O. The combined organic layers were washed with brine, dried with MgSO₄, filtered and concentrated under reduced pressure. The resulting residue was washed extensively with acetonitrile, and the washings were combined and concentrated to obtain the crude product, which was purified by chromatography on SiO₂ (1% Et₂O/hexanes) to afford the product (26.1 mg, 0.146 mmol, 38%) as a white solid.

Example 37. Alternative Procedure for Polymer-Mediated Cross-Coupling

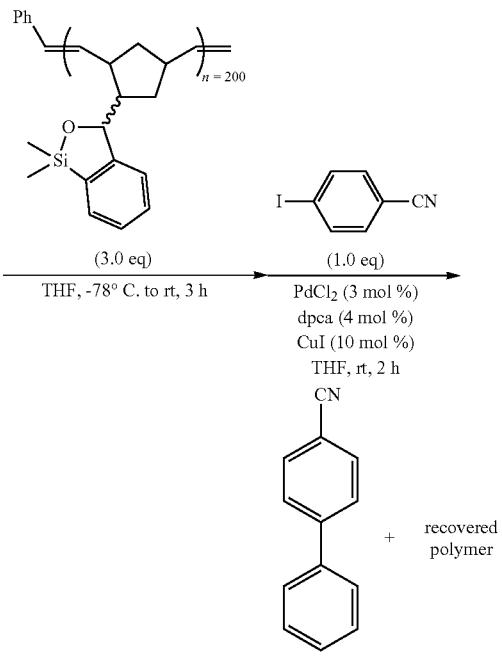

To a cooled solution of siloxane polymer in THF (0.193 g, 0.752 mmol, 3.0 equiv, 10 mg/mL) at −78° C. was added PhLi in Bu₂O (348 μL, 1.8 M, 0.627 mmol, 2.5 equiv) dropwise. The reaction mixture was allowed to warm to rt and was stirred for 3 h, and a white, cloudy solution developed. A solid mixture of PdCl₂ (1.3 mg, 7.5 μmol, 0.03 equiv), CuI (4.8 mg, 0.025 mmol, 0.1 equiv), and dpca (3.7 mg, 0.01 mmol, 0.04 equiv) was combined and added to the reaction flask, followed by addition of 4-iodobenzonitrile (56.8 g, 0.248 mmol, 1.0 equiv). The obtained reaction mixture was stirred vigorously at rt. Care should be taken so that all reactants are submerged in THF and no solid is deposited on the side of the flask. After 2 h, the reaction mixture was quenched with sat. aq. NH₄Cl (5 mL), followed by addition of d.i. H₂O (5 mL). The organic layer was collected and the aqueous layer was extracted with Et₂O (2×10 mL). The combined organic layers were washed with brine, dried with MgSO₄, and concentrated in vacuo to 1-2 mL in volume. The obtained concentrated solution was added dropwise into a vigorously stirred solution of CH₃CN (250 mL). The precipitated polymer was filtered and the supernatant was concentrated in vacuo to provide the crude product. Following removal from the supernatant, the polymer was re-dissolved in DCM (20 mL) and filter through a glass fritted funnel to remove insoluble particles, if there is any. The obtained solution was then concentrated in vacuo to provide the recovered polymer (192 mg, 99% recovery). The crude product was purified by chromatography on SiO₂ (2% Et₂O/hexanes) to afford 4-cyanobiphenyl (40.3 mg, 0.225 mmol, 91%) as a colorless solid.

Example 38. General Cross-Coupling Reaction Procedure

To a cooled solution of siloxane (117 mg, 0.805 mmol) in dry THF (1.0 mL) at −78° C. was added a solution of PhLi in Bu$_2$O (0.67 mmol). The reaction mixture was allowed to warm to room temperature and was stirred for 1 h. After 30 min had elapsed following PhLi addition, in a separate flask were combined PdCl$_2$ (2.4 mg, 0.013 mmol), CuI (8.6 mg, 0.045 mmol) and dpca (6.8 mg, 0.018 mmol) in dry THF (1.0 mL) at room temperature and stirred for 30 min. The aryl halide (0.45 mmol) was added to the orange slurry, followed by cannulation of the siloxane/PhLi reaction mixture (flask rinsed with 0.5 mL THF). After 2 h at room temperature, the reaction mixture was diluted with Et$_2$O (2 mL), quenched with sat. aq. NH$_4$Cl (5 mL) and extracted with Et$_2$O (3×5 mL). The combined organic layers were dried (MgSO$_4$), filtered and concentrated under reduced pressure. The cross-coupled product was purified using column chromatography on SiO$_2$.

Example 39. Siloxane-Mediated Cross-Coupling of 4-Chloroanisole and Phenyllithium Using Palladium To a small pear-shaped flask containing a stirring solution of siloxane 2a (223.6 mg, 0.5 mmol, 1.8 equiv) and THF (0.35 mL) at −78° C. under inert atmosphere, was added PhLi (1.75 M in dibutyl ether, 0.43 mL, 0.75 mmol, 1.5 equiv) dropwise via syringe. The resulting yellow solution (viscous when cold) was allowed to reach room temperature and stirred for 2 h (nucleophile solution). Another flask containing Pd(OAc)$_2$ (11.2 mg, 0.05 mmol, 10 mol %) and XPhos (47.7 mg, 0.1 mmol, 20 mol %) under nitrogen atmosphere was charged with THF (2 mL). This mixture was stirred at room temperature for 20 minutes, turning dark red (catalyst solution). Then, to a round-bottomed flask containing 4-chloroanisole (71.0 mg, 0.5 mmol, 1.0 equiv) under nitrogen atmosphere, were added sequentially catalyst solution and nucleophile solution via syringe and the resulting mixture was stirred at room temperature overnight. The solution was concentrated in vacuo and filtered through a short plug of silica gel eluting with ether. The filtrate was again concentrated in vacuo and subjected to column chromatography eluting with ether/hexanes (0-5%) to afford 4-methoxy-biphenyl (69 mg, 75% yield) with 87% purity as determined by $^1$H-NMR. Impurities include: biphenyl and residual siloxane.

Example 40. Alternative Procedure for Siloxane-Mediated Cross-Coupling of 4-Chloroanisole and Phenyllithium To a small pear-shaped flask containing a stirring solution of siloxane 2a (447.2 mg, 1.8 mmol, 1.8 equiv) and THF (0.7 mL) at −78° C. under inert atmosphere, was added PhLi (1.75 M in dibutyl ether, 0.86 mL, 1.5 mmol, 1.5 equiv) dropwise via syringe. The resulting yellow solution (viscous when cold) was allowed to reach room temperature and stirred for 2 h (nucleophile solution). Another flask containing Pd(OAc)$_2$ (22.4 mg, 0.1 mmol, 10 mol %) and XPhos (95.4 mg, 0.2 mmol, 20 mol %) under nitrogen atmosphere was charged with THF (2 mL). This mixture was stirred at room temperature for 20 minutes, turning dark red (catalyst solution). Then, to a round-bottomed flask containing 4-chloroanisole (142.6 mg, 1.0 mmol, 1.0 equiv) under nitrogen atmosphere, were added sequentially catalyst solution via syringe and nucleophile solution via cannula and the resulting mixture was stirred at room temperature overnight. The solution was concentrated in vacuo and the residue was directly subjected to column chromatography eluting with dichloromethane/hexanes (1-2%) to afford the product (127.1 mg, 69% yield).

Example 41. Carbon-Nitrogen Bond Formation

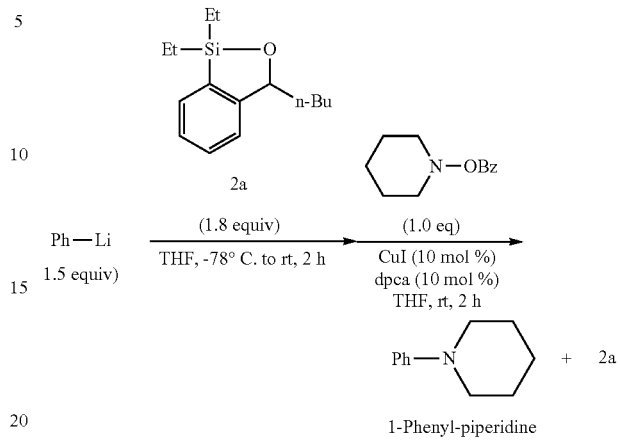

To a cooled solution of siloxane 2a (112.5 mg, 0.453 mmol, 1.8 equiv) in 4 mL THF at −78° C. was added PhLi in Bu$_2$O (210 µL, 0.377 mmol, 1.8 M, 1.5 equiv), dropwise. The reaction mixture was allowed to warm to room temperature (rt) and was stirred for 2 h. A solid mixture of CuI (4.8 mg, 0.025 mmol, 0.1 equiv) and dpca (9.3 mg, 0.025 mmol, 0.1 equiv) was combined and added to the reaction flask, followed by addition of piperidines-1-yl benzoate (51.7 mg, 0.252 mmol, 1.0 equiv). The obtained reaction mixture was stirred at rt. After 2 h, the reaction mixture was quenched with sat. aq. NH$_4$Cl (5 mL), followed by addition of d.i. H$_2$O (5 ml). The organic layer was collected and the aqueous layer was extracted with Et$_2$O (2×10 mL). The combined organic layers were washed with brine, dried with MgSO$_4$, and concentrated in vacuo. Flash chromatography on silica gel (2% Et$_2$O/hexanes) afforded 1-phenyl-piperidine (37.7 mg, 0.234 mmol, 93%) as a colorless oil, and recovered siloxane 2a (97.9 mg, 0.394 mmol, 87%).

Example 42. Polymer-Mediated Carbon-Nitrogen Cross-Coupling

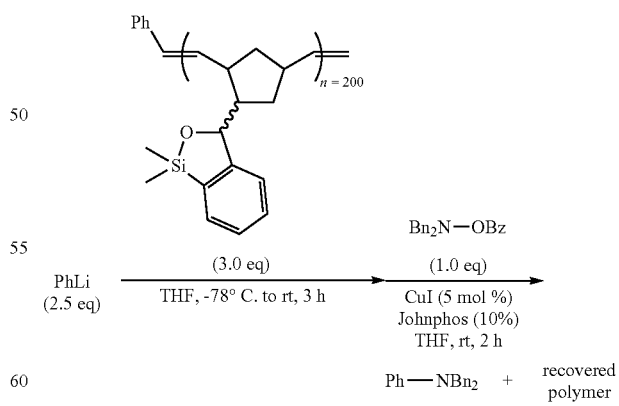

To a cooled solution of siloxane polymer in THF (0.131 g, 0.512 mmol, 3.0 equiv, 10 mg/mL) at −78° C. was added PhLi in Bu$_2$O (237 µL, 1.8 M, 0.627 mmol, 2.5 equiv) dropwise. The reaction mixture was allowed to warm to rt and was stirred for 3 h, and a white, cloudy solution developed. A solid mixture of CuI (1.6 mg, 0.00855 mmol, 0.05 equiv), and Johnphos (5.1 mg, 0.0171 mmol, 0.1 equiv) was combined and added to the reaction flask, followed by addition of O-benzoyl-N,N-dibenzylhydroxylamine (54.3 mg, 0.171 mmol, 1.0 equiv). The obtained reaction mixture was stirred vigorously at rt. Care should be taken so that all reactants are submerged in THF and no solid is deposited on the side of the flask. After 2 h, the reaction mixture was quenched with sat. aq. NH$_4$Cl (5 mL), followed by addition of d.i. H$_2$O (5 mL). The organic layer was collected and the aqueous layer was extracted with Et$_2$O (2×10 mL). The combined organic layers were washed with brine, dried with MgSO$_4$, and concentrated in vacuo to 1-2 mL in volume. The obtained concentrated solution was added dropwise into a vigorously stirred solution of CH$_3$CN (250 mL). The precipitated polymer was filtered and the supernatant was concentrated in vacuo to provide the crude product. Following removal from the supernatant, the polymer was re-dissolved in DCM (20 mL) and filter through a glass fritted funnel to remove insoluble particles, if there is any. The obtained solution was then concentrated in vacuo to provide the recovered polymer (114.2 mg, 87% recovery). The crude product was purified by chromatography on SiO$_2$ (1% Et$_2$O/hexanes) to afford N,N-dibenzylaniline (40.8 mg, 0.149 mmol, 87%) as a colorless solid.

Example 43

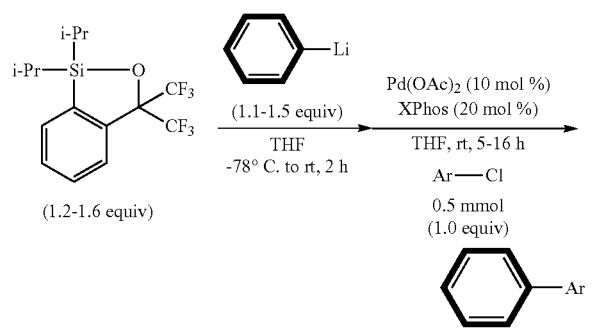

General Procedure A: To a cooled solution of siloxane (0.6-0.8 mmol, 1.2-1.6 equiv) in dry THF (0.25-0.35 mL) at −78° C. was added a solution of PhLi in Bu$_2$O (0.55-0.75 mmol, 1.1-1.5 equiv) and allowed to stir at room temperature for 2 h. After 1.5 h had elapsed following PhLi addition, in a separate flask were combined Pd(OAc)$_2$ (11.2 mg, 0.05 mmol, 0.1 equiv), and XPhos (48 mg, 0.1 mmol, 0.2 equiv) in dry THF (0.75 mL) at room temperature and stirred for 15 min. The aryl chloride (0.5 mmol, 1.0 equiv) was added to the dark red slurry, followed by addition of the siloxane/PhLi reaction mixture by cannula (flask rinsed with 0.25 mL of THF). After 14 h at room temperature, the reaction mixture was diluted with Et$_2$O (2 mL) and quenched with distilled water. The aqueous layer was extracted with Et$_2$O (3×10 mL) and the combined organic layers were dried (MgSO$_4$), filtered, and concentrated under reduced pressure. Flash chromatography provided the cross-coupled product and the recovered siloxane.

Example 44

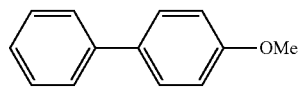 [SMILES: COc1ccc(-c2ccccc2)cc1]

4-Methoxy-1,1'-biphenyl: Following General Procedure A, the product was purified by chromatography on SiO$_2$ (1% EtOAc in hexanes) to afford S10 (88.0 mg, 0.48 mmol, 96% yield as a colorless solid. Analytical data matches that which has been previously reported for 4-methoxy-1,1'-biphenyl: Rf 0.5 (1% EtOAc in hexanes); 1H NMR (500 MHz, CDCl3) δ 7.57-7.53 (m, 4H), 7.42 (t, J=7.6 Hz, 2H), 7.31 (t, J=7.4 Hz, 1H), 6.99 (d, J=8.7 Hz, 2H), 3.86 (s, 3H); 13C NMR (125 MHz, CDCl3) δ59.3, 141.0, 133.9, 128.9, 128.3, 126.9, 126.8, 114.3, 55.5.

Example 45

[1,1'-Biphenyl]-4-carbonitrile: Following General Procedure A, the product was purified by chromatography on SiO$_2$ (1% EtOAc in hexanes) to afford S11 (65.0 mg, 0.36 mmol, 73% yield as a colorless solid. Analytical data matches that which has been previously reported for [1,1'-Biphenyl]-4-carbonitrile: Rf 0.3 (1% EtOAc in hexanes); 1H NMR (500 MHz, CDCl3) 7.73 (d, J=8.3 Hz, 2H), 7.69 (d, J=8.4 Hz, 2H), 7.59 (d, J=7.4 Hz, 2H), 7.49 (t, J=7.2 Hz, 2H), 7.43 (t, J=7.3 Hz, 1H); 13C NMR (125 MHz, CDCl3) δ 145.8, 139.3, 132.8, 129.3, 128.8, 127.9, 127.4, 119.1, 111.1.

Example 46

General Procedure:
To a cooled solution of siloxane (214 mg, 0.6 mmol, 1.2 equiv) in dry THF (0.25 mL) at −78° C. was added a solution of PhLi in a 1.5M solution of Bu$_2$O (0.36 mL, 0.55 mmol, 1.1 equiv) and allowed to stir at room temperature for 2 h. After 1.5 h had elapsed following PhLi addition, in a separate flask were combined Buchwald 4$^{th}$ generation precatalyst (4.3-22 mg, 0.005-0.025 mmol, 0.01-0.05 equiv), XPhos (2.4-12 mg, 0.005-0.025 mmol, 0.01-0.05 equiv), and the aryl chloride (0.5 mmol, 1.0 equiv). This was followed by addition of the siloxane/PhLi reaction mixture by cannula (flask rinsed with an additional 0.25 mL of THF). After 4-24 h at room temperature (utilizing 5 mol % of Buchwald precatalyst) or 60° C. (utilizing 1 mol % of Buchwald precatalyst) the reaction mixture was diluted with Et$_2$O (2 mL) and quenched with distilled water. The aqueous layer was extracted with Et$_2$O (3×10 mL) and the combined organic layers were dried (MgSO$_4$), filtered, and concentrated under reduced pressure. Flash chromatography on silica gel provided the cross-coupled product and the recovered siloxane.

Example 47

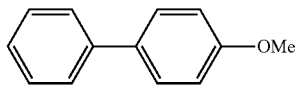

4-Methoxy-1,1'-biphenyl

Following General Procedure A, the product was purified by chromatography on SiO$_2$ (1% EtOAc in hexanes) to afford S10 (88.0 mg, 0.48 mmol, 96% yield as a colorless solid. Analytical data matches that which has been previously reported for S10: Rf 0.5 (1% EtOAc in hexanes); $^1$H NMR (500 MHz, CDCl3) δ 7.57-7.53 (m, 4H), 7.42 (t, J=7.6 Hz, 2H), 7.31 (t, J=7.4 Hz, 1H), 6.99 (d, J=8.7 Hz, 2H), 3.86 (s, 3H); $^{13}$C NMR (125 MHz, CDCl3) δ159.3, 141.0, 133.9, 128.9, 128.3, 126.9, 126.8, 114.3, 55.5.

REFERENCES

[1] Nakao, Y.; Imanaka, H.; Chen, J.; Yada, A.; Hiyama, T. *J. Organomet. Chem.* 2007, 692, 585.
[2] Nakao, Y.; Takeda, M.; Matsumoto, T.; Hiyama, T. *Angew. Chem. Int. Ed.* 2010, 49, 4447.
[3] Spino, C.; Gund, V. G.; Nadeau, C. *J. Comb. Chem.* 2005, 7, 345.
[4] (a) Kunai, A.; Kawakami, T.; Toyoda, K.; Ishikawa, M. *Organometallics,* 1992, 11, 2708. (b) Kunai, A.; Ohshita, J. *J. Orgnomet. Chem.* 2003, 686, 3.
[5] Huang, Z.; Negishi, E. *Org. Lett.* 2006, 8, 3675.
[6] Wang, Z.; Denmark, S. E. *Org. Synth.* 2005, 81, 42.
[7] Smith, A. B., III; Tong, R.; Kim, W.-S.; Maio, W. M, *Angew. Chem. Int. Ed.* 2011, 50, 8904.
[8] Lin, S., Lu, X. *J. Org. Chem.* 2007, 72, 9757.
[9] Bastug, G., Dierick, S., Lebreux, F., Marko, I. E. *Org. Lett.* 2012, 14, 1306.
[10] Harrowven, D. C.; Sutton, B. J.; Coulton, S. *Org. Biomol. Chem.* 2003, 1, 4047.
[11] Manolikakes, G.; Knochel, P. *Angew. Chem. Int. Ed.* 2009, 48, 205.
[12] Kobayashi, O.; Uraguchi, D.; Yamakawa, T. *Org. Lett.* 2009, 11, 2679.
[13] Seki, M.; Mori, K. *Eur. J. Org. Chem.* 1999, 2965.
[14] Denmark, S. E.; Sweis, R. F. *J. Am. Chem. Soc.* 2001, 123, 6439.
[15] Smith, A. B., III et al., J. Am. Chem. Soc. 2012, 134, 4533-4536.
[16] Son, E.-C., et al., Bull. Chem. Soc. Jpn. 2006, 79, 492.
[17] Smith, A. B., III et al. Angew. Chem. Int. Ed. 2011, 50, 8904-8907.

What is claimed:

1. A method of cross-coupling a compound of formula NuLi with a compound of formula E-X to form a compound of formula Nu-E comprising contacting the compound of formula NuLi with the compound of formula E-X in the presence of a catalyst system consisting of palladium and a phosphate ligand, an ethereal solvent, and a compound of Formula I

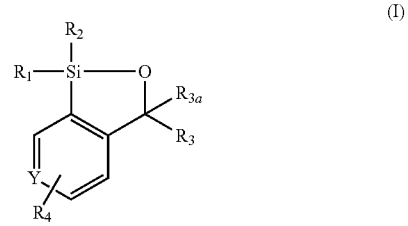

wherein
Y is CH or N;
R$_1$ and R$_2$ are independently C$_{1-10}$ straight or branched-chain alkyl optionally substituted with one or more halogen, nitro, C$_{1-6}$alkoxy, or aryl;
R$_3$ is H;
aryl optionally substituted with one or more nitro, diC$_{1-6}$alkylamino, C$_{1-6}$alkoxy, or
C$_{1-6}$alkyl;
heteroaryl optionally substituted with one or more nitro, diC1$_6$alkylamino,
C$_{1-6}$alkoxy, or C$_{1-6}$alkyl;
C$_{1-10}$ straight or branched-chain alkyl optionally substituted with one or more halogen, nitro, C$_{1-6}$alkoxy, or aryl;
a polymer; or
a resin support;
R$_{3a}$ is H or C$_{1-6}$alkyl optionally substituted with one or more halogen; and at least one R$_4$, wherein each R$_4$ is independently hydrogen, halogen, nitro,
C$_{1-6}$alkoxy, C$_{1-6}$alkyl, aryl, or a resin support;
for a time and under conditions sufficient to produce the compound of formula Nu-E; wherein
Nu is an aryl compound, a heteroaryl compound, or an alkenyl compound;
E is an aryl compound, a heteroaryl compound, or an alkenyl compound; and X is iodo, chloro, or bromo.

2. The method of claim 1, wherein the compound of Formula I is

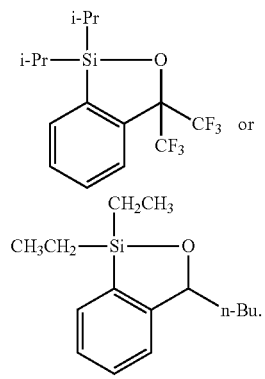

3. The method of claim 1, wherein the compound of Formula I is

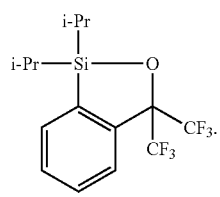 [SMILES: CC(C)[Si]1(C(C)C)OC(C(F)(F)F)(C(F)(F)F)c2ccccc21]

4. The method of claim 1, wherein the solvent is tetrahydrofuran.

5. The method of claim 1, wherein the palladium is $Pd(OAc)_2$.

6. The method of claim 1, wherein the phosphate ligand is XPhos, DavePhos, Johnphos, or SPhos.

7. The method of claim 6, wherein the phosphate ligand is XPhos.

8. The method of claim 1, wherein the phosphate ligand is Second Generation Buchwald Precatalyst, Third Generation Buchwald Precatalyst, or Fourth Generation Buchwald Precatalyst.

9. The method of claim 1, wherein the catalyst system comprises $Pd(OAc)_2$ and XPhos.

10. The method of claim 1, wherein Nu is phenyl.

11. The method of claim 1, wherein Nu is pyridyl.

12. The method of claim 1, wherein E is phenyl substituted with one or two of $C_{1-6}$alkyl, —$OC_{1-6}$alkyl, halogen, —$C(O)_{1-6}$alkyl, —$COOC_{1-6}$alkyl, —CN.

13. The method of claim 1, wherein E is quinolinyl or benzoxazolyl.

14. The method of claim 1, wherein X is iodo or chloro.

15. The method of claim 1, wherein X is chloro.

16. The method of claim 1, further comprising the step of recovering the compound of Formula I.

* * * * *

UNITED STATES PATENT AND TRADEMARK OFFICE
CERTIFICATE OF CORRECTION

PATENT NO. : 9,850,261 B2
APPLICATION NO. : 15/326069
DATED : December 26, 2017
INVENTOR(S) : Adam T. Hoye et al.

Page 1 of 1

It is certified that error appears in the above-identified patent and that said Letters Patent is hereby corrected as shown below:

In the Specification

Column 1, Lines 23-26, delete "This invention was made with government support under Contract No. GM 29028 awarded by the National Institutes of Health. The government has certain rights in the invention." and insert -- This invention was made with government support under grant number GM029028 awarded by the National Institutes of Health. The government has certain rights in the invention. --.

Signed and Sealed this
Twenty-sixth Day of February, 2019

Andrei Iancu
*Director of the United States Patent and Trademark Office*